(12) United States Patent
Gregg

(10) Patent No.: US 11,118,212 B2
(45) Date of Patent: Sep. 14, 2021

(54) METHODS FOR DETECTING RAPIDLY PROCESSED INTRONS TO EVALUATE ALLELIC EXPRESSION

(71) Applicant: UNIVERSITY OF UTAH RESEARCH FOUNDATION, Salt Lake City, UT (US)

(72) Inventor: Christopher Gregg, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 532 days.

(21) Appl. No.: 15/731,763

(22) Filed: Jul. 28, 2017

(65) Prior Publication Data

US 2018/0087098 A1 Mar. 29, 2018

Related U.S. Application Data

(60) Provisional application No. 62/494,162, filed on Jul. 29, 2016.

(51) Int. Cl.
*C12Q 1/6827* (2018.01)
*C12Q 1/6809* (2018.01)
*G16B 25/20* (2019.01)
*C12Q 1/6841* (2018.01)

(52) U.S. Cl.
CPC ......... *C12Q 1/6827* (2013.01); *C12Q 1/6809* (2013.01); *C12Q 1/6841* (2013.01); *G16B 25/20* (2019.02)

(58) Field of Classification Search
CPC ... C12Q 1/6827; C12Q 1/6809; C12Q 1/6841
See application file for complete search history.

(56) References Cited

U.S. PATENT DOCUMENTS

| 7,709,198 | B2 | 5/2010 | Luo et al. |
| 8,604,182 | B2 | 12/2013 | Luo et al. |
| 8,658,361 | B2 | 2/2014 | Wu et al. |
| 8,951,726 | B2 | 2/2015 | Luo et al. |
| 2002/0192667 | A1 | 12/2002 | Kojima et al. |

OTHER PUBLICATIONS

Bhatt et al., Transcript Dynamics of Proinflammatory Genes Revealed by Sequence Analysis of Subcellular RNA Fractions, Jul. 20, 2012, Cell, 150, p. 279-290 (Year: 2012).*
Bai et al., IRcall and IRclassiifer: two methods for flexible detection of intron retention events from RNA-Seq data, 2015, BMC Genomics, 16(Suppl 2):S9, p. 1-9 (Year: 2015).*
Garber et al., Computational Methods for transcriptome annotation and quantification using RNA-seq, Jun. 2011, Nature Methods, p. 469-477 (Year: 2011).*
Lalonde et al., RNA sequencing reveals the role of splicing polymorphisms in regulating human gene expression, 2011, Genome Research, 21, p. 545-554 (Year: 2011).*
Buckley et al., Cytoplasmic Intron Sequence-Retaining Transcripts Can Be Dendritically Targeted via ID Element Retrotransposons, Mar. 10, 2011, Neuron, 69, p. 877-884 (Year: 2011).*
Van Raamsdonk et al., Optimizing the detecting of nascent transcripts by RNA fluorescence in situ hybridization, 2001, Nucleic Acids Research, 29(8), p. 1-3 (Year: 2001).*
Saliba et al., Single-cell RNA-seq: advances and future challenges, 2014, Nucleic Acids Research, 42(14), p. 8845-8860 (Year: 2014).*
Jensen, Technical Review: In Situ Hybridization, 2014, The Anatomical Record, 297, p. 1349-1353 (Year: 2014).*
Agha-Mohammadi et al., "Regulatable systems: applications in gene therapy and replicating viruses," J. Clin. Invest., 2000, 105(9): 1177-1183.
Anders et al., "HTSeq—a Python framework to work with high-throughput sequencing data," Bioinformatics, 2014, 31(2):166-169.
Babak et al., "Genetic conflict reflected in tissue-specific maps of genomic imprinting in human and mouse," Nat. Genet., 2015, 47: 544-549.
Babak et al., "Global survey of genomic imprinting by transcriptome sequencing," Curr. Biol., 2008, 18: 1735-1741.
Barbazuk et al., "SNP discovery via 454 transcriptome sequencing," Plant J., 2007, 51: 910-918.
Bartolomei et al., "Mammalian genomic imprinting," Cold Spring Harb. Perspect. Biol., 2011, 3: a002592.
Bird, "Extraction of RNA from cells and tissue," Methods Mol. Med., 2005, 108: 139-48.
Bonthuis et al., "Noncanonical Genomic Imprinting Effects in Offspring," Cell Reports 12, 2015, pp. 979-991.
Brash et al, "Strontium phosphate transfection of human cells in primary culture: stable expression of the simian virus 40 large-T-antigen gene in primary human bronchial epithelial cells," Mol. Cell Biol., 1987, 7: 2031-2034.
Butler, "Genomic imprinting disorders in humans: a mini-review," J. Assist. Reprod. Genet., 2009, 26(9-10): 477-486.
Calaway et al., "Genetic Architecture of Skewed X Inactivation in the Laboratory Mouse," PLoS Genet., 2013, 9: e1003853.
Carneiro et al., "The Multiple LIM Domain-Containing Adaptor Protein Hic-5 Synaptically Colocalizes and Interacts with the Dopamine Transporter," J. Neurosci, 2002, 22: 7045-7054.
Chadwick et al., "Genetic and parent-of-origin influences on X chromosome choice in Xce heterozygous mice," Mamm. Genome, 2005, 16: 691-699.
Cloonan et al., "Stem cell transcriptome profiling via massive-scale mRNA sequencing," Nature Methods, 2008, 5: 613-619.

(Continued)

*Primary Examiner* — Olivia M. Wise
*Assistant Examiner* — Kaitlyn L Minchella
(74) *Attorney, Agent, or Firm* — Michael Best & Friedrich LLP

(57) ABSTRACT

The invention is directed to methods for identifying one or more introns of a gene that are rapidly processed from a nascent RNA molecule transcribed from the gene, which allows for the detection of allele-specific expression of a gene in a single cell.

4 Claims, 111 Drawing Sheets
(87 of 111 Drawing Sheet(s) Filed in Color)
Specification includes a Sequence Listing.

(56) References Cited

OTHER PUBLICATIONS

Crowley et al., "Analyses of allele-specific gene expression in highly divergent mouse crosses identifies pervasive allelic imbalance," Nat. Genet., 2015, 47: 353-360.
Davies et al., "Xlr3b is a new imprinted candidate for X-linked parent-of-origin effects on cognitive function in mice," Nat. Genet., 2005, 37: 625-9.
Dindot et al., "Epigenetic profiling at mouse imprinted gene clusters reveals novel epigenetic and genetic features at differentially methylated regions," Genome Res., 2009, 19: 1374-1383.
Dobin et al., "STAR: ultrafast universal RNA-seq aligner," Bioinformatics., 2013, 29(1):15-21.
Doe et al., "Loss of the imprinted snoRNA mbii-52 leads to increased 5htr2c pre-RNA editing and altered 5HT2CR-mediated behaviour," Hum. Mol. Genet., 2009, 18: 2140-2148.
Emrich et al., "Gene discovery and annotation using LCM-454 transcriptome sequencing," Genome Res., 2007, 17: 69-73.
Espelund et al., "A simple method for generating single-stranded DNA probes labeled to high activities," Nuc. Acids. Res., 1990, 18(20): 6157-6158.
Feero et al., "Genomic Medicine—An Updated Primer," N. Engl. J. Med., 2010, 362 (21): 2001-2011.
Fernandez-Medarde et al., "The RasGrf family of mammalian guanine nucleotide exchange factors," Biochim. Biophys. Acta, 2011, 1815: 170-188.
Flicek et al., "Ensembl 2014," Nucleic Acids Res. 2014, 42(Database issue):D749-55.
Fowlis et al., "Further evidence for the importance of parental source of the Xce allele in X chromosome inactivation," Genet. Res., 1991, 58: 63-65.
Goverdhana et al., "Regulatable gene expression systems for gene therapy applications: progress and future challenges," Mol. Ther., 2005, 12(2): 189-211.
Gregg et al., "High Resolution Analysis of Parent-of-Origin Allelic Expression in the Mouse Brain," Science, 2010, 329: 643-648.
Gregg et al., "Sex-Specific Parent-of-Origin Allelic expression in the Mouse Brain," Science, 2010, 329: 682-685.
Haig, "The Kinship Theory of Genomic Imprinting," Annu. Rev. Ecol. Syst., 2000, 31: 9-32.
Harrow et al., "GENCODE: the reference human genome annotation for the ENCODE Project," Genome Res., 2012, 22(9):1760-74.
Holt et al., "The new paradigm of flow cell sequencing," Genome Res., 2008, 18: 839-846.
Hsu et al., "The UCSC Known Genes," Bioinformatics. 2006, 22(9):1036-46.
Huguet et al., "The genetic landscapes of autism spectrum disorders," Annu. Rev. Genomics Hum. Genet., 2013, 14: 191-213.
Iglesias-Platas et al., "Imprinting at the PLAGL1 domain is contained within a 70-kb CTCF/cohesin-mediated non-allelic chromatin loop," Nucleic Acids Res., 2013, 41: 2171-2179.
Jelini et al., "Loss of imprinting and cancer.," J. Pathol., 2007, 211(3): 261-268.
Johnston, "Biolistic transformation: microbes to mice," Nature, 1990, 346: 776-777.
Joyce et al.., "Genomic imprinting and cancer," Mol. Pathol., 1998, 51(4): 185-190.
Khatib, "Is it genomic imprinting or preferential expression?" Bio-Essays, 2007, 29: 1022-1028.
Kim et al., "TopHat2: accurate alignment of transcriptomes in the presence of insertions, deletions and gene fusions," Genome Biol. 2013, 14(4):R36.
Kitts et al., "A method for producing recombinant baculovirus expression vectors at high frequency," Biotechniques, 1993, 14: 810-817.
Kobayashi et al., "Modest neuropsychological deficits caused by reduced noradrenaline metabolism in mice heterozygous for a mutated tyrosine hydroxylase gene," J. Neurosci, 2000, 20: 2418-2426.
Kumar, A., Int. J. Applied Biology and Pharmaceutical Technology, 2010, 1(2): 418-430.
Li et al., "RNA-Seq gene expression estimation with read mapping uncertainty," Bioinformatics, 2009, 26:493-500.
Li et al., "RSEM: accurate transcript quantification from RNA-Seq data with or without a reference genome," BMC Bioinformatics, 2011, 12: 323.
Li et al., "The Sequence Alignment/Map format and SAMtools," Bioinformatics, 2009, 25: 2078-2079.
Li, "A statistical framework for SNP calling, mutation discovery, association mapping and population genetical parameter estimation from sequencing data," Bioinformatics, 2011, 27: 2987-2993.
Li, "Improving SNP discovery by base alignment quality" Bioinformatics, 2011, 27: 1157-1158.
Liao et al., "featureCounts: an efficient general purpose program for assigning sequence reads to genomic features," Bioinformatics, 2014, 30(7): 923-30.
Lister et al., "Highly integrated single-base resolution maps of the epigenome in *Arabidopsis*," Cell, 2008, 133: 523-536.
Loman et al., "Performance comparison of benchtop high-throughput sequencing platforms," Nat. Biotechnol., 2012, 30: 434-439.
Lucklow, "Baculovirus systems for the expression of human gene products," Curr. Opin. Biotechnol., 1993, 4: 564-572.
Luckow et al., "Efficient generation of infectious recombinant baculoviruses by site-specific transposon-mediated insertion of foreign genes into a baculovirus genome propagated in *Escherichia coli*," J. Virol., 1993, 67: 4566-4579.
Mantione et al., "Comparing Bioinformatic Gene Expression Profiling Methods: Microarray and RNA-Seq," Med. Sci. Monit. Basic Res., 2014, 20: 138-141.
Marioni et al., "RNA-seq: an assessment of technical reproducibility and comparison with gene expression arrays," Genome Res., 2008, 18(9): 1509-17.
McCarthy et al., "Differential expression analysis of multifactor RNA-Seq experiments with respect to biological variation," Nucleic Acids Res, 2012, 40: 4288-4297.
Meacham et al., "Identification and correction of systematic error in high-throughput sequence data," BMC Bioinformatics, 2011, 12: 451.
Miller et al., "Longer life spans and delayed maturation in wild-derived mice," Exp. Biol. Med. (Maywood), 2002, 227: 500-508.
Morin et al., "Profiling the HeLa S3 transcriptome using randomly primed cDNA and massively parallel short-read sequencing," Biotechniques, 2008, 45: 81-94.
Mortazavi et al., "Mapping and quantifying mammalian transcriptomes by RNA-Seq," Nature Methods, 2008, 5: 621-628.
Nagalakshmi et al., "The transcriptional landscape of the yeast genome defined by RNA sequencing," Science, 2008, 320: 1344-1349.
Nicolae et al., "Estimation of alternative splicing isoform frequencies from RNA-Seq data," Algorithms Mol Biol., 2011, 6:9.
Peirson et al., "RNA extraction from mammalian tissues," Methods Mol. Biol., 2007, 362: 315-27.
Pruitt et al., "NCBI reference sequences (RefSeq): a curated non-redundant sequence database of genomes, transcripts and proteins," Nucleic acids Res. 2007, 35(Database):D61-65.
Raefski et al., "Identification of a cluster of X-linked imprinted genes in mice," Nat. Genet., 2005, 37: 620-624.
Robinson et al., "edgeR: a Bioconductor package for differential expression analysis of digital gene expression data," Bioinformatics, 2010, 26: 139-140.
Schulz et al., "WAMIDEX: a web atlas of murine genomic imprinting and differential expression," Epigenetics, 2008, 3: 89-96.
Schwanhäusser et al., "Global quantification of mammalian gene expression control," Nature, 2011, 473: 337-342.
Singh et al., "Coordinated allele-specific histone acetylation at the differentially methylated regions of imprinted genes," Nucleic Acids Res., 2010, 38: 7974-7990.
Tan et al., "DNA, RNA, and Protein Extraction: The Past and the Present," J. Biomedicine and Biotechnol., 2009, Article ID 574398.

(56) References Cited

OTHER PUBLICATIONS

Tang et al., "Simple and effective methods for generating single-stranded DNA targets and probes," Biotechniques, 2006, 40(6): 759-763.
Trapnell et al., "Transcript assembly and quantification by RNA-Seq reveals unannotated transcripts and isoform switching during cell differentiation," Nat Biotechnol., 2010, 28: 511-515.
Urlaub et al., "Isolation of Chinese hamster cell mutants deficient in dihydrofolate reductase activity," Proc. Natl. Acad. Sci. USA, 1980, 97: 4216-4220.
Vera et al., "Rapid transcriptome characterization for a nonmodel organism using 454 pyrosequencing," Mol. Ecol., 2008, 17: 1636-1647.
Wagner et al., "Measurement of mRNA abundance using RNA-seq data: RPKM measure is inconsistent among samples," Theory Biosci., 2012, 131(4): 281-285.
Wang et al., "A Survey for Novel Imprinted Genes in the Mouse Placenta by mRNA-seq," Genetics, 2011, 189: 109-122.
Wang et al., "Automated quantitative RNA in situ hybridization for resolution of equivocal and heterogeneous ERBB2 (HER2) status in invasive breast carcinoma," J of Mol. Diagnostics, 2013, 15(2):210-219.
Wang et al., "Hypothalamic Ahi1 Mediates Feeding Behavior through Interaction with 5-HT2C Receptor," J. Biol. Chem., 2012, 287: 2237-2246.
Wang et al., "MapSplice: accurate mapping of RNA-seq reads for splice junction discovery," Nucleic Acids Res. 2010, 38(18):e178.
Wang et al., "Paternally biased X inactivation in mouse neonatal brain," Genome Biol., 2010, 11: R79.
Wang et al., "RNAscope. A Novel in Situ RNA Analysis Platform for Formalin-Fixed, Paraffin-Embedded Tissues," J of Mol. Diagnostics, 2012, 14(1):22-29.
Wang et al., "RNA-Seq: a revolutionary tool for transcriptomics," Nature Reviews Genetics, 2009, 10(1): 57-63.
Wang et al., "Transcriptome-Wide Identification of Novel Imprinted Genes in Neonatal Mouse Brain," PLoS ONE, 2008, 3: e3839.
Wilcox, "Fundamental principles of in situ hybridization," J. Histochemistry and Cytochemistry, 1993, 41(12): 1725-1733.
Wilhelm et al., "Dynamic repertoire of a eukaryotic transcriptome surveyed at single-nucleotide resolution," Nature, 2008, 453:1239-1243.
Wilkins et al., "Diseases associated with genomic imprinting," Prog. Mol. Biol. Transl. Sci., 2011, 101: 401-45.
Wolf, "Principles of transcriptome analysis and gene expression quantification: an RNA-seq tutorial," Molecular Ecology Resources, 2013, 13: 559-572.
Wu et al., "Fast and SNP-tolerant detection of complex variants and splicing in short reads," Bioinformatics, 2010, 26(7):873-81.
Xie et al., "Base-resolution analyses of sequence and parent-of-origin dependent DNA methylation in the mouse genome," Cell, 2012, 148: 816-831.
Yang et al., "Global survey of escape from X inactivation by RNA-sequencing in mouse," Genome Res., 2010, 20: 614-622.
Zeller et al., "In situ hybridization to cellular RNA," Curr Protoc Mol Biol., 2001, Chapter 14:Unit 14.3.

* cited by examiner

FIG. 1H

SEQUENCE LISTING

```
<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gtggggatgg aggaatca                                                    18

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
gtatgcgcaa agccaaggt                                                   19

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
ggatggagga atcaata                                                     17

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ggcctccttt cagctttctg c                                                21
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgcccctact gcgtctagtg                                              20

<210> SEQ ID NO 6
<211> LENGTH: 15
<212> TYPE: DNA
<213> ORGANISM: Artificial Sequence
<220> FEATURE:
<223> OTHER INFORMATION: Synthetic

<400> SEQUENCE: 6
gcagggctct tctga                                                   15

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
cggtgccagc caggtagt                                                18

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gaataggaag ccggtgcag                                               19

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
gcgtgttccg cggtt                                                   15

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
gggctagaca ggaacaagac at                                           22

<210> SEQ ID NO 11
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 11
aggaaaaaac acagcagaga gg                                            22

<210> SEQ ID NO 12
<211> LENGTH: 15
<212> TYPE: DNA
<213> ORGANISM: Artificial Sequence
<220> FEATURE:
<223> OTHER INFORMATION: Synthetic

<400> SEQUENCE: 12
ttcaaggggc agatg                                                    15

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
gcccagaacc tcccaacc                                                 18

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
agcaggagag tcgcatcca                                                19

<210> SEQ ID NO 15
<211> LENGTH: 15
<212> TYPE: DNA
<213> ORGANISM: Artificial Sequence
<220> FEATURE:
<223> OTHER INFORMATION: Synthetic

<400> SEQUENCE: 15
ataccgtgag gggtc                                                    15

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
tacacggata cacacacctg c                                             21

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
tcatgctaga ggacacagta cca                                           23

<210> SEQ ID NO 18
<211> LENGTH: 17
```

```
<212> TYPE: DNA
<213> ORGANISM: Artificial Sequence
<220> FEATURE:
<223> OTHER INFORMATION: Synthetic

<400> SEQUENCE: 18
gcagttacct gggaagt                                                        17

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
ggccaggaac cccaacgc                                                       18

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
ctccaggcct cggctcct                                                       18

<210> SEQ ID NO 21
<211> LENGTH: 16
<212> TYPE: DNA
<213> ORGANISM: Artificial Sequence
<220> FEATURE:
<223> OTHER INFORMATION: Synthetic

<400> SEQUENCE: 21
cgctgtgtaa gtgccc                                                         16

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
tgggccgcac tctctgaag                                                      19

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
ggaagcccct aaacacagga ca                                                  22

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
```
cgcactctct gaagcat                                              17

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
gtttcggaga tgaaaggac ctat                                       24

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
gactttcttg acctctgctc tacc                                      24

<210> SEQ ID NO 27
<211> LENGTH: 15
<212> TYPE: DNA
<213> ORGANISM: Artificial Sequence
<220> FEATURE:
<223> OTHER INFORMATION: Synthetic

<400> SEQUENCE: 27
cctgggagca ctcaa                                                15

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
aagacagcct cggatctgtg a                                         21

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
tgtttgtggg gggtctcc                                             18

<210> SEQ ID NO 30
<211> LENGTH: 15
<212> TYPE: DNA
<213> ORGANISM: Artificial Sequence
<220> FEATURE:
<223> OTHER INFORMATION: Synthetic

<400> SEQUENCE: 30
tacgcctctc ggaaa                                                15

<210> SEQ ID NO 31
<211> LENGTH: 20
<212> TYPE: DNA
<213> ORGANISM: Artificial Sequence

```
<220> FEATURE:
<223> OTHER INFORMATION: Synthetic

<400> SEQUENCE: 31 gagggggctaa tgggactgga                                              20

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
gttgagtccc ggcgctct                                                 18

<210> SEQ ID NO 33
<211> LENGTH: 15
<212> TYPE: DNA
<213> ORGANISM: Artificial Sequence
<220> FEATURE:
<223> OTHER INFORMATION: Synthetic

<400> SEQUENCE: 33
gggcaggacc atacc                                                    15
```

METHODS FOR DETECTING RAPIDLY PROCESSED INTRONS TO EVALUATE ALLELIC EXPRESSION

CROSS-REFERENCE TO RELATED APPLICATION(S)

This claims priority to U.S. Provisional Patent Application No. 62/494,162, filed on Jul. 29, 2016, the entire contents of which are fully incorporated herein by reference.

INCORPORATION-BY-REFERENCE OF MATERIAL SUBMITTED VIA CD-ROM

Incorporated by reference in their entirety herein are data tables included on the CD-ROM submitted concurrently herewith and identified as follows: One 14,227 byte EXCELX file named "U6015_Table 1_S1.XLSX," one 5.58 megabyte EXCELX file named "U6015_Table 2_S2.XLSX," one 39.1 kilobyte EXCELX file named "U6015_Table 3_S3.XLSX," one 25.6 kilobyte EXCELX file named "U6015_Table 4_S4.XLSX," one 37.1 kilobyte EXCELX file named "U6015_Table 5_S5.XLSX," and one 1,150 byte ASCII (Text) file named "U6015_Table 6_S6," all of which were created on Jul. 28, 2016.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,342 Byte ASCII (Text) file named "026389-9186-US01_ST25.txt," created on Nov. 1, 2017.

BACKGROUND OF THE INVENTION

Many inherited genetic risk factors for complex disorders, such as neuropsychiatric disorders, are heterozygous in the affected individuals (Huguet et al., *Annu. Rev. Genomics Hum. Genet.*, 14: 191-213 (2013)). Therefore, understanding allele-specific expression effects in different tissues and cell types is essential for understanding how inherited mutations may impact offspring. Genomic imprinting is a heritable form of epigenetic gene regulation that results in preferential expression of the maternal or paternal allele for at least 100 genes in mammals (Bartolomei and Ferguson-Smith, *Cold Spring Harb. Perspect. Biol.*, 3: a002592-a002592 (2011)). In females, imprinting can influence both autosomal and X-linked genes, and a consequence of imprinting is that the effect of an inherited mutation is influenced by the parental origin.

Canonical imprinting is associated with complete silencing of one gene copy. Indeed, models of the Kinship Theory for the evolution of imprinting predict that evolutionary parental conflicts drive complete silencing of one parent's allele at loci that influence offspring demands on maternal resources (Haig, *Annu. Rev. Ecol. Syst.*, 31: 9-32 (2000)). However, other studies have noted that some imprinted genes exhibit a bias to express either the maternal or paternal allele, rather than complete silencing (Khatib, *Bio-Essays*, 29: 1022-1028 (2007)). Compared to canonical imprinted genes, genes that exhibit allele expression biases might be associated with different mechanisms, functions, and selective pressures. The effects of such allele expression biases are referred to as "noncanonical imprinting effects."

One approach to profile imprinting in the developing and adult mouse brain using RNA sequencing (RNA-seq) uncovered noncanonical imprinting effects that influence the expression of hundreds of genes (Gregg et al., *Science*, 329: 682-685 (2010), Gregg et al., *Science*, 329: 643-648 (2010)). Other studies of imprinting in somatic tissues, however, have produced inconsistent results. For example, while some studies have found very few novel imprinted genes in mice (Babak et al., *Curr. Biol.*, 18: 1735-1741 (2008); Wang et al., *PLoS ONE*, 3: e3839 (2008)), another study of the mouse liver uncovered 535 imprinted genes (Goncalves et al., *Genome Res.*, 22: 2376-2384 (2012)). Moreover, two recent studies of imprinting in different mouse tissues reached different conclusions regarding the prevalence of imprinting and the identity of the novel imprinted genes detected (Babak et al., *Nat. Genet.*, 47: 544-549 (2015); and Crowley et al., *Nat. Genet.*, 47: 353-360 (2015)). Thus, noncanonical imprinting effects in the genome remain poorly understood, and the mechanisms involved and possible function(s) of noncanonical imprinting are unknown. In addition to imprinting, allele expression biases may also be the result of random monoallelic expression effects, loss-of-heterozygosity, and gene copy number variation effects.

Thus, there remains a need for methods to determine allele-specific gene expression to determine whether a gene exhibits monoallelic or biallelic expression in a subject or tissue. The present disclosure provides such methods.

BRIEF SUMMARY OF THE INVENTION

This disclosure provides methods for identifying one or more introns of a gene that are rapidly processed from one or more nascent RNA molecules transcribed from the gene, which methods comprise: (a) providing a cell comprising a gene of interest, (b) expressing the gene of interest in the cell, (c) isolating one or more nascent RNA molecules transcribed from the gene of interest, (d) sequencing the one or more nascent RNA molecules isolated in (c), (e) determining the fragments per kilobase per millions (FPKM) for each exon and each intron present in the one or more nascent RNA molecules, and (f) calculating an intron retention score (IRS) for each intron of the one or more nascent RNA molecules as follows:

$$IRS = \frac{intron\ FPKM}{mean\ FPKM\ for\ two\ flanking\ exons},$$

wherein the mean FPKM for two flanking exons is the mean FPKM for each exon directly flanking an intron, (e) ranking each intron of the one or more nascent RNA molecules according to the intron retention score for each intron, wherein a lower intron retention score indicates that the intron is rapidly processed and a higher intron retention score indicates that the intron is not rapidly processed.

This disclosure also provides methods for detecting allele-specific expression of a gene in a single cell, which methods comprise: (a) providing a cell comprising a gene of interest, (b) expressing the gene of interest in the cell, (c) isolating one or more nascent RNA molecules transcribed from the gene of interest, (d) sequencing the one or more nascent RNA molecules isolated in (c), (e) determining the fragments per kilobase per millions (FPKM) for each exon and each intron present in the nascent RNA, (f) calculating an intron retention score (IRS) for each intron of the one or more nascent RNA molecules as follows:

$$IRS = \frac{intron\ FPKM}{mean\ FPKM\ for\ two\ flanking\ exons},$$

wherein the mean FPKM for two flanking exons is the mean FPKM for each exon directly flanking an intron, (g) ranking each intron of the one or more nascent RNA molecules according to the intron retention score for each intron, wherein a lower intron retention score indicates that the intron is rapidly processed and a higher intron retention score indicates that the intron is not rapidly processed, (h) designing one or more nucleic acid probes that specifically bind to a rapidly processed intron identified by steps (a)-(g), wherein the one or more probes comprise a detectable label, (i) conducting RNA in situ hybridization on the rapidly processed intron using the one or more probes, and (j) detecting a signal produced by the detectable label, wherein the presence of one signal indicates that the gene of interest is expressed from one allele and the presence of two signals indicates that the gene of interest is expressed from two alleles.

BRIEF DESCRIPTION OF THE SEVERAL VIEWS OF THE DRAWING(S)

This patent or application file contains at least one drawing executed in color. Copies of this patent or patent application publication with color drawing(s) will be provided by the Office upon request and payment of the necessary fee.

Figure 1A:
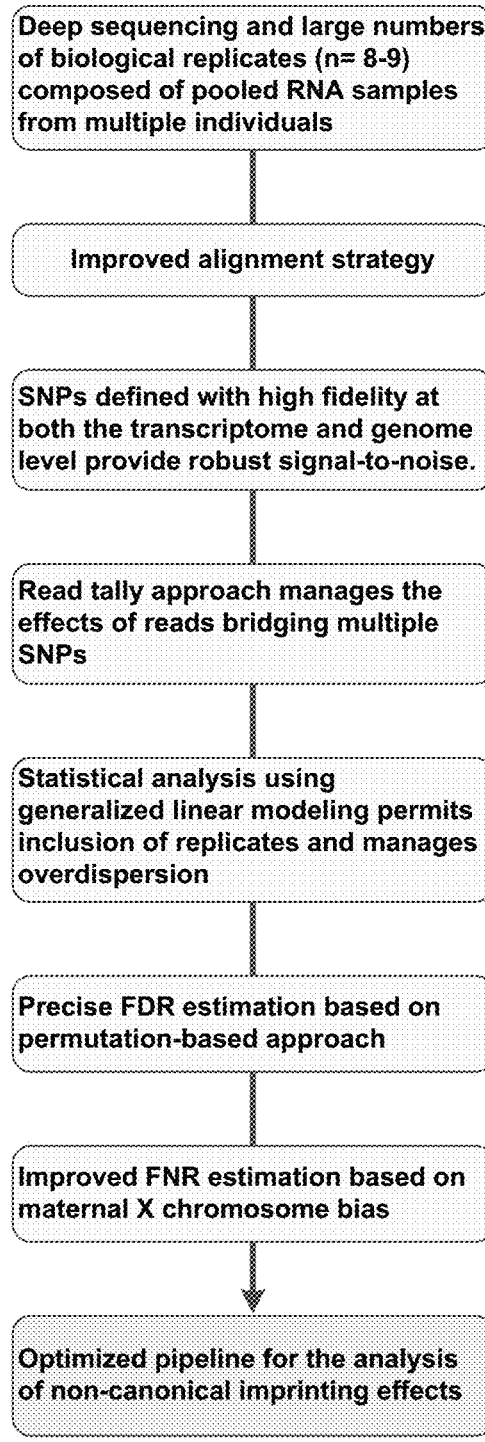
FIG. 1A is a schematic overview of an optimized analysis pipeline for the detection of noncanonical imprinting effects.
Figure 1B:
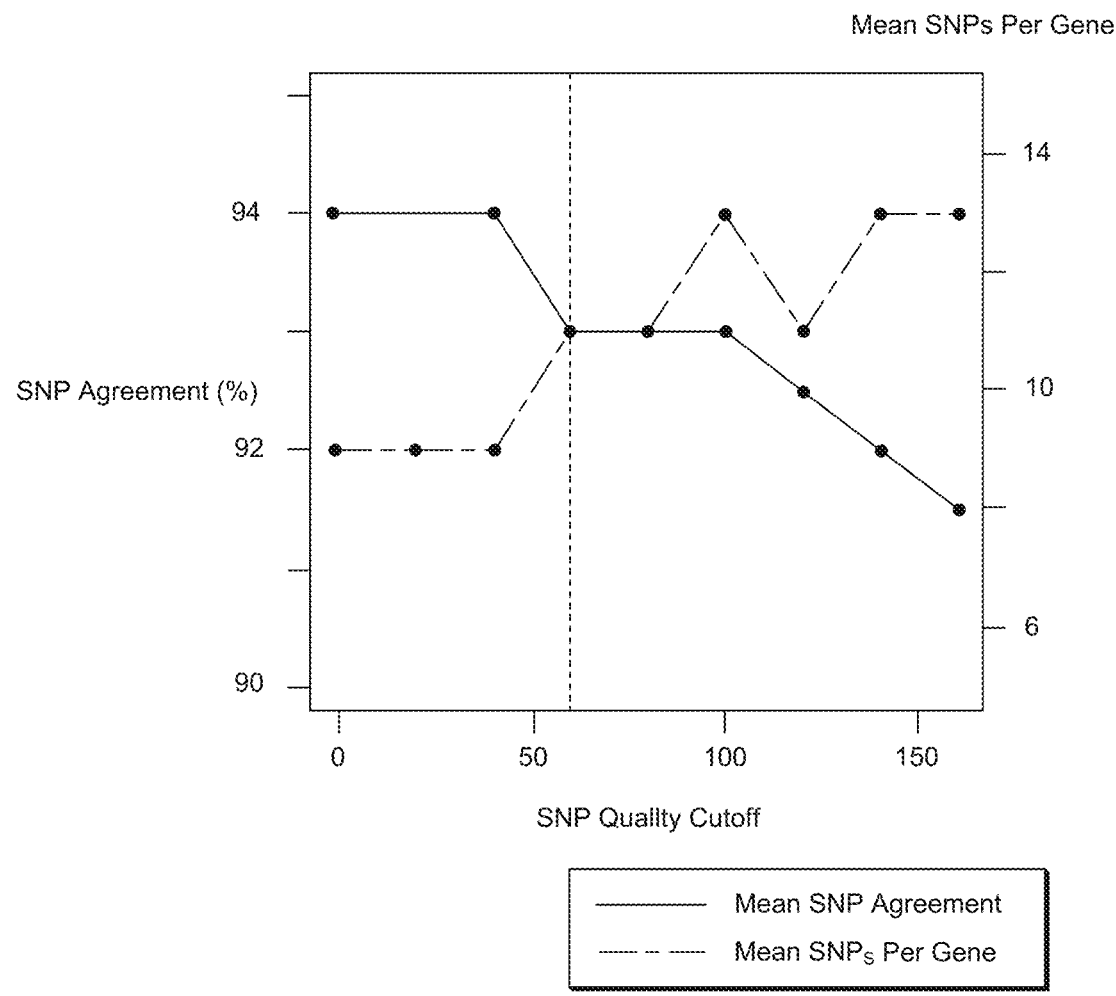
FIG. 1B is a line graph showing that a SNP quality score cutoff of 60 yielded a high agreement between SNPs, in terms of the direction of the allele bias for SNPs in the same imprinted gene (93% of SNPs indicate the same direction of allele bias). The mean number of SNPs per imprinted gene is eleven at the quality score cutoff of 60.

FIG. 1H is a schematic depicting the study design (REAL) and permuted study design (PERMUTED). The permuted data intermingled the Fli and Flr samples to scramble the parental origin of the samples relative to the glm design matrix for the statistical detection of imprinting effects. Imprinting effects detected in the permuted condition were false. The data was permuted according to this pattern 500 times to determine the mean number of false positives at different p value cutoffs.

Figure 2A:
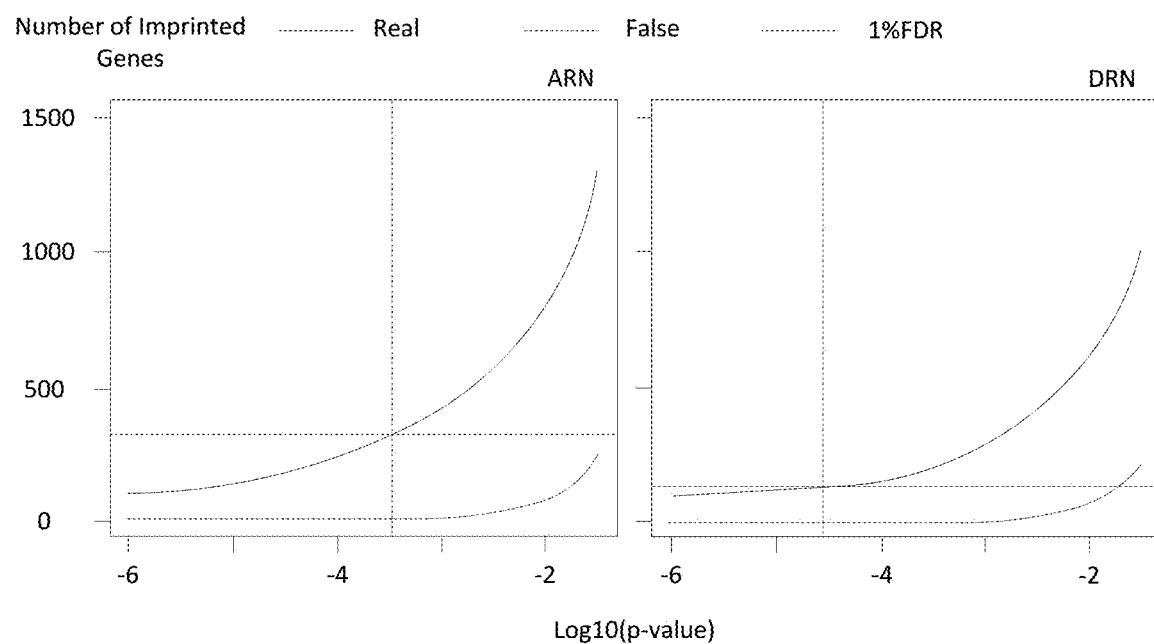
Figure 2B:
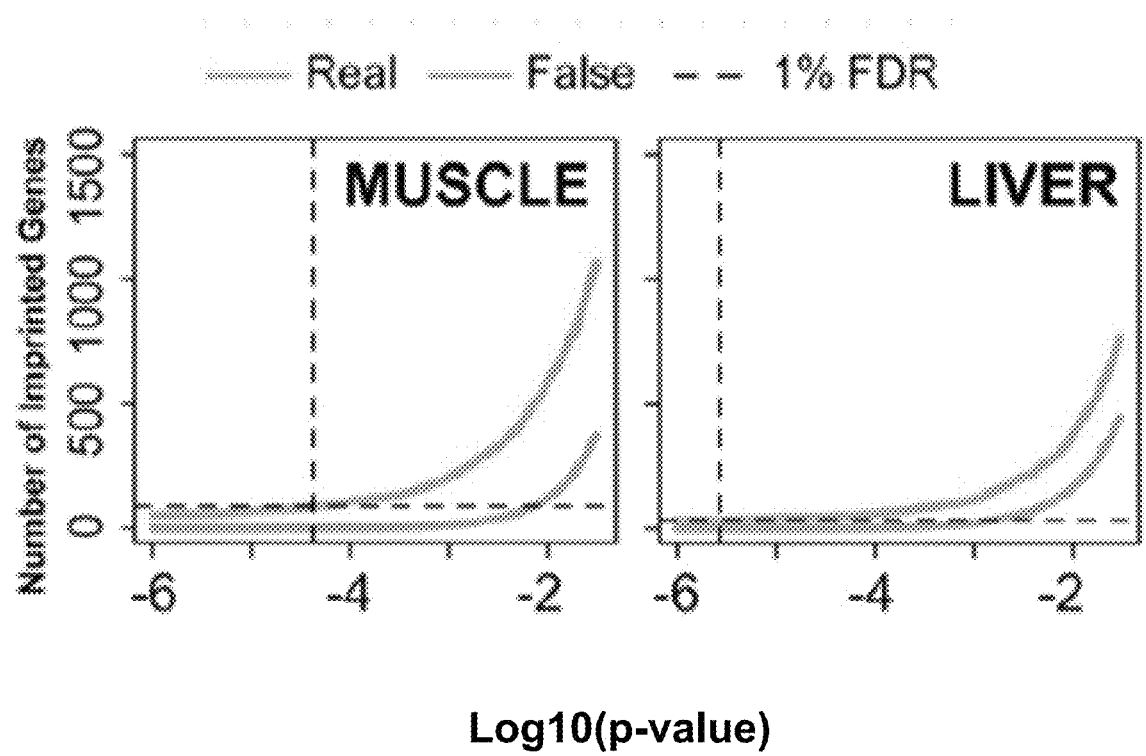

FIG. 2A and FIG. 2B are line graphs showing the detection of imprinting effects in the adult female ARN, DRN, liver, and muscle. The number of imprinted genes detected by RNA-seq (top line) and the estimated false-positives (bottom line) at different p value cutoffs are shown (dashed line is 1% FDR).

Figure 2C:
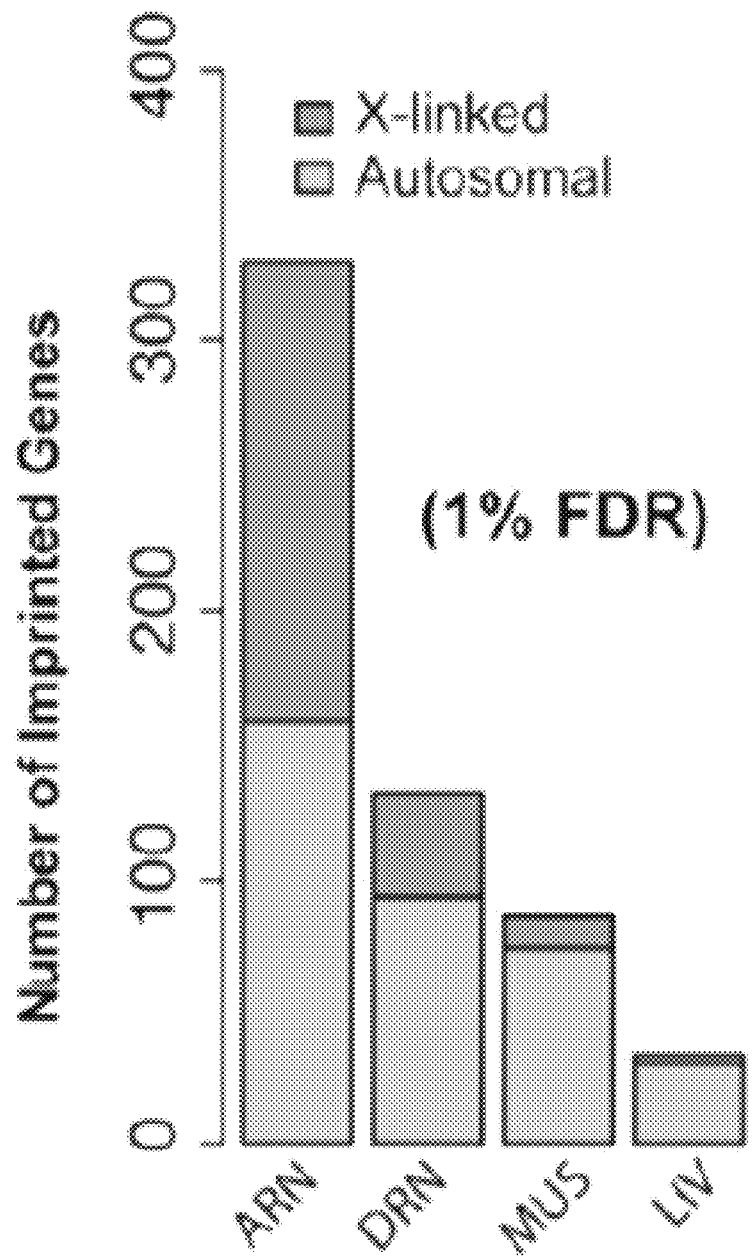

FIG. 2C is a bar graph showing the number of autosomal (bottom bars) and X-linked (top bars) imprinted genes in each tissue at the 1% FDR.

Figure 2D:
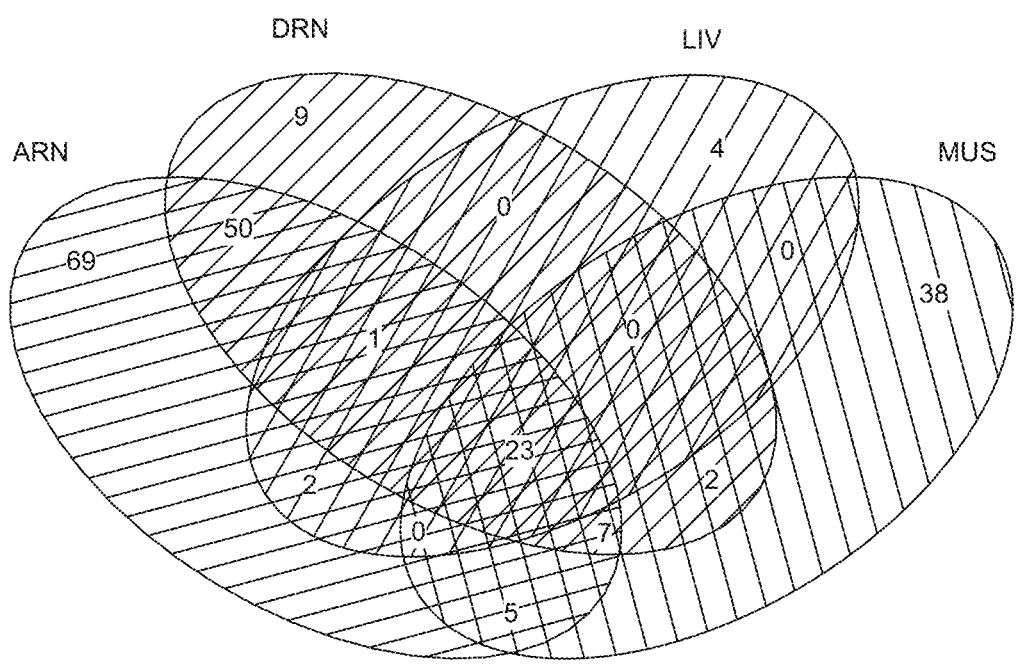

FIG. 2D is a Venn diagram of autosomal imprinted genes detected in each tissue at the 1% FDR.

Figure 2E:
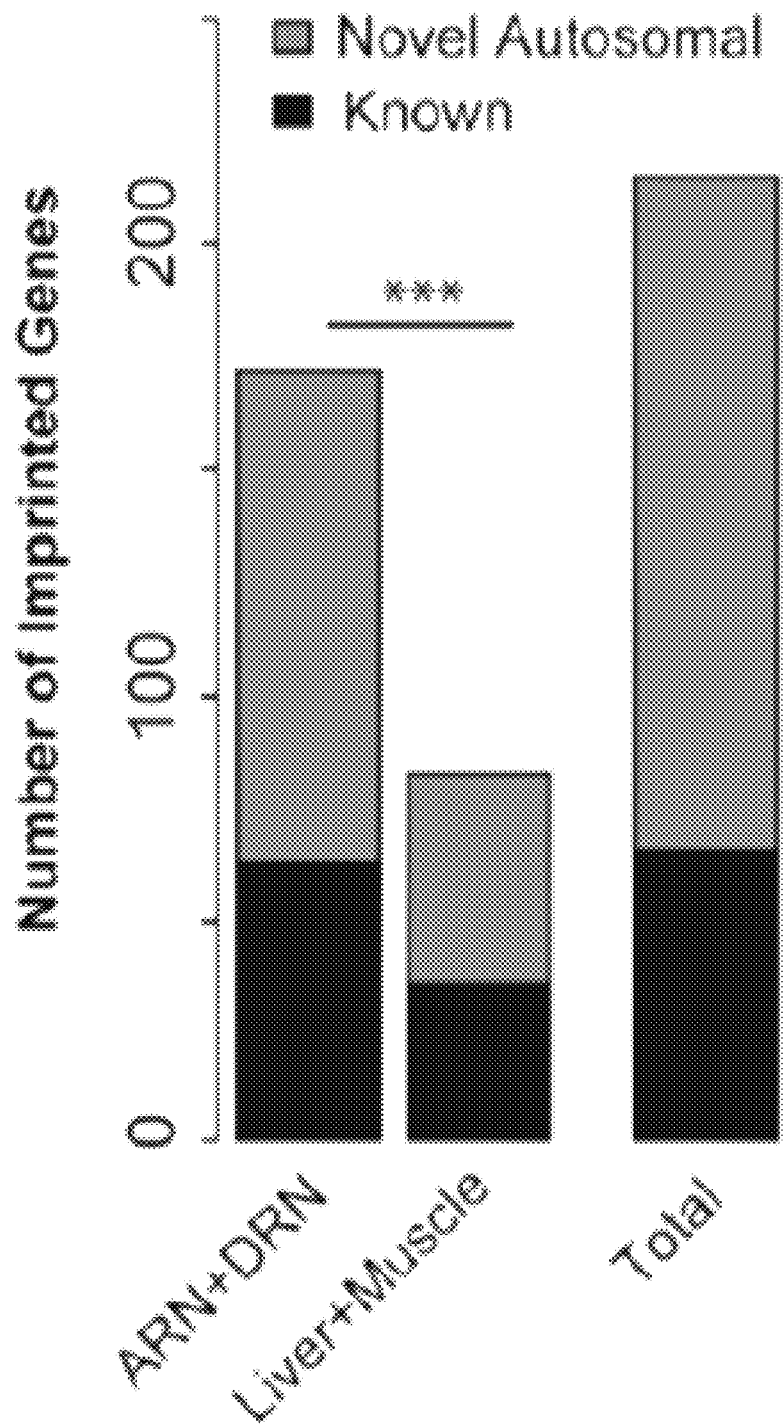

FIG. 2E is a bar graph showing the number of novel (gray bars) and known (black bars) autosomal imprinted genes uncovered in the ARN and DRN (neural) compared to the muscle and liver (non-neural), as well as the total number in all tissues.

Figure 2F:
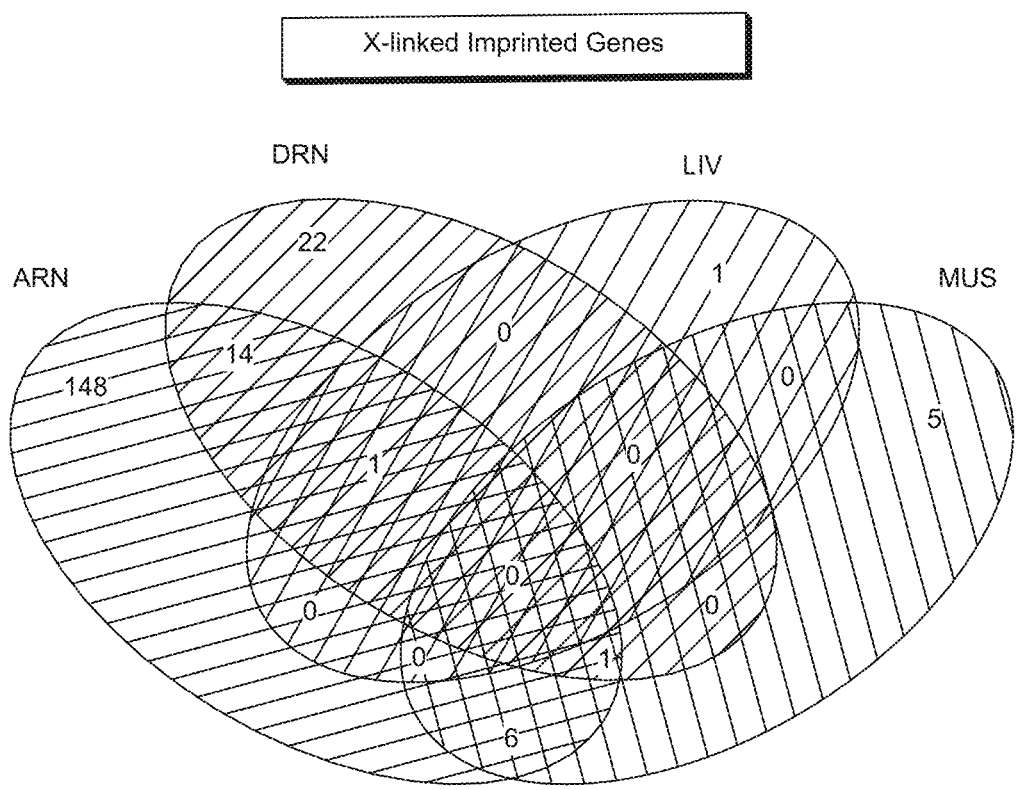

FIG. 2F is a Venn diagram of X-lined imprinted genes detected at the 1% FDR cutoff in each tissue.

Figure 2G:
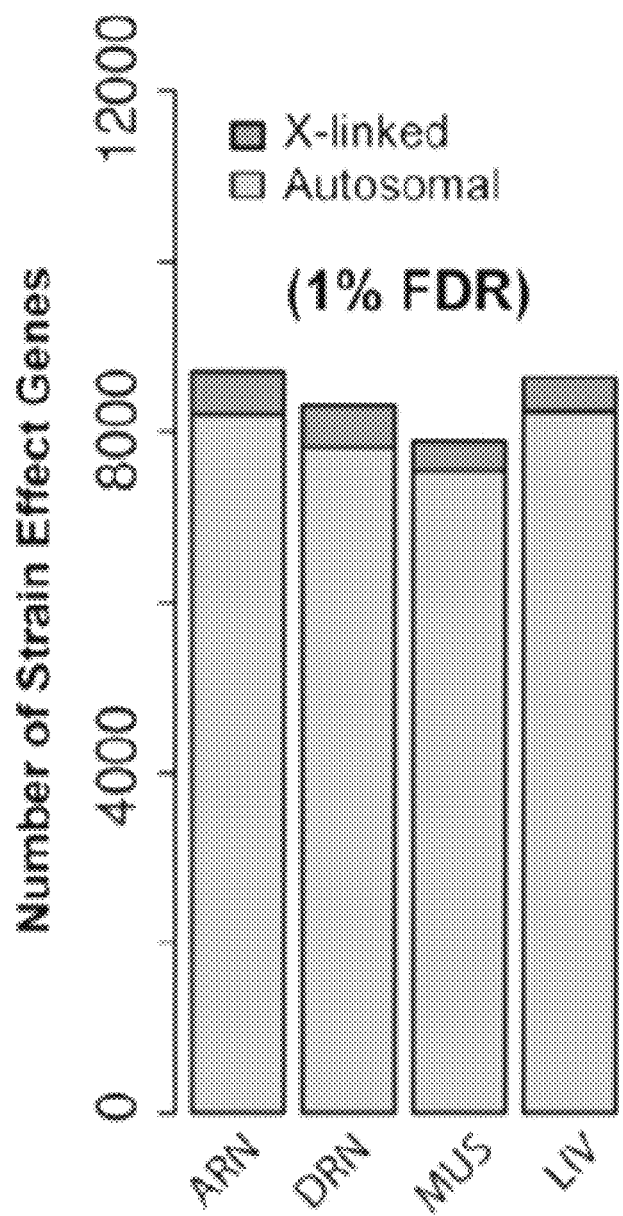

FIG. 2G is a bar graph showing the number of autosomal (bottom bars) and X-linked genes (top bars) that exhibit genetic strain effects in each tissue at the 1% FDR.

Figure 3A:
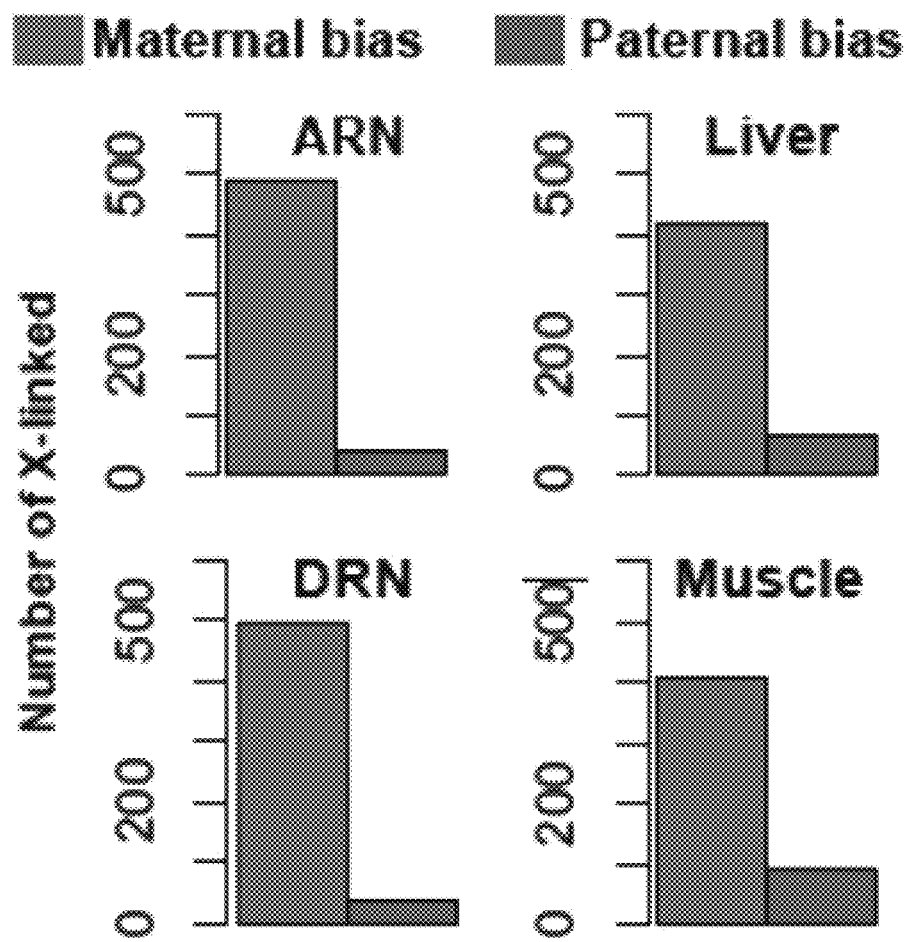

FIG. 3A is a bar graph showing plots of the number of X-linked genes that exhibited a mean maternal (left bars) versus paternal (right bars) allele expression bias, which revealed that most X-linked genes exhibit a maternal bias in the ARN, DRN, liver, and muscle.

Figure 3B:
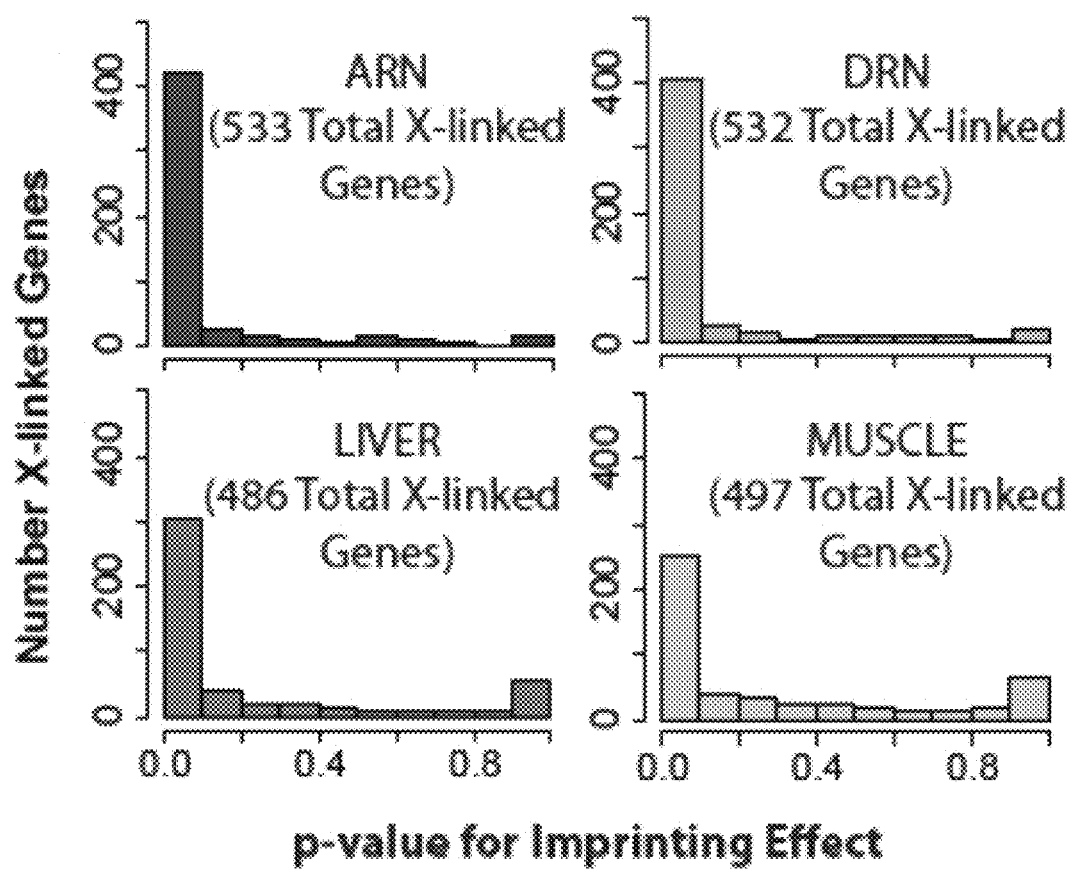

FIG. 3B is a bar graph showing plots of the p-values for imprinting effects for X-linked genes, which revealed that the maternal bias is statistically detected in each tissue at the gene level, as demonstrated by shifting of the p-value distribution toward low p-values. Thus, most X-linked genes exhibited a statistically detectable maternal bias.

Figure 3C:
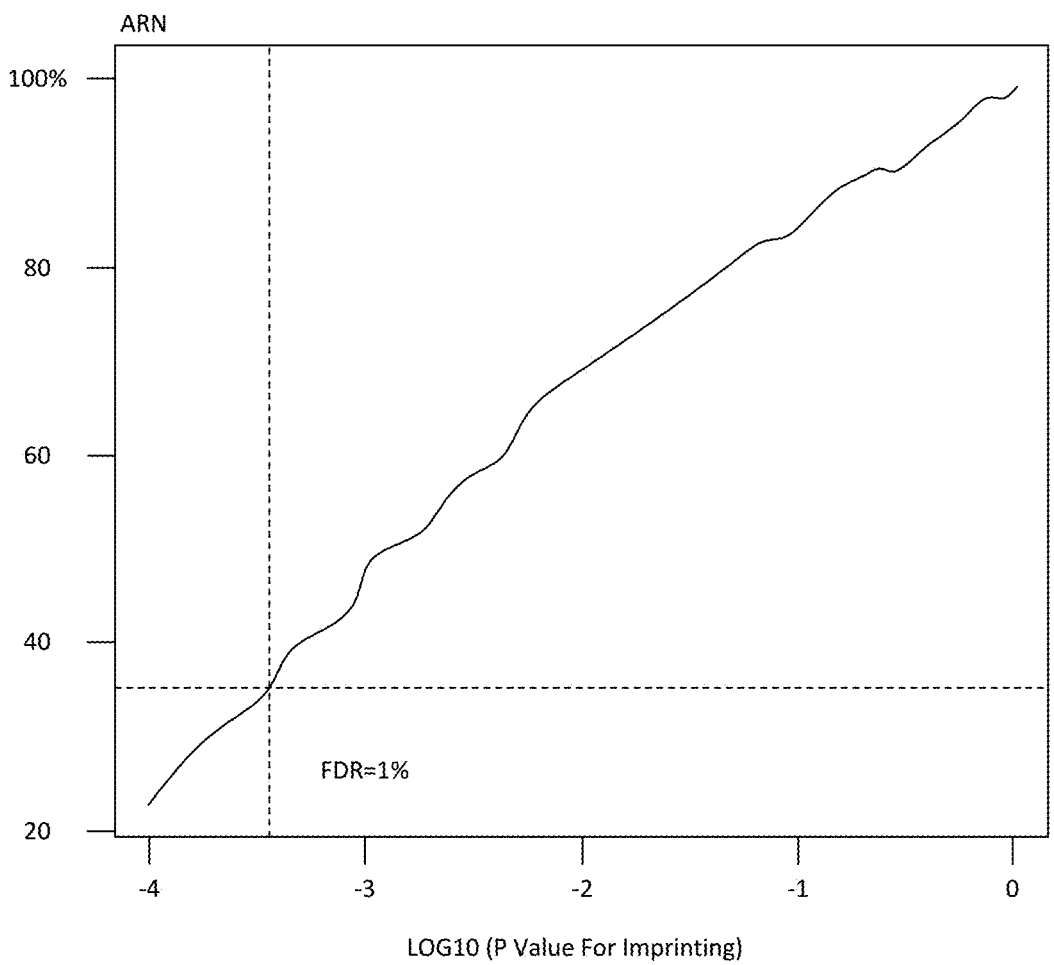

FIG. 3C is a plot showing the percentage of all maternally biased X-linked genes expressed in the ARN that were discovered as imprinted at different p value cutoffs. The p value cutoff that yielded a 1% FDR detected 35% of all maternally biased X-linked genes. Thus, 65% of maternally biased X-linked genes were not detected (shaded area) indicating that false negatives (type II statistical errors) exist in the datasets.

Figure 4A:
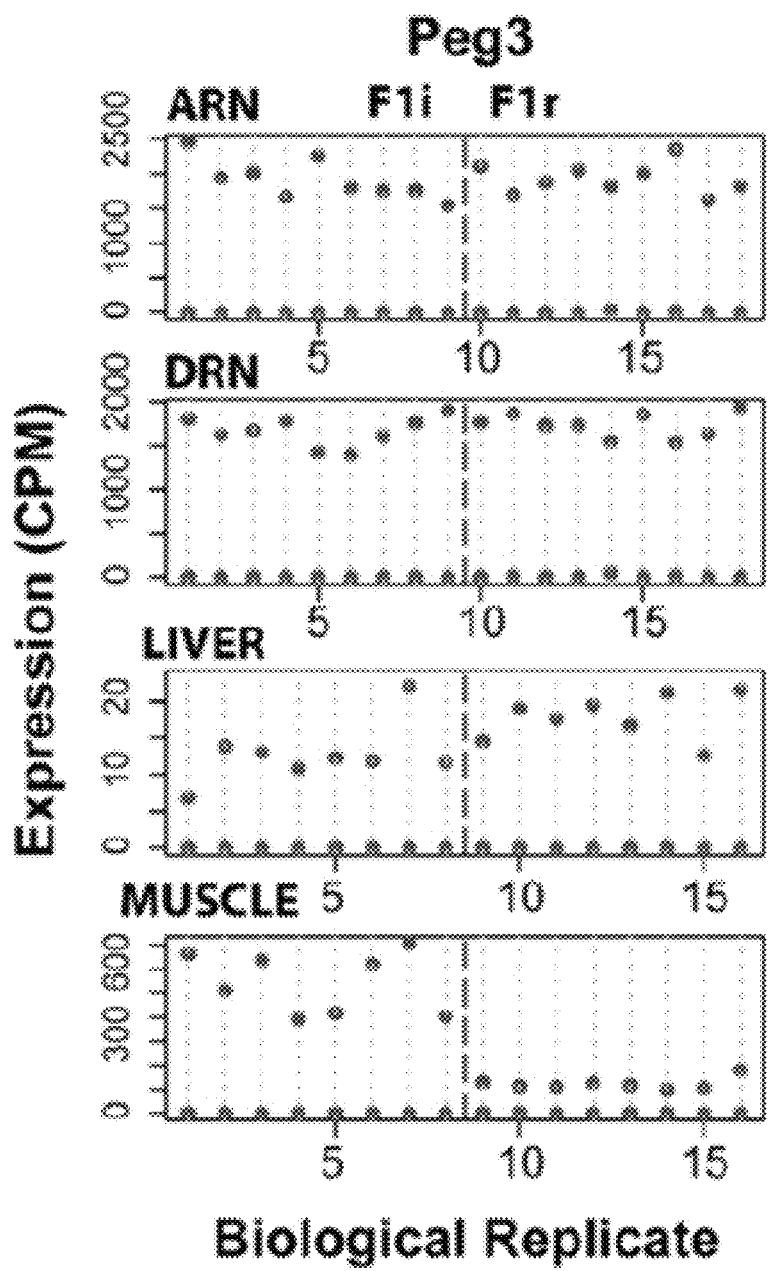
Figure 4B:
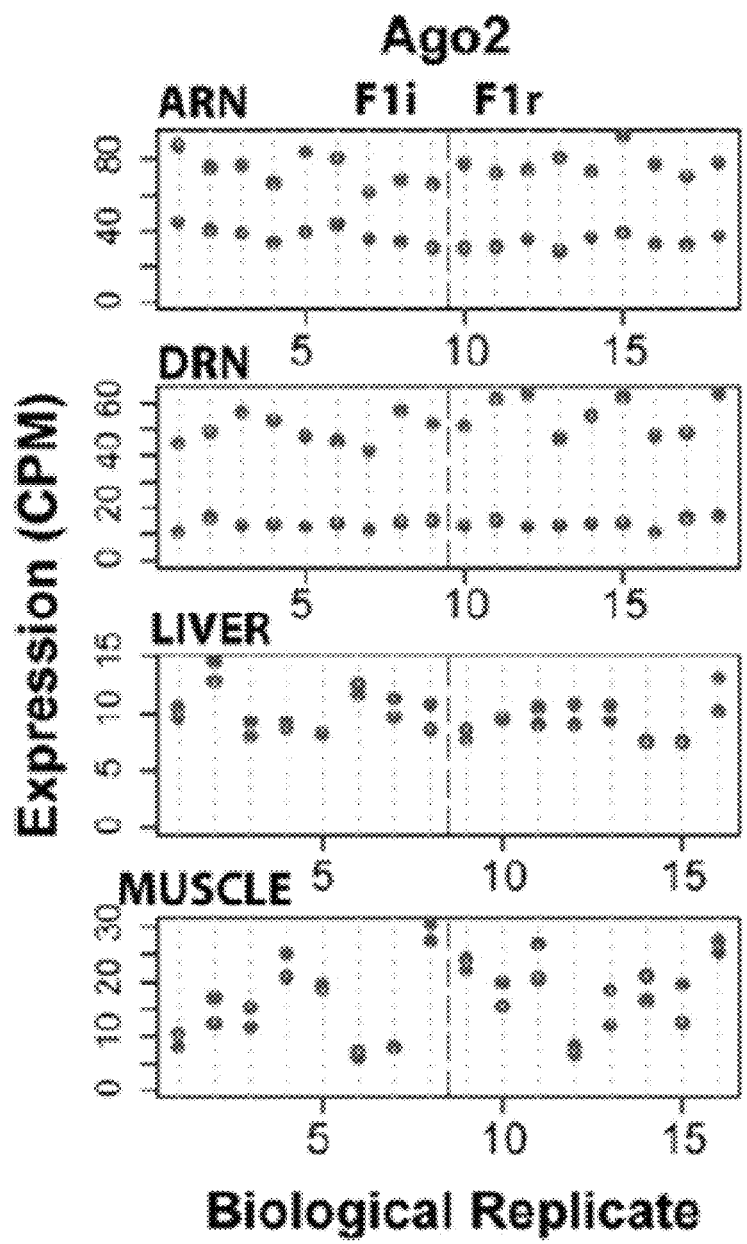

FIG. 4A and FIG. 4B are dot plots showing examples of canonical (Peg3) and noncanonical (Ago2) imprinting in the ARN, DRN, liver, and muscle detected by RNA-seq. Peg3 exhibited silencing of the maternal allele (red dots) and expression of the paternal allele (blue dots) in all tissues and biological replicates for Fli and Flr hybrid offspring. Ago2 exhibited a maternal bias in the ARN and DRN and no effect in the liver or muscle.

Figure 4C:
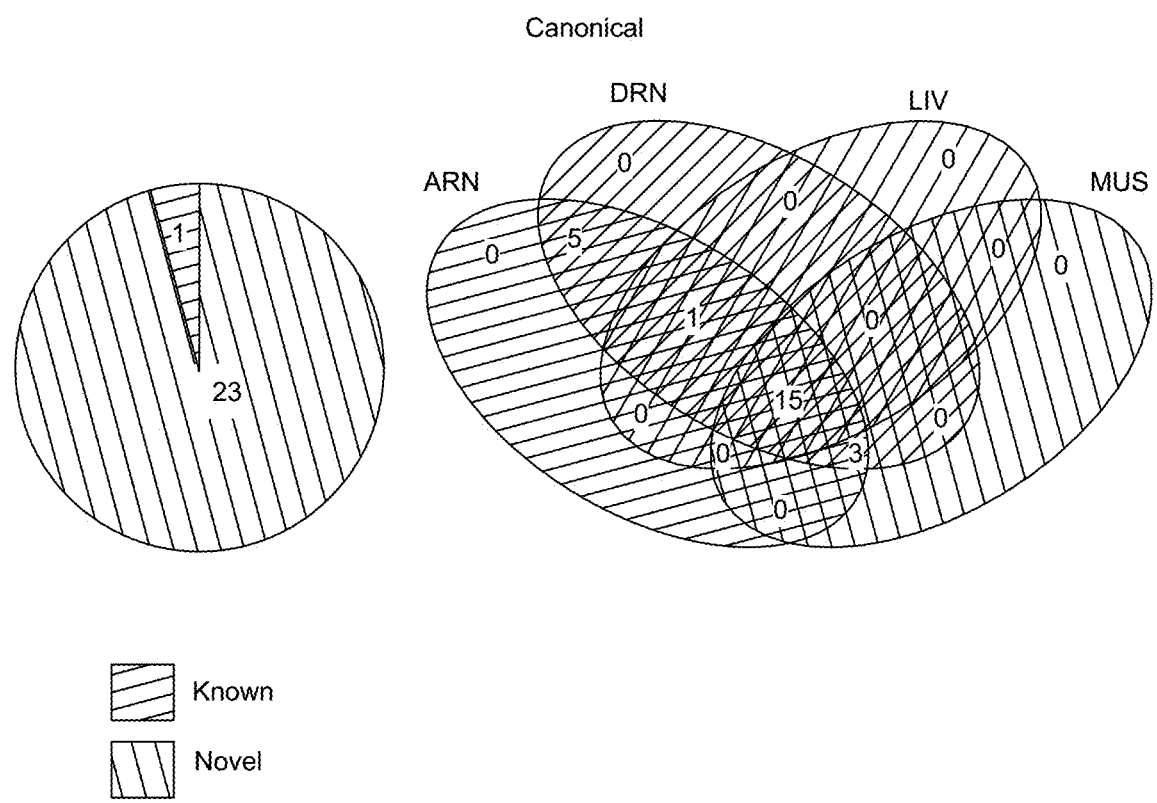
Figure 4D:
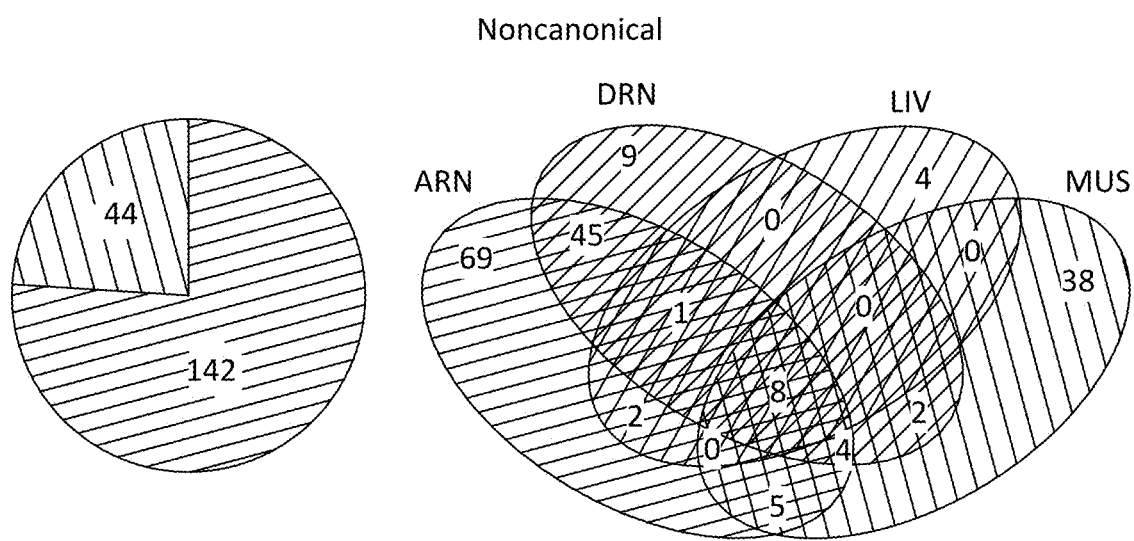

FIG. 4C and FIG. 4D are pie charts showing the total number of known and novel canonical (C) and noncanonical (D) imprinted genes discovered, and a Venn analysis of the tissues in which the genes were found.

Figure 4E:
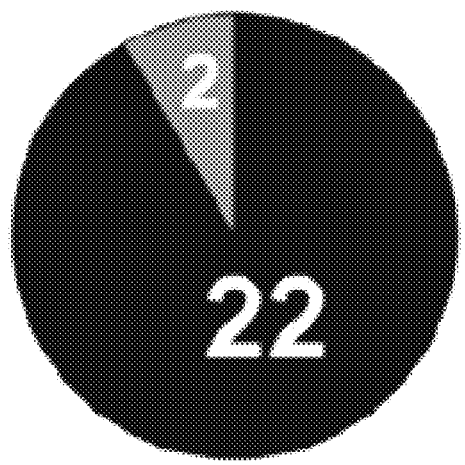
Figure 4E:
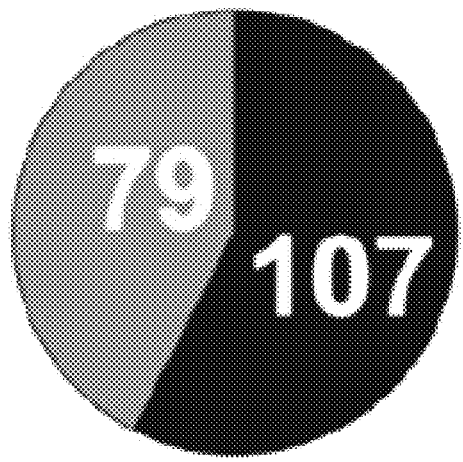

FIG. 4E is a pie chart showing the number of canonical and noncanonical imprinted genes in clusters (clustered, black) compared to novel genomic regions (remote, gray).

Figure 5A:
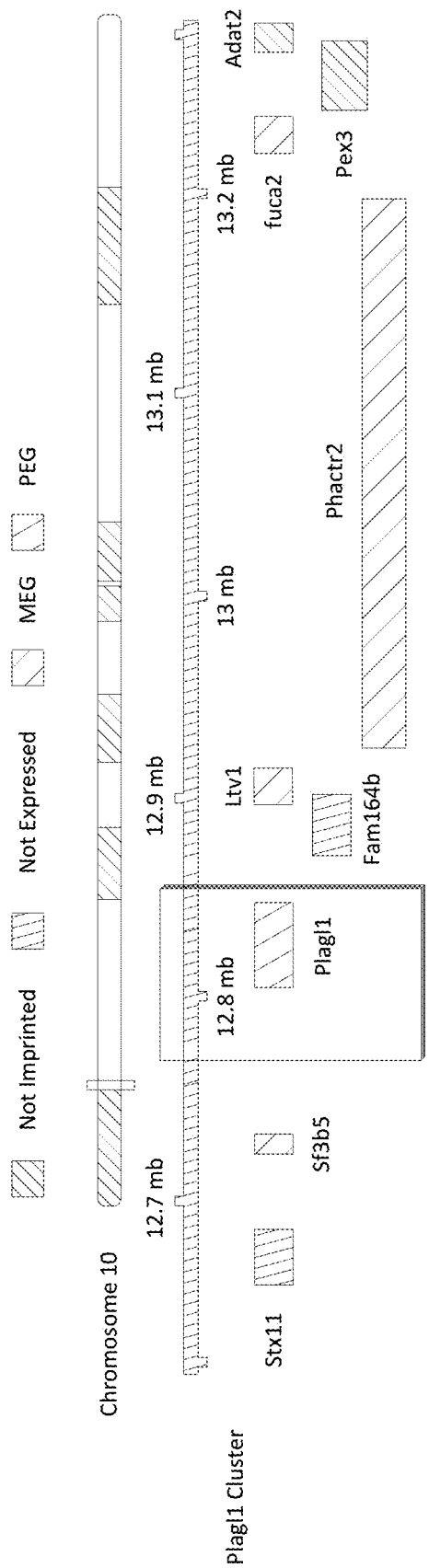
Figure 5B:
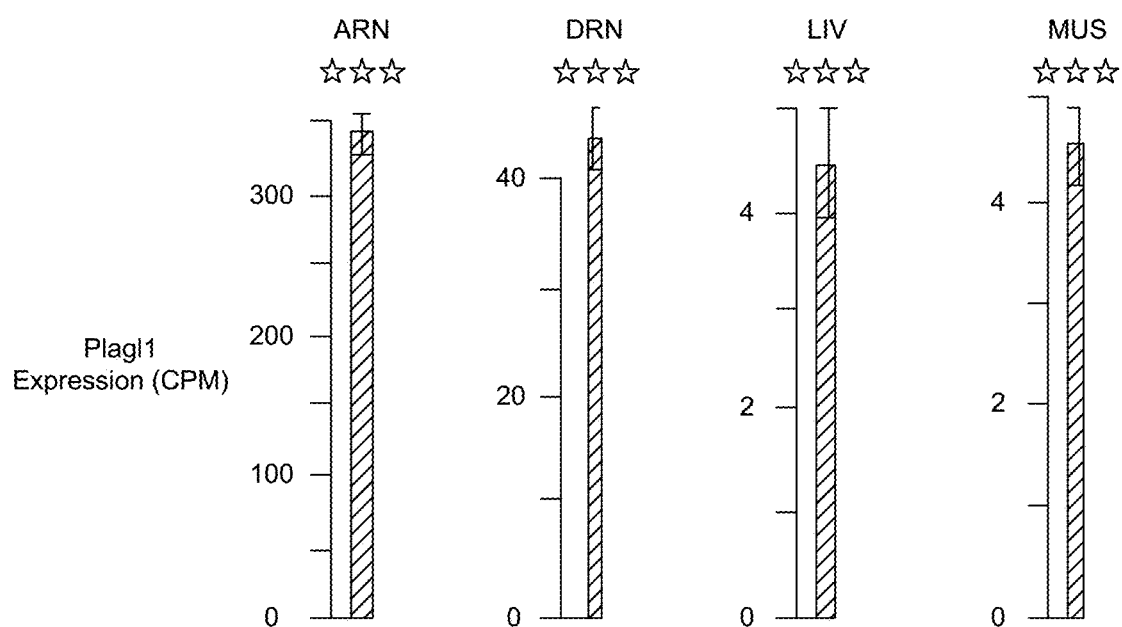

FIG. 5A is a schematic of the Plagl1 imprinted gene cluster on chromosome 10.

FIG. 5B to FIG. 5F are bar graphs of the RNASeq results for genes in the Plagl1 cluster showing that Plagl1 exhibited canonical imprinting that involved silencing of the maternal allele in all four tissues. Sf3b5 (C) and Ltv1 (D) exhibited a noncanonical maternal bias in the ARN only, while Phactr2 (E) exhibited a maternal bias in the ARN and DRN. Fuca2 (F) exhibited a maternal bias in the ARN and muscle.

Figure 5C:
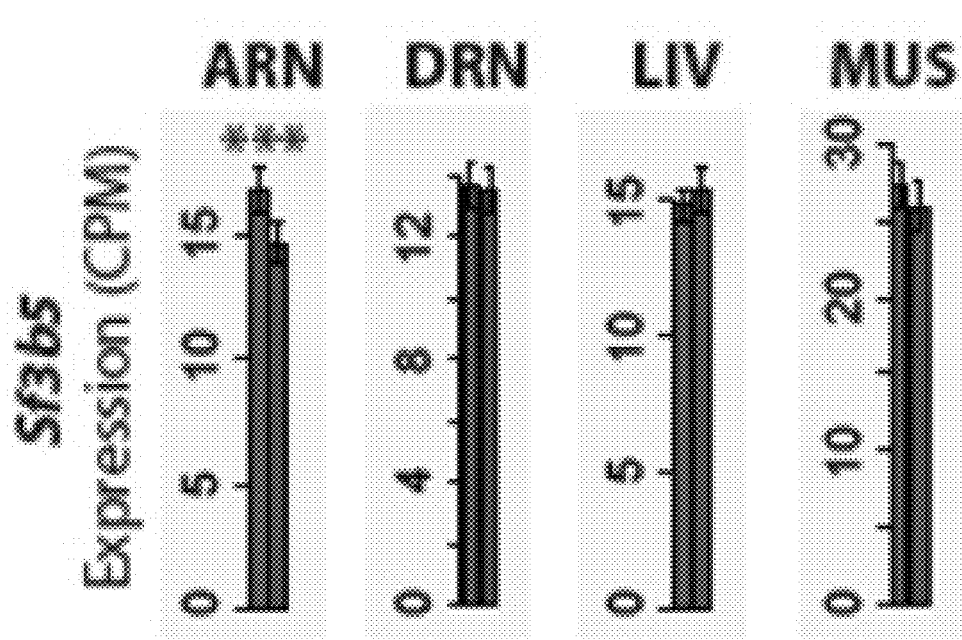
Figure 5D:
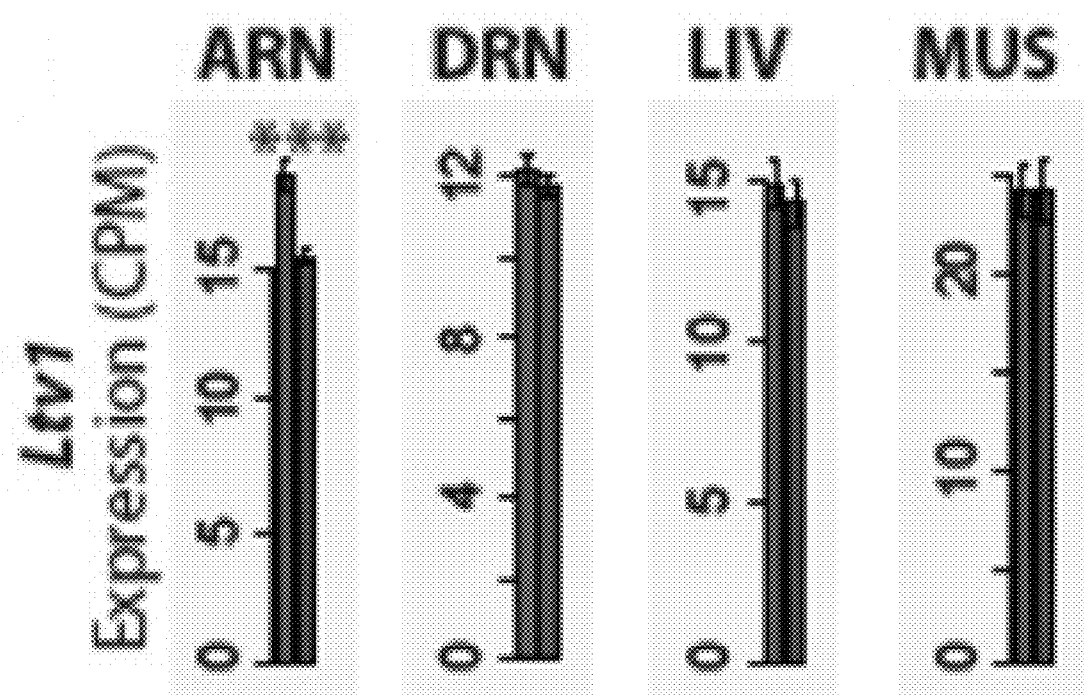
Figure 5E:
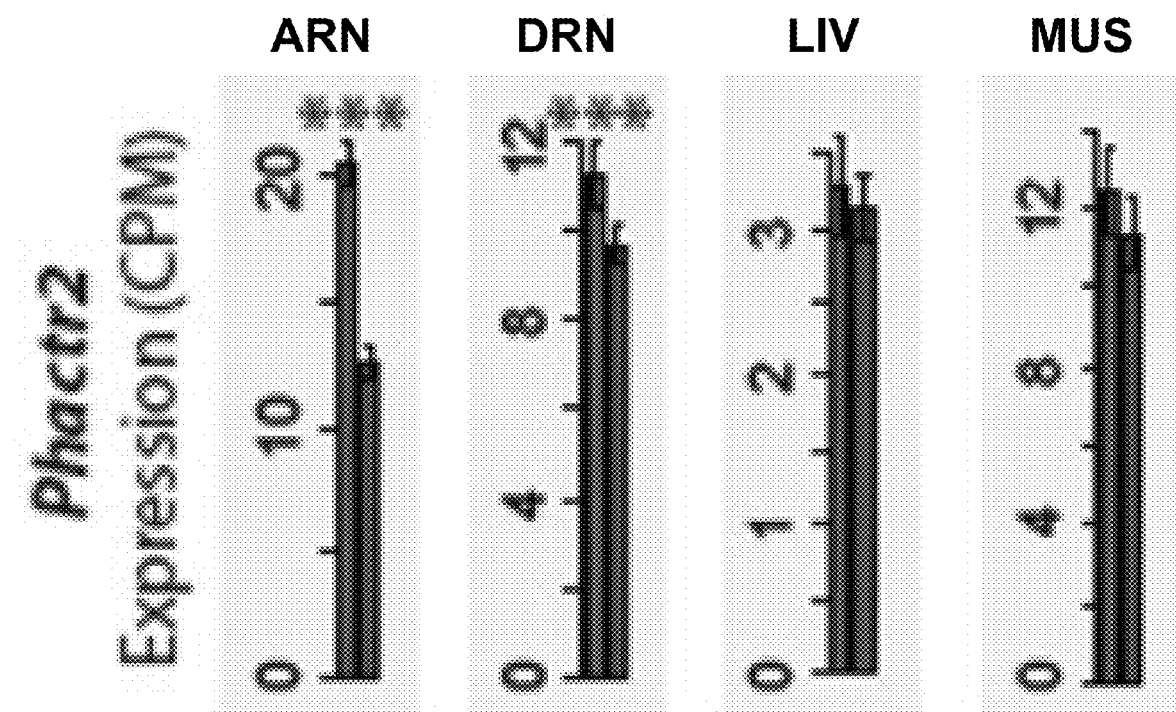
Figure 5F:
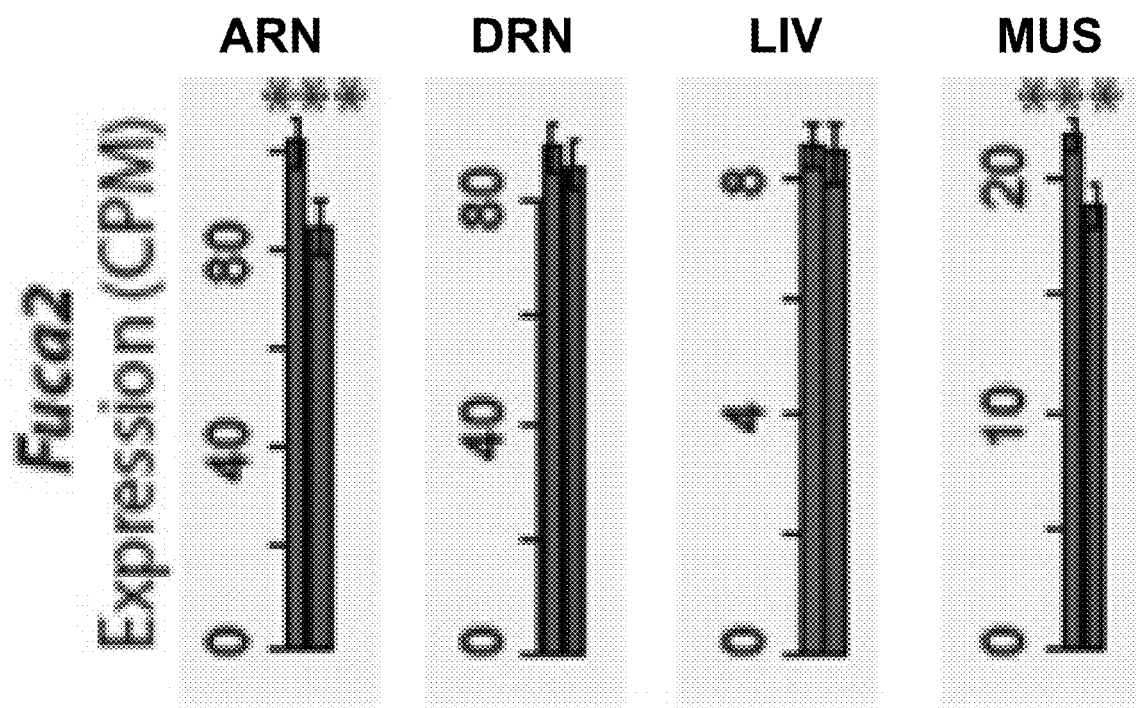
Figure 5G:
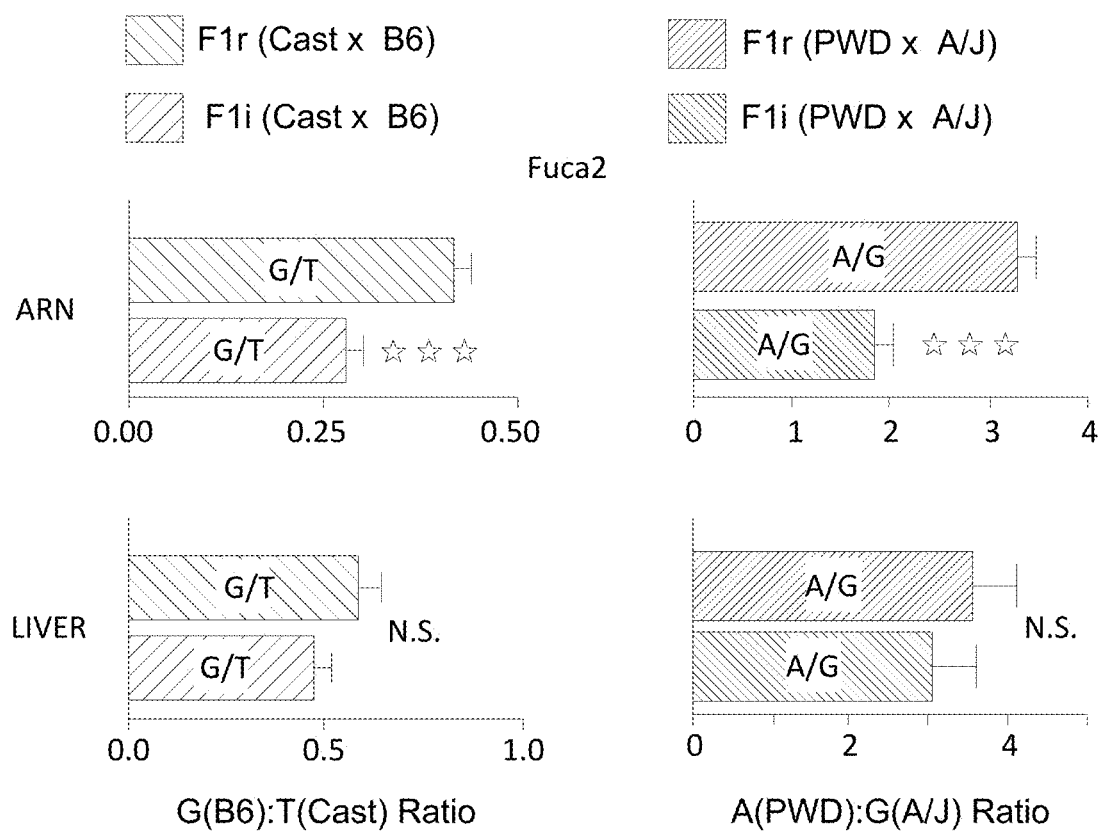

FIG. 5G is a bar graph showing that pyrosequencing validation for Fuca2 confirmed a maternal bias in the ARN, but not the liver, in Cast×B6 hybrid offspring and PWD/J× A/J hybrid offspring. Pyrosequencing primers targeted a G/T SNP in the B6:Cast allele expression analysis (bars on the left), and an A/G SNP site for the PWD/J:A/J allele expression analysis (bars on the right) (red, maternal allele; blue, paternal allele). The ratio for the expression of the G:T and A:G alleles was compared between the Fli and Flr crosses for Cast×B6 and PWD/J×A/J mice, respectively. A significant maternal bias was detected in the ARN, but not in the liver of both hybrid mouse strains.

Figure 5H:
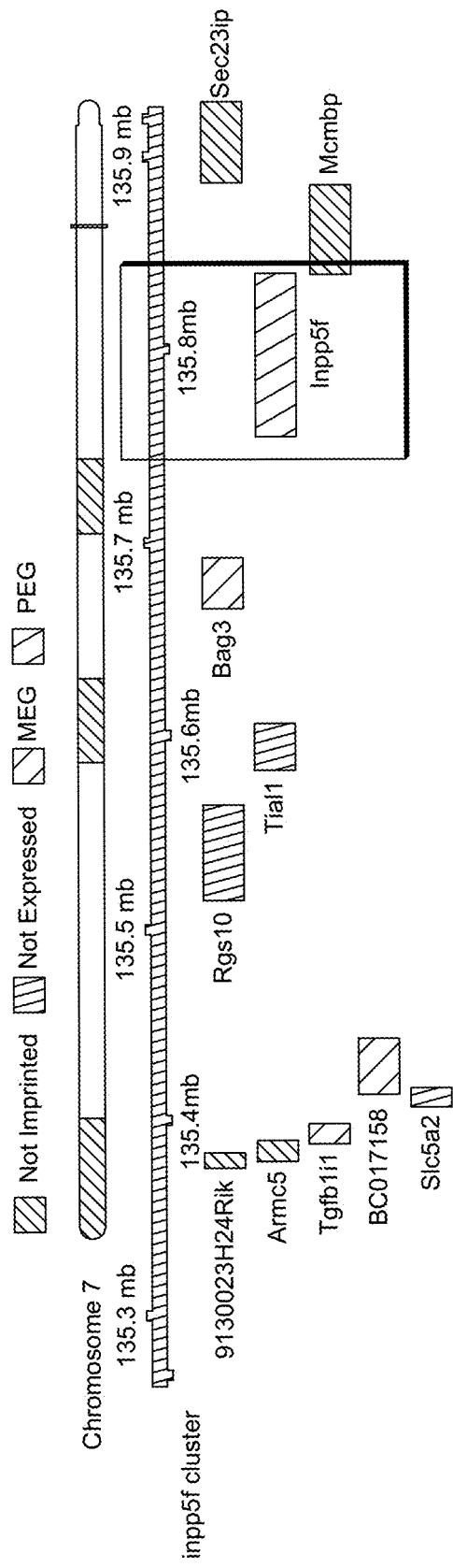
Figure 5I:
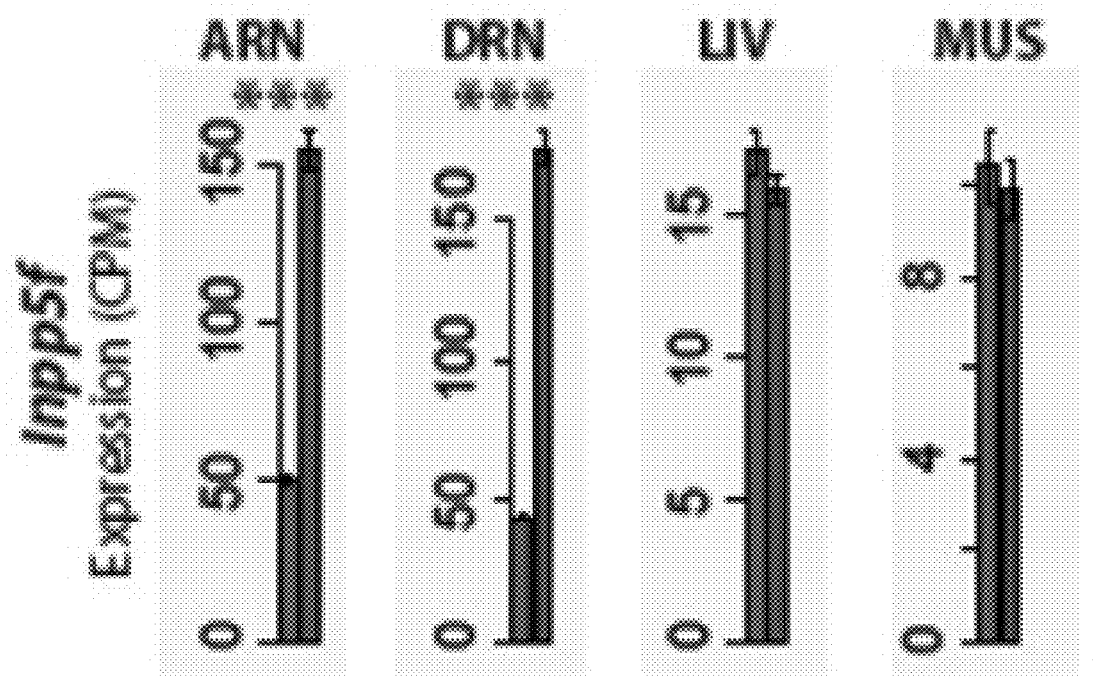
Figure 5J:
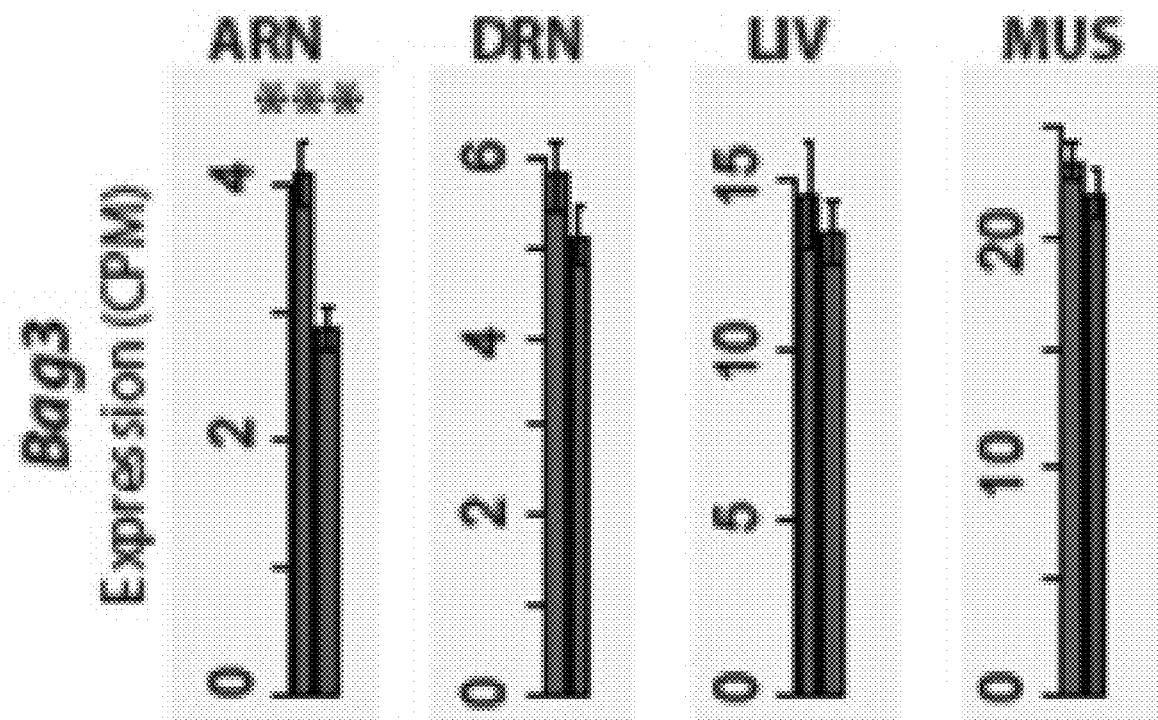
Figure 5K:
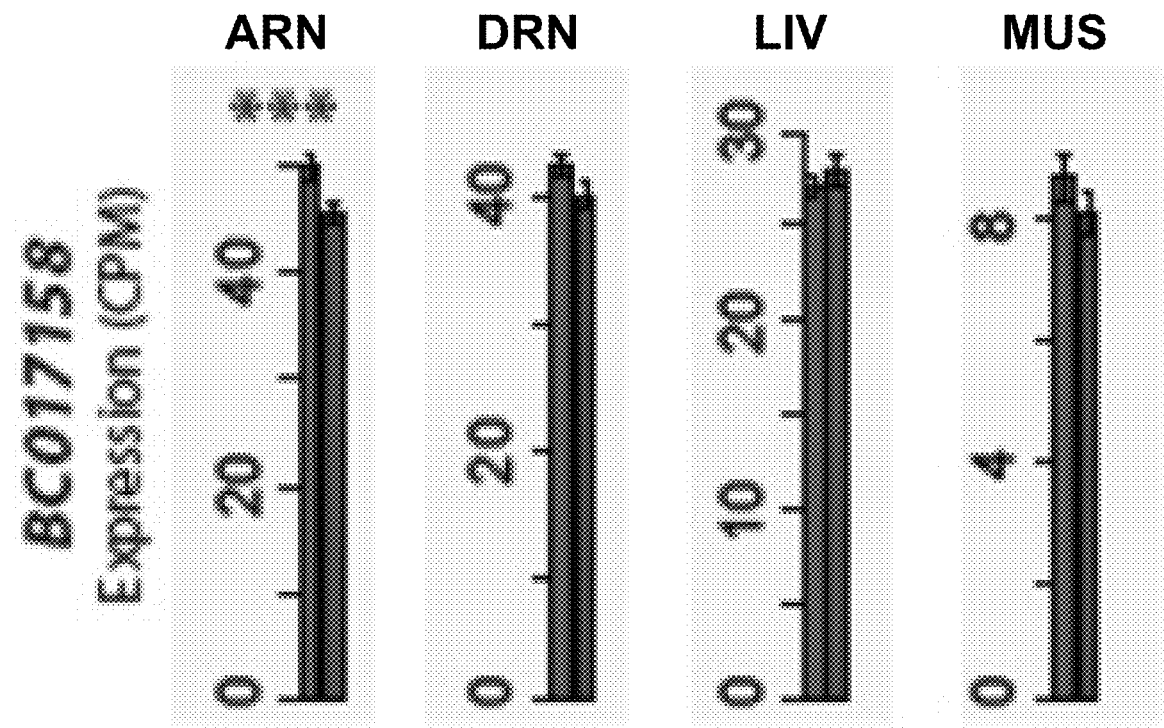
Figure 5L:
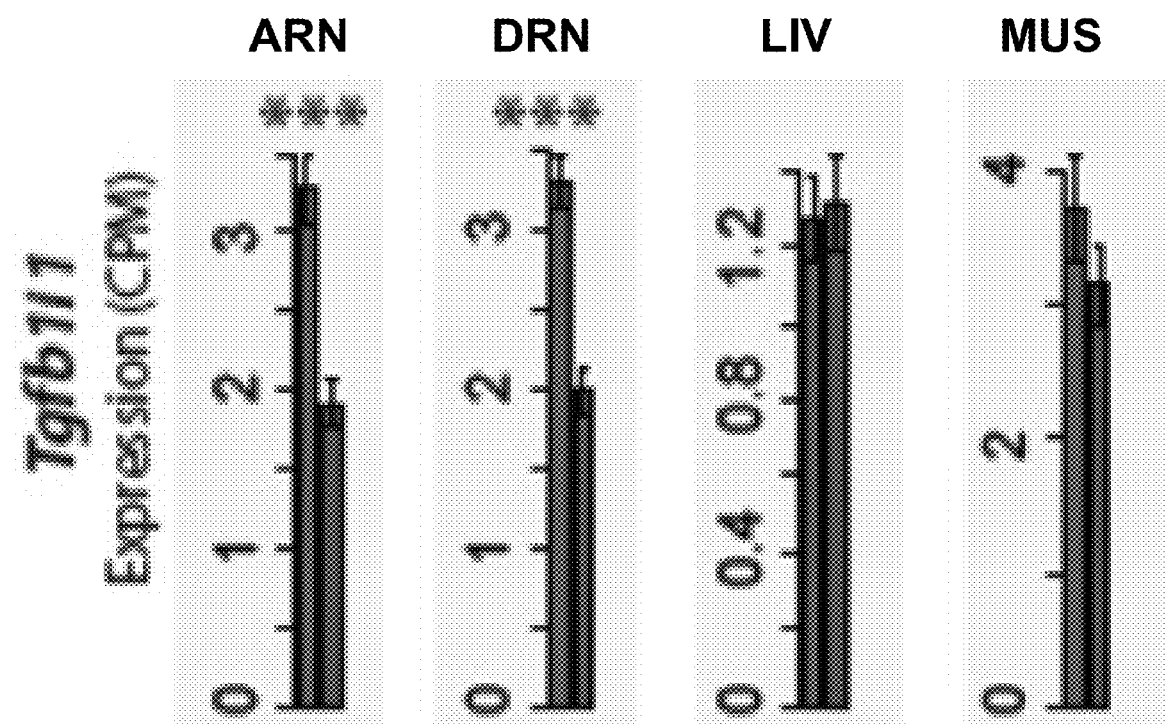

FIG. 5H is a schematic of the Inpp5f imprinted gene cluster on chromosome 7.

FIG. 5I to FIG. 5L are bar plots of the RNASeq results for imprinted genes indicating the mean expression levels of the maternal and paternal alleles across all biological replicates in the four tissue types. Inpp5f (B) exhibited a robust paternal bias in the ARN and DRN, but not the liver (LIV) or muscle (MUS). Bag3 (C) and BC017158 (D) exhibited a significant maternal bias in the ARN only, while Tgfb1i1 (E) exhibited a maternal bias in the ARN and DRN, but not the liver or muscle.

Figure 5M:
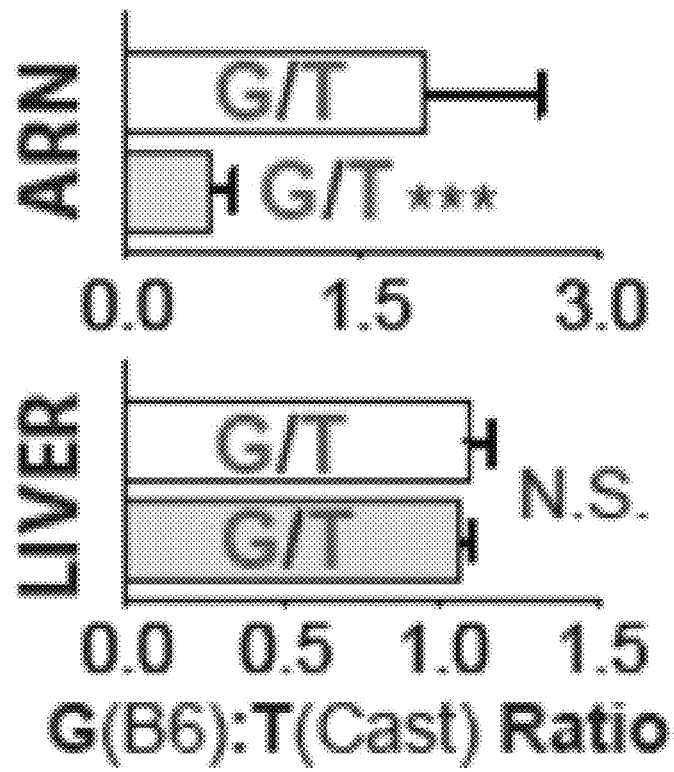
Figure 5N:
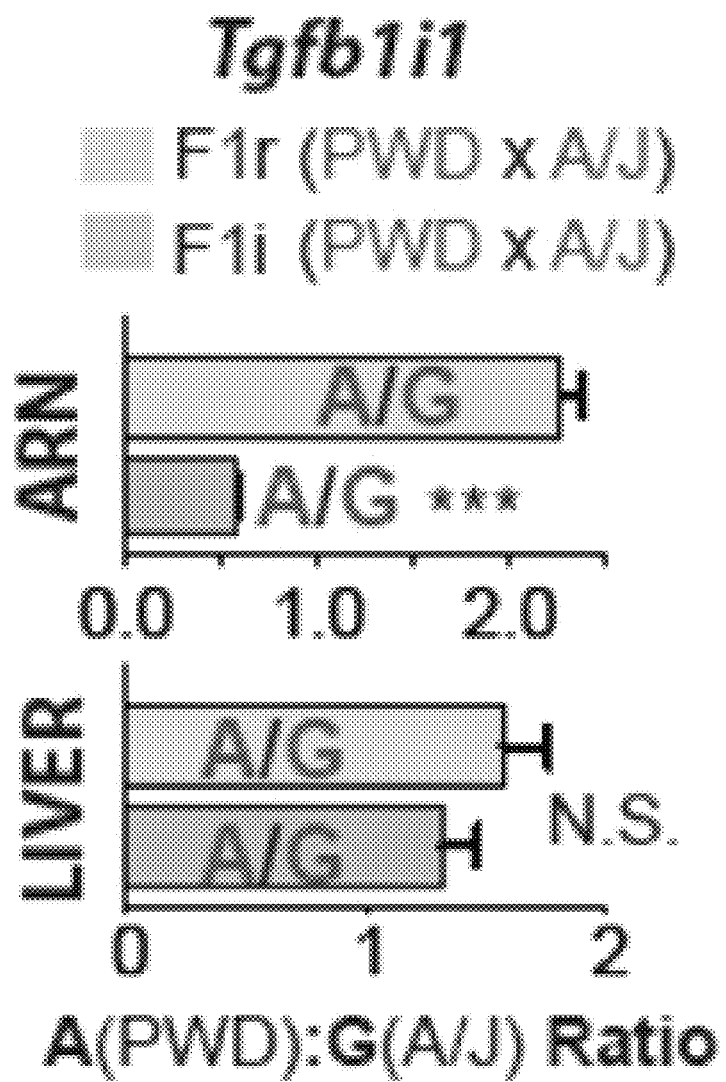

FIG. 5M to FIG. 5N are bar graphs showing pyrosequencing validation of the maternal bias for Tgfbli1 in the ARN, but not the liver, in Cast×B6 hybrid offspring (F) and PWD/J×A/J hybrid offspring (G). Pyrosequencing primers targeted a G/T SNP in the Tgfbli1 gene for the B6:Cast allele expression analysis (M) and an A/G SNP site for the PWD/J:A/J allele expression analysis (N) (red, maternal allele; blue, paternal allele). The ratio for the expression of the G:T and A:G alleles was compared between the Fli and Flr crosses for Cast×B6 and PWD/J×A/J mice, respectively. A significant maternal bias was detected in the ARN, but not the liver in both hybrid mouse strains.

FIG. 6A to FIG. 6H are bar graphs showing that RNASeq expression data revealed that Nhlrc1 (A and B) and Acrbp (C and D) exhibited a significant paternal allele expression bias in the ARN and DRN, but not the liver or muscle. Genes neighboring Nhlrc1 (A) or Acrbp (C) do not exhibit significant imprinting effects (vertical grey dashed line indicates the p value that yields a 5% FDR for the ARN as a reference). Gbp7 (E and F) and 6430548MO8Rik (G and H) exhibited noncanonical imprinting effects in the muscle. Neighboring genes did not exhibit significant imprinting effects.

Figure 7A:
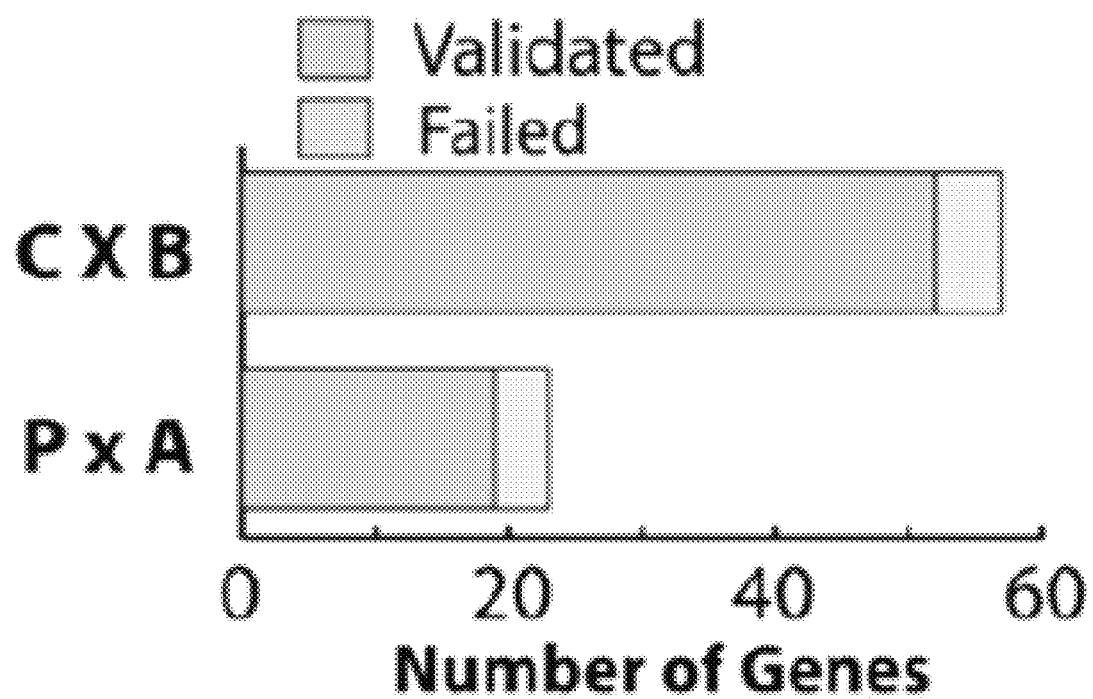

FIG. 7A is a bar graph showing the summary of pyrosequencing validation experiments in Cast×B6 (C×B) and PWD/J×A/J (P×A) hybrid offspring, which revealed high validation rates.

Figure 7B:
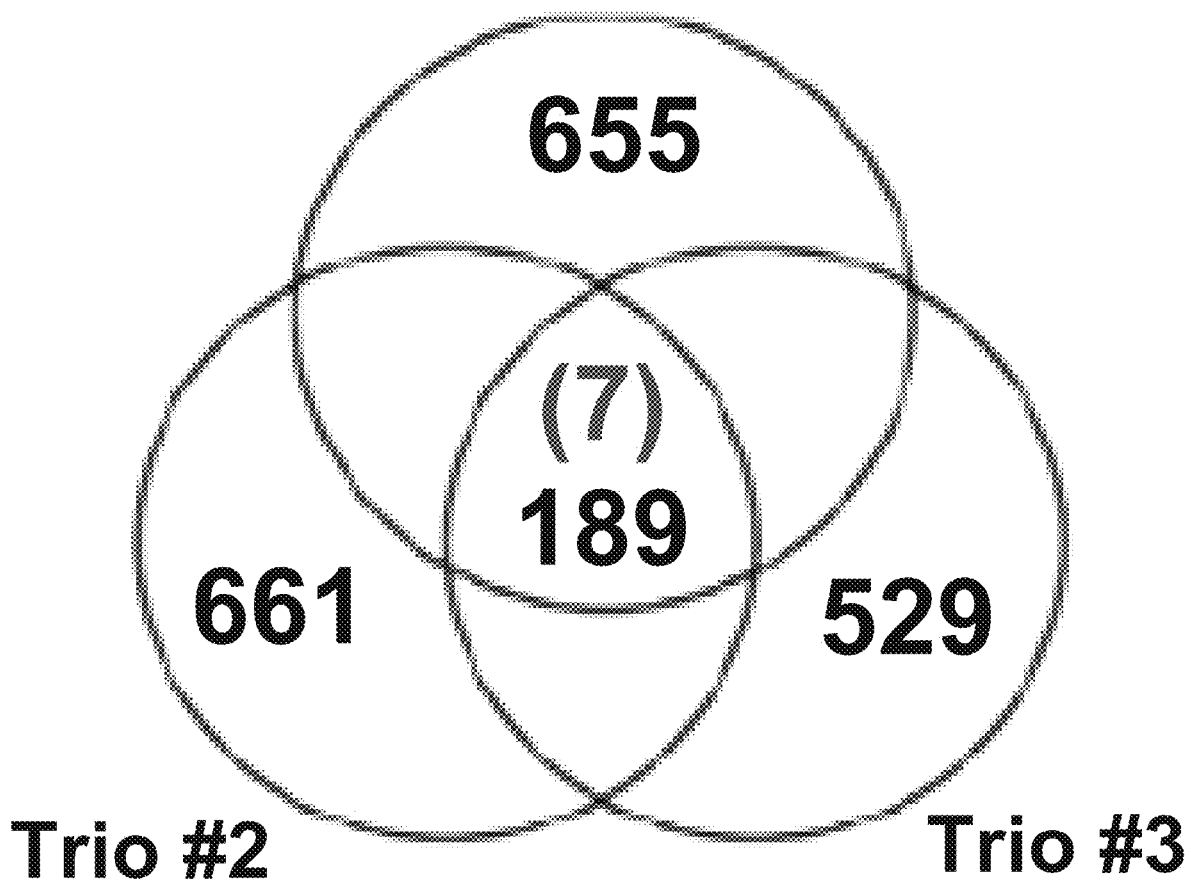

FIG. 7B is a Venn diagram of the number of expressed genes with SNPs for each wild-derived daughter. Out of the 189 SNP-containing genes shared between the trios, seven were imprinted genes identified in the ARN in hybrid mice.

Figure 7C:
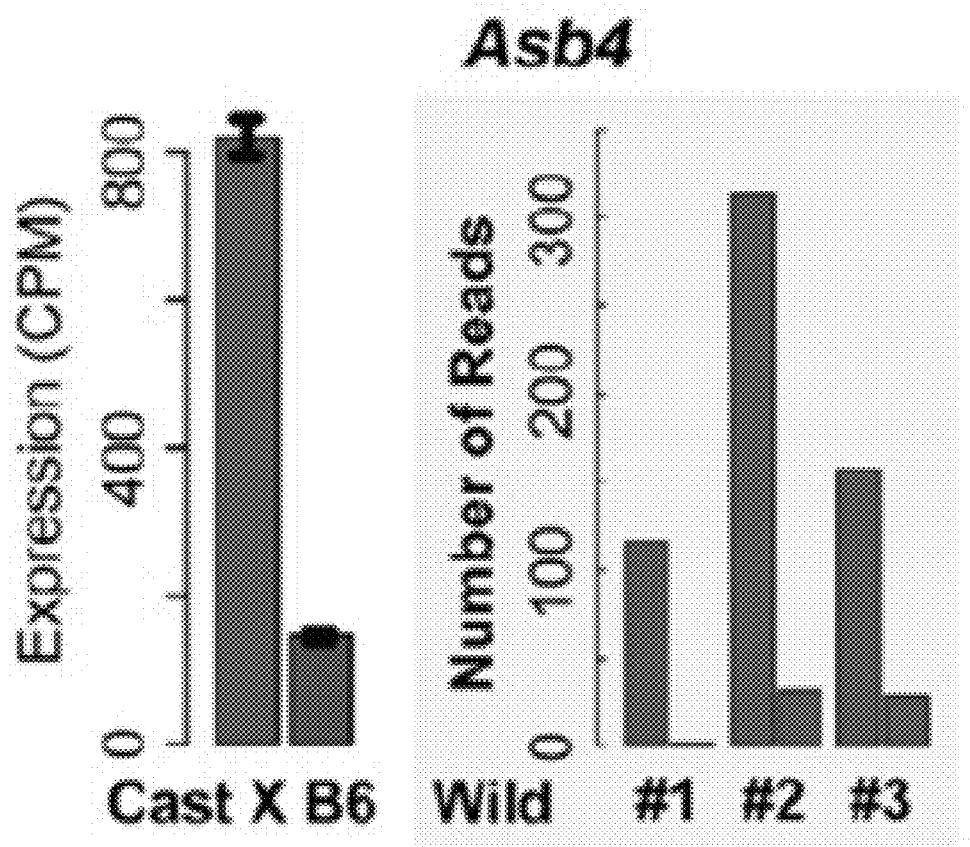
Figure 7D:
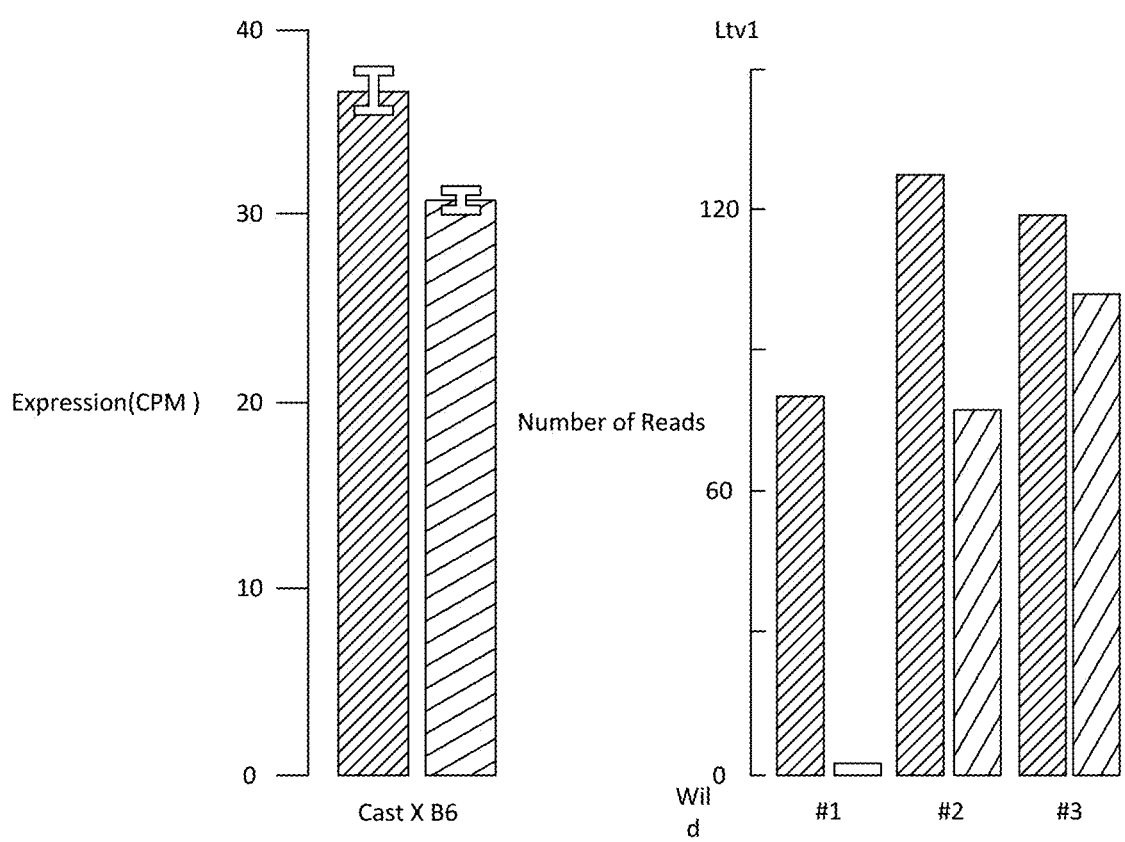
Figure 7E:
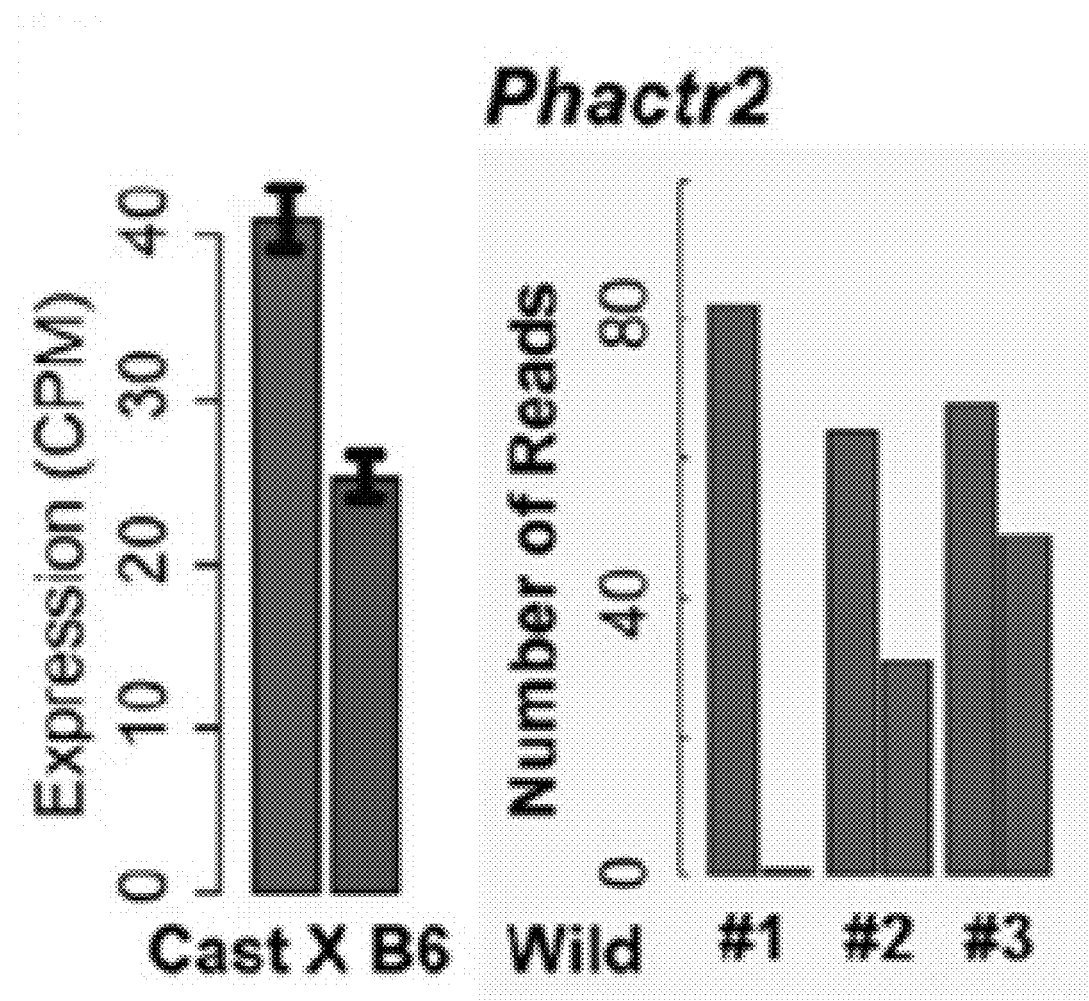

FIG. 7C to FIG. 7E are bar graphs showing that Asb4, Ltv1, and Phactr2 are noncanonical MEGs with biased expression of the maternal allele (left bars) relative to the paternal allele (right bars) in Cast×B6 hybrid mice as revealed by RNA-seq. A similar maternal bias was present in each of the wild-derived daughters (left bars) relative to the paternal allele (right bars).

Figure 7F:
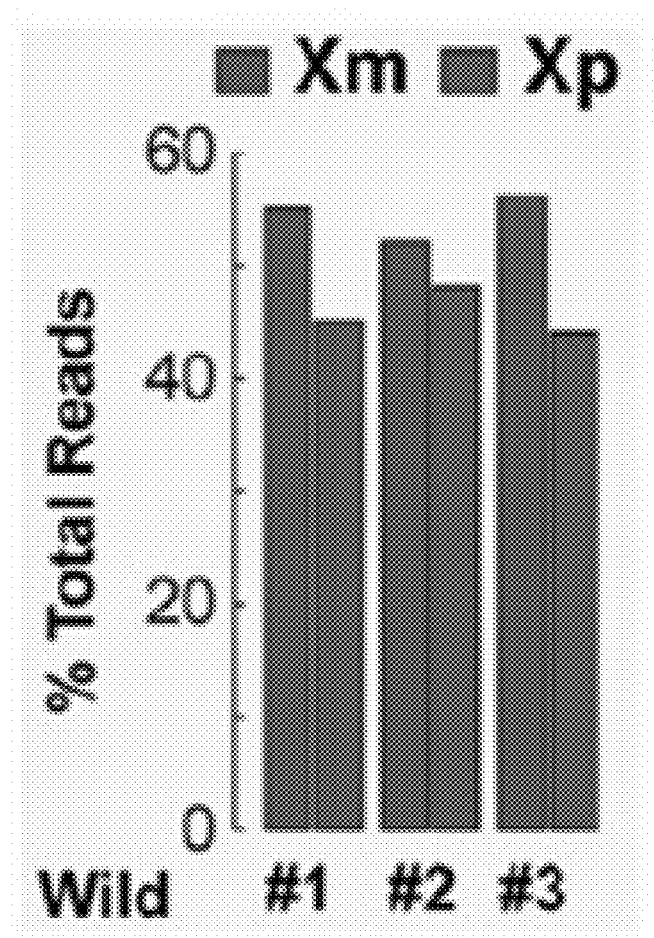

FIG. 7F is a bar graph showing the percentage of total reads derived from Xm versus Xp alleles in the wild-derived daughters revealed an Xm expression bias.

Figure 8A:
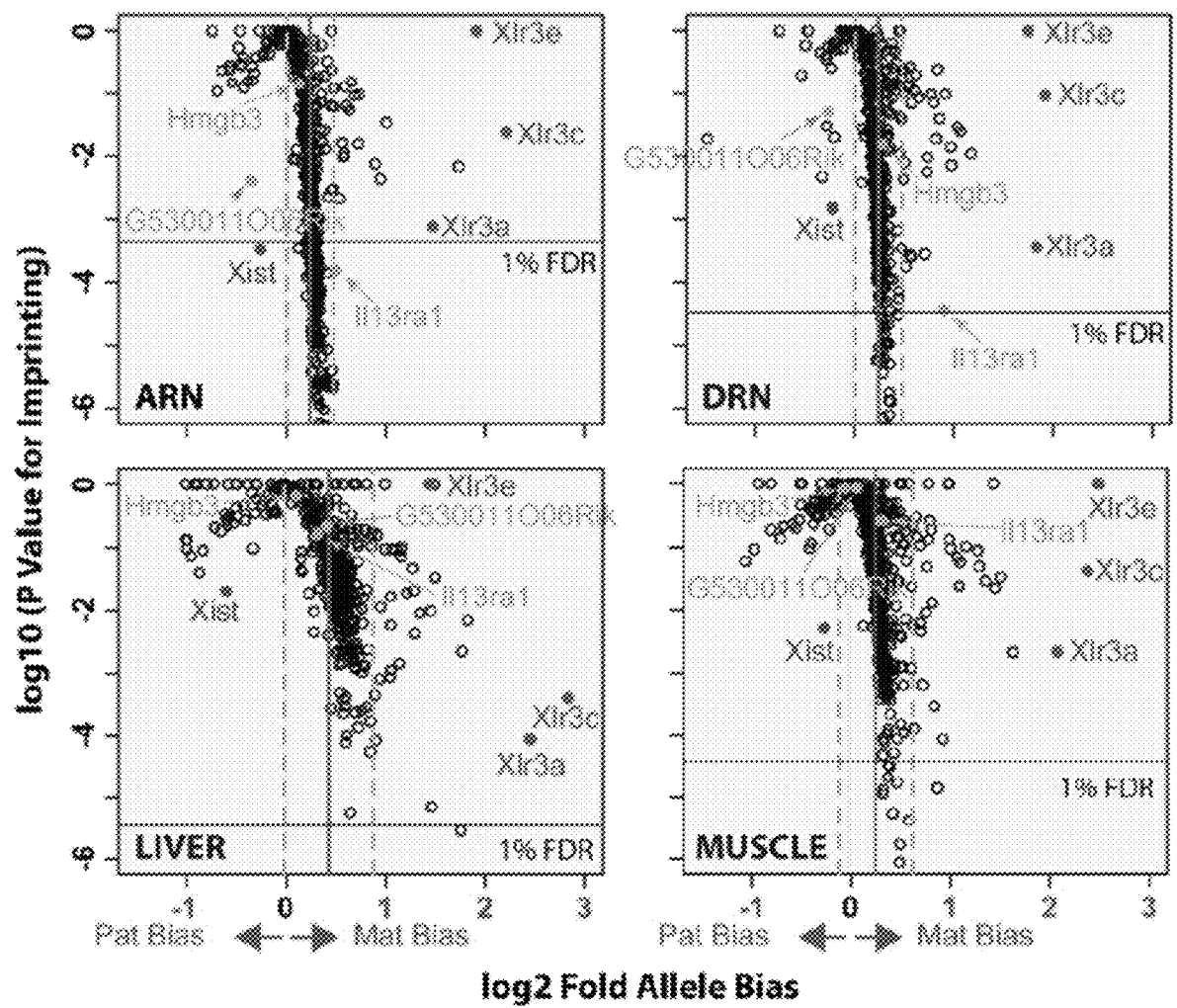

FIG. 8A is a scatterplot showing the paternal (left of dashed line) and maternal (right of dashed line) allele expression biases (log 2-fold bias) versus the p value (log 10) for imprinting effects for all X-linked genes. Most X-linked genes exhibited a maternal allele expression bias (mean allele bias is indicated by the solid vertical line; gray dashed lines indicate 1 standard deviation from this mean). The maternally biased Xlr genes are Xlr3a, Xlr3c, and Xlr3e. Examples of tissue-specific X-linked imprinting effects are indicated for the MEGs, Hmgb3 and Il13ra1, and the PEG, G530011O06Rik.

Figure 8B:
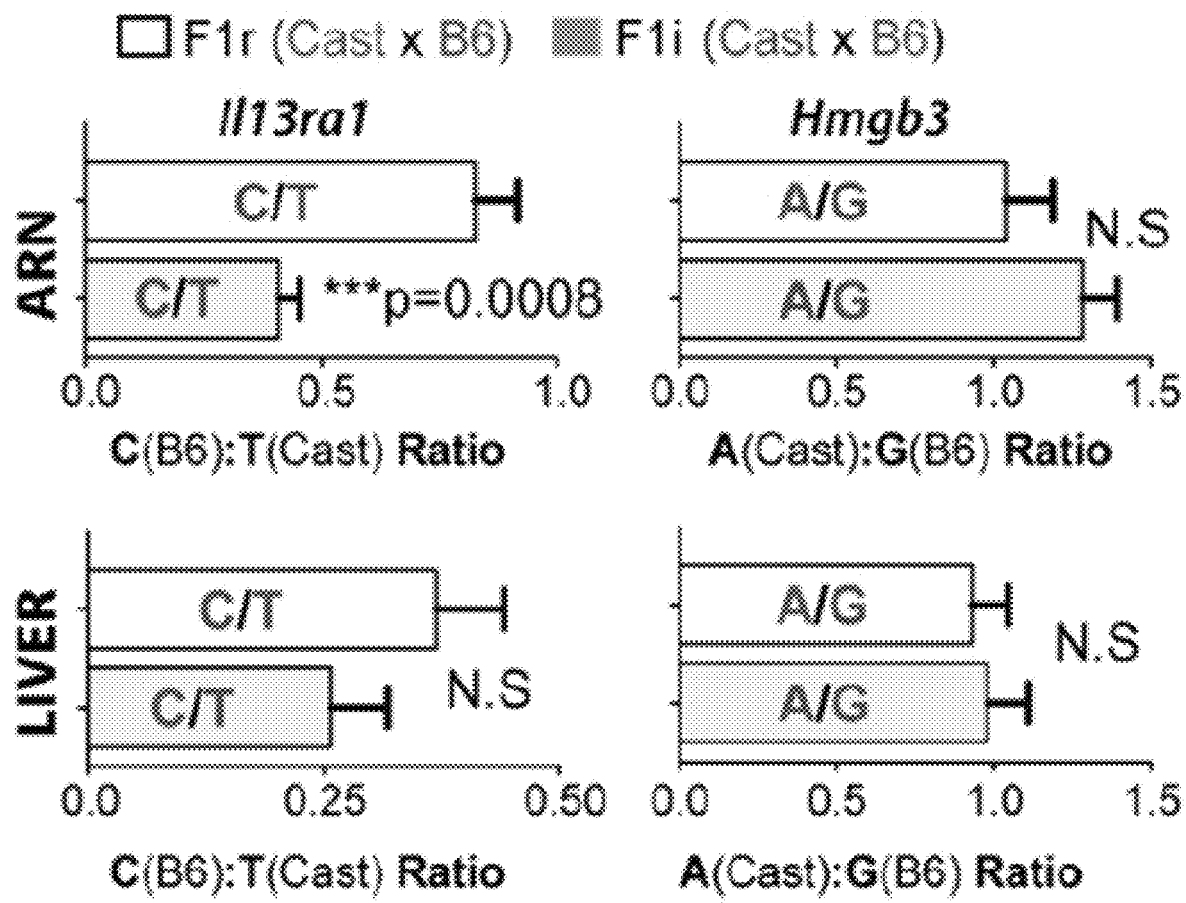
Figure 8C:
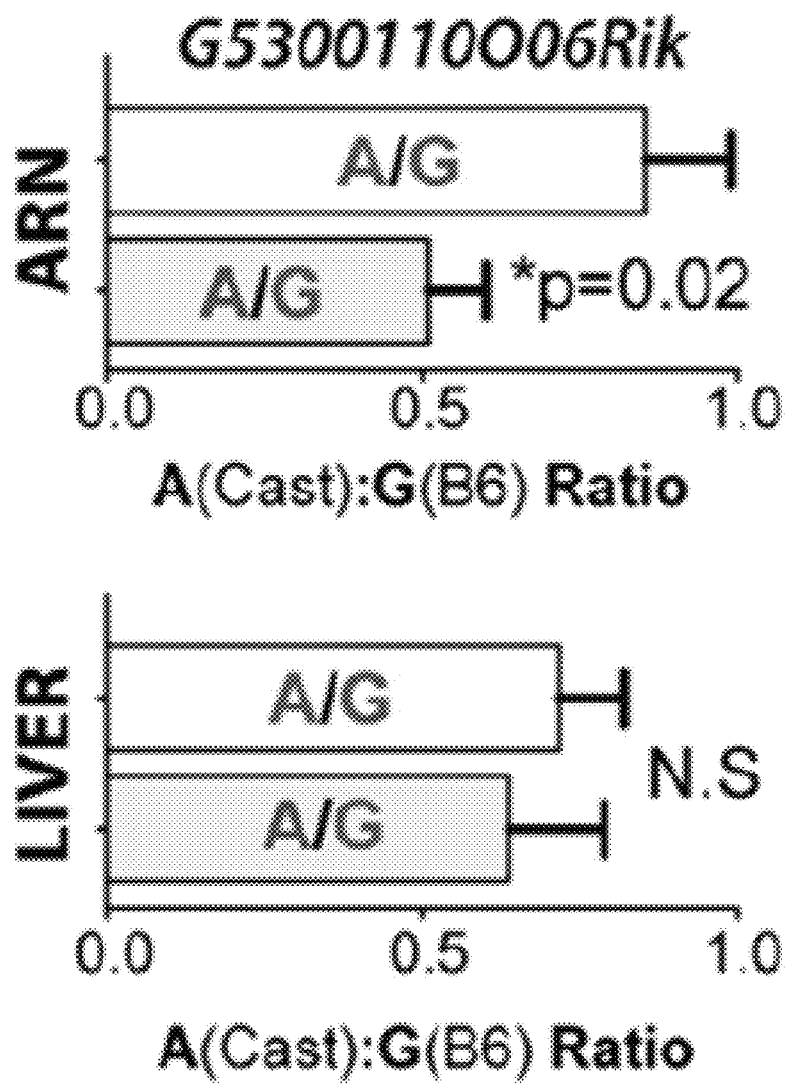

FIG. 8B and FIG. 8C are bar graphs showing pyrosequencing validations in Cast×B6 F1 hybrid offspring. Il13ra1 demonstrated a significant maternal bias in the ARN, but not the liver, and Hmgb3 did not exhibit a significant maternal bias in either tissue. G530011O06Rik exhibited a paternal bias in the ARN, but not the liver.

Figure 9A:
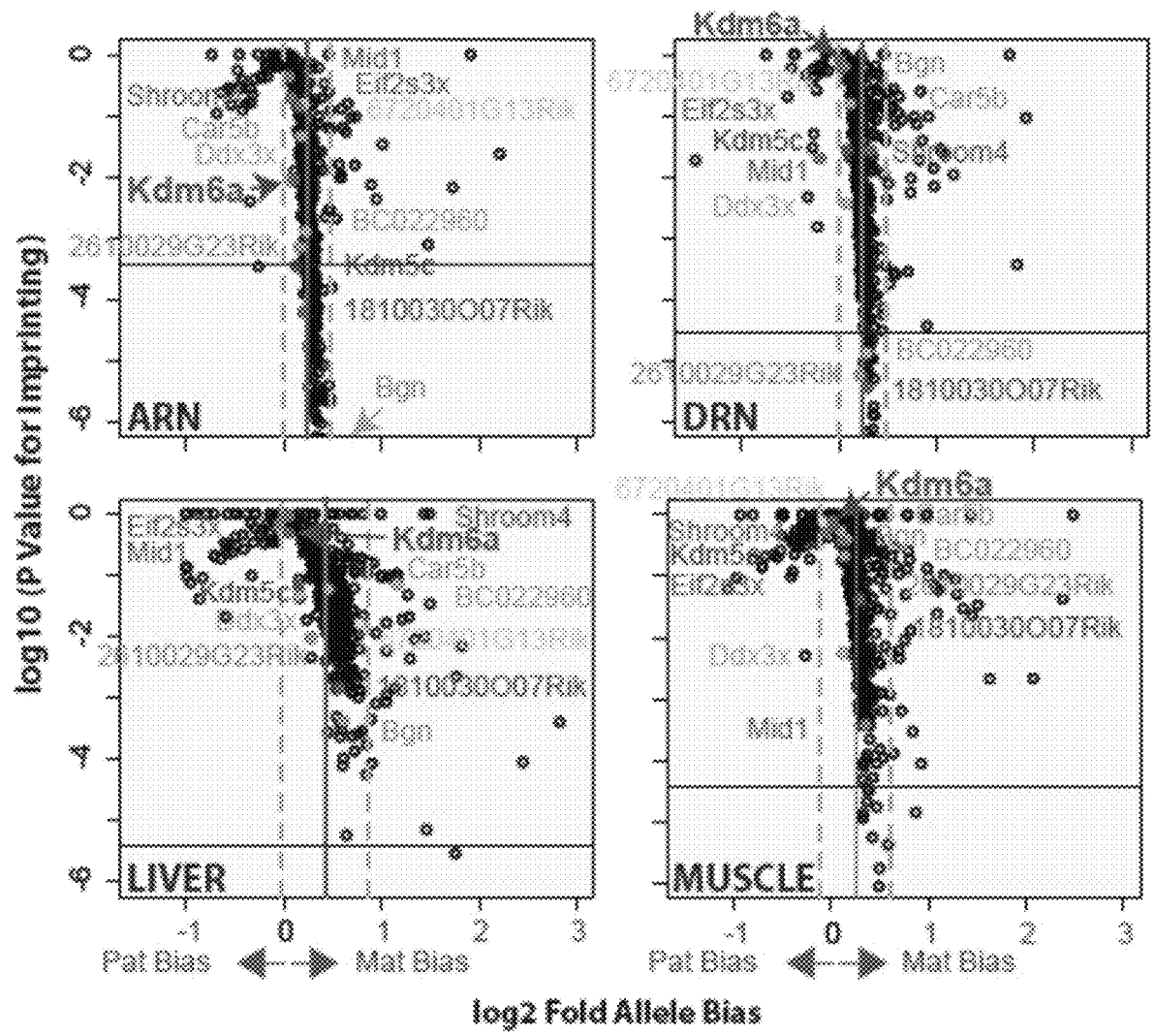

FIG. 9A is a scatterplot of paternal (left of solid vertical line) and maternal (right of solid vertical line) allele expression biases (log 2-fold bias) versus the p value (log 10) for imprinting effects for all X-linked genes in the ARN, DRN, liver, and muscle. Most X-linked genes exhibited a maternal allele expression bias in each tissue, but the robustness of these effects are highly gene and tissue specific. The mean allele bias is indicated by the center line, and grey dashed lines indicate one standard deviation from this mean. Genes known to escape X-inactivation are indicated by colored dots. Some genes that escape X-inactivation exhibited evidence for tissue-specific imprinting, such as Kdm6a, which exhibited a trend for imprinting in the ARN, but not the DRN, liver, or muscle. The horizontal line indicates 1% FDR cutoff. Bgn exhibited a highly significant imprinting effect in the ARN and is off the scale of the graph.

Figure 9B:
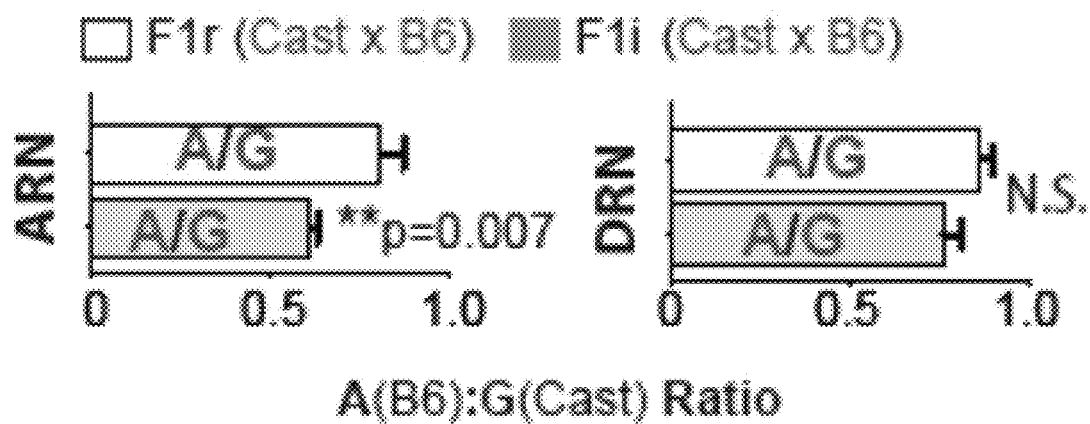
Figure 9C:
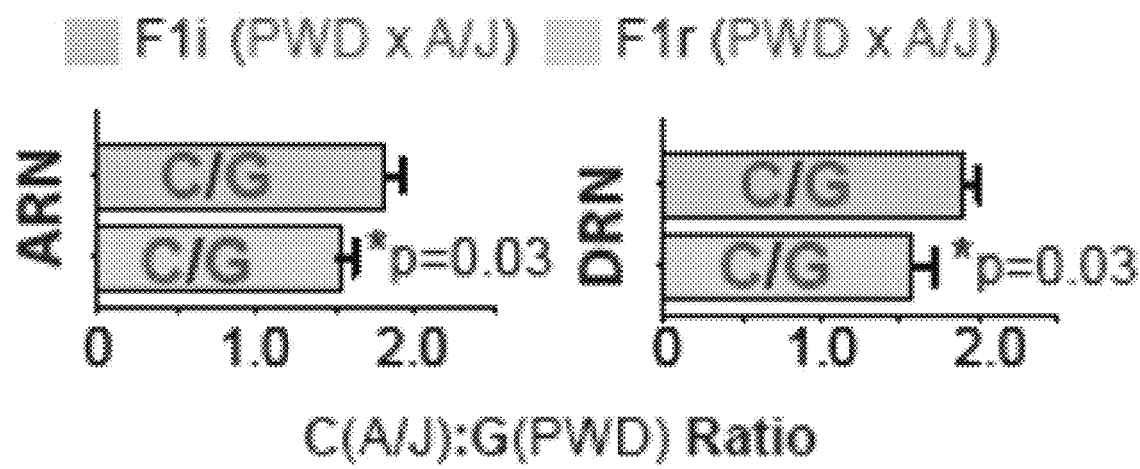

FIG. 9B and FIG. 9C are bar graphs showing that pyrosequencing validations for Kdm6a in Cast×B6 F1 hybrid offspring revealed a significant maternal bias in the ARN, but not the DRN, consistent with the RNASeq data. Pyrosequencing in PWD×A/J hybrids revealed a significant maternal bias in both the ARN and DRN.

Figure 9D:
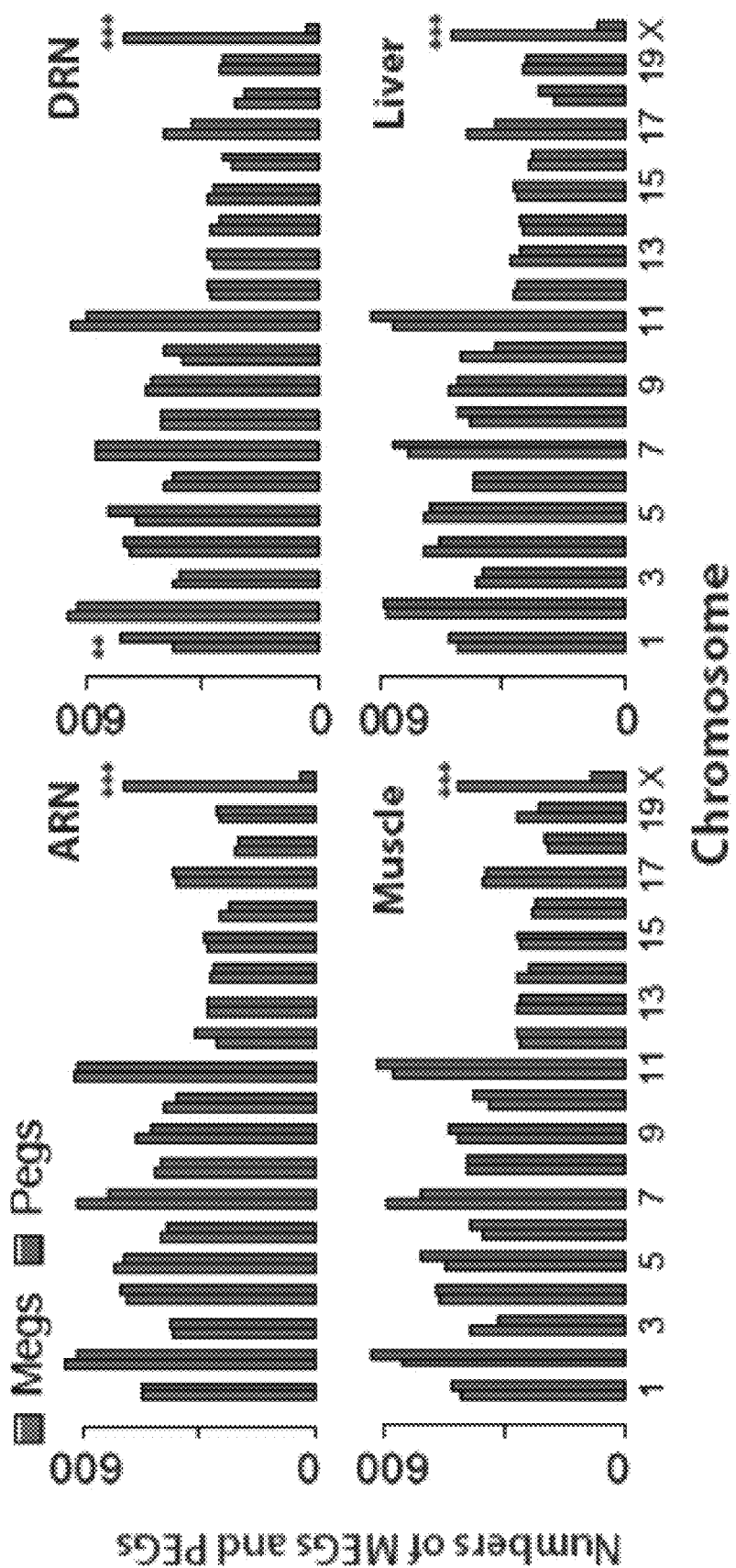

FIG. 9D is a bar graph which compares the total number of MEGs and PEGs on each chromosome independent of a statistical cutoff in the ARN, DRN, liver, and muscle. A significant paternal bias was observed on chromosome 1 in the DRN and a maternal bias is observed on the X chromosome in all tissues.

Figure 10A:
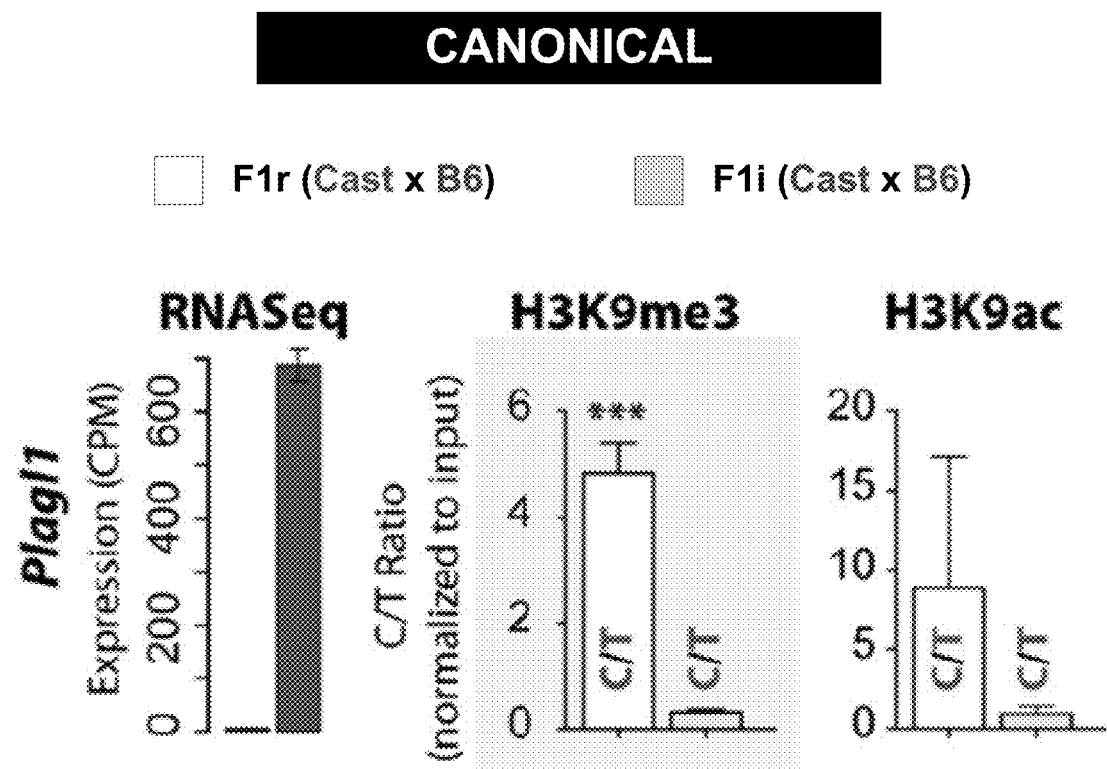
Figure 10B:
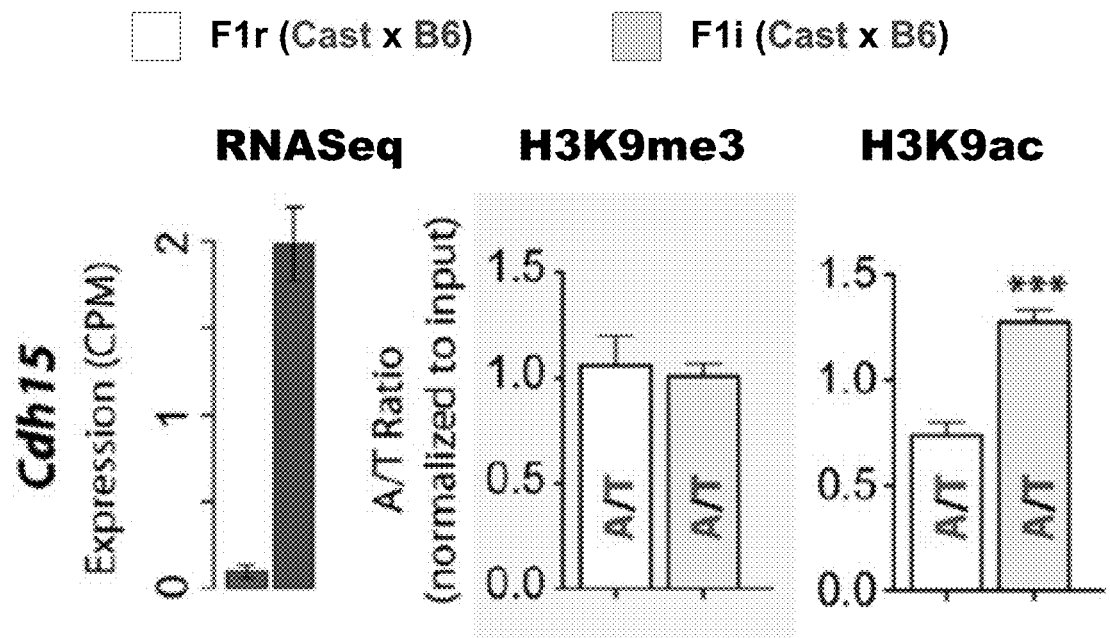

FIG. 10A and FIG. 10B are bar graphs of RNA-seq data indicating that Plagl1 (A) and Cdh15 (B) are canonical PEGs in the ARN. ChIP-pryo analysis in Cast×B6 hybrid mice targeting SNPs sites in the promoter region for Plagl1 revealed a significant enrichment for H3K9me3 on the repressed maternal allele and no significant enrichment for H3K9ac on either allele. In contrast, Cdh15 exhibited a significant enrichment for H3K9ac on the expressed paternal allele and no significant enrichment for H3K9me3 on the repressed maternal allele. Enrichments were normalized to input controls.

Figure 10C:
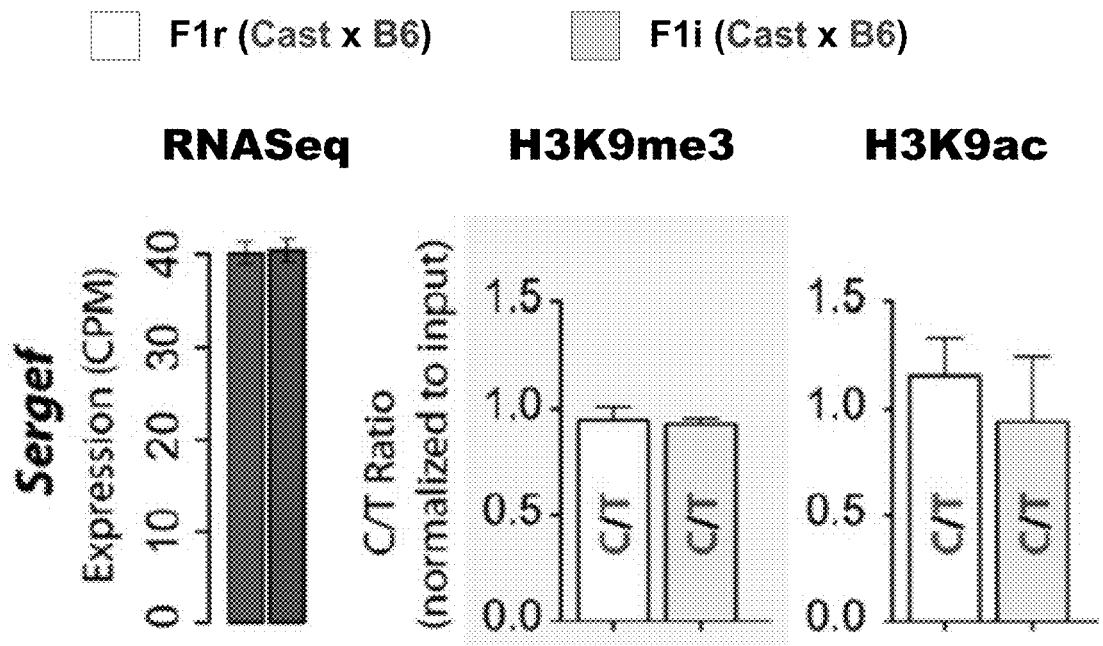

FIG. 10C is a bar graph showing that Sergef is a negative control gene that does not exhibit imprinting and does not exhibit maternal or paternal allele-specific enrichments for H3K9me3 or H3K9ac.

Figure 10D:
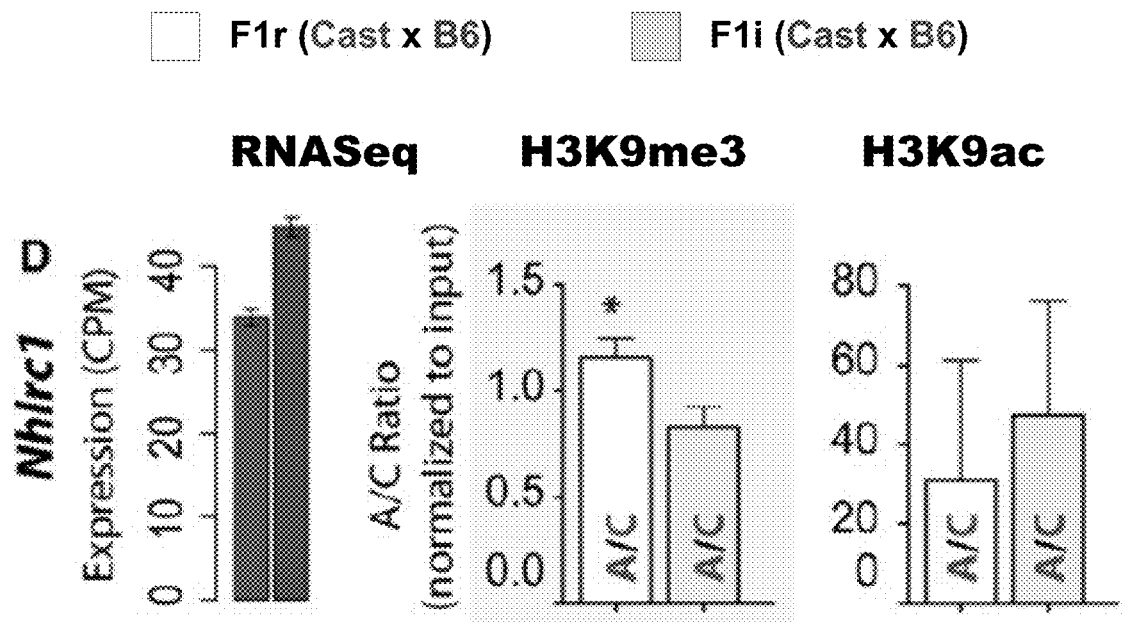

FIG. 10D is a bar graph showing that Nhlrc1, a remote noncanonical PEG, revealed enriched H3K9me3 on the partially repressed maternal allele and no enrichment for H3K9ac on either allele.

Figure 10E:
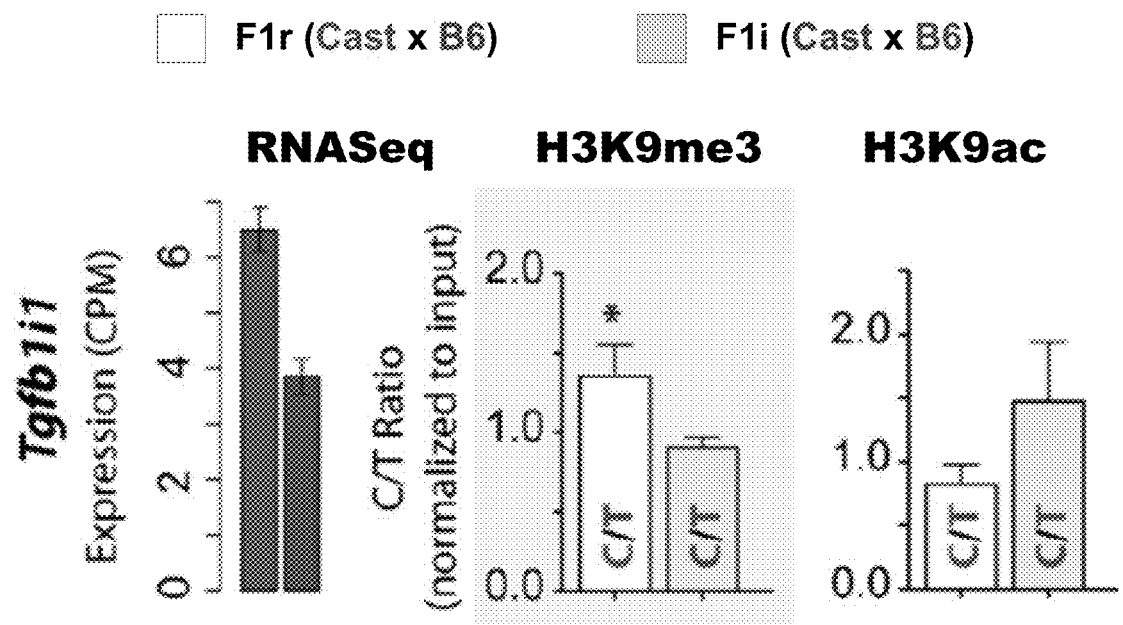

FIG. 10E is a bar graph showing that Tgfbli1, a clustered noncanonical MEG, revealed a significant enrichment for H3K9me3 on the repressed paternal allele and no significant enrichment for H3K9ac on either allele.

FIG. 11A to FIG. 11D are models of noncanonical imprinting effects at the cellular level.

Figure 11A:
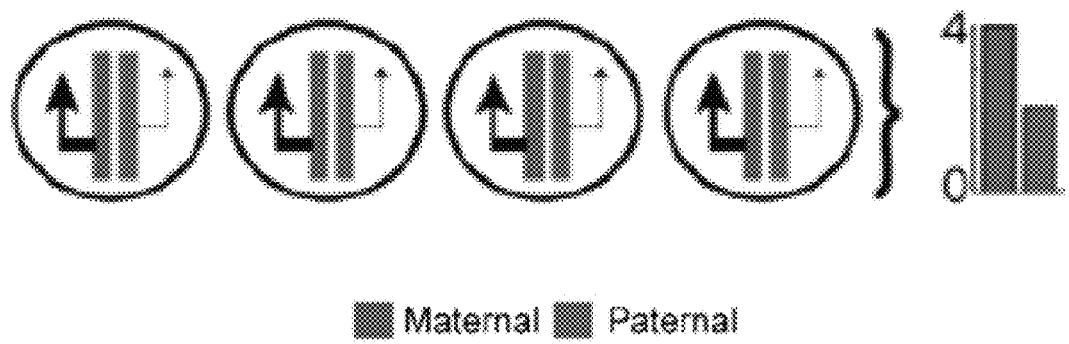
Figure 11B:
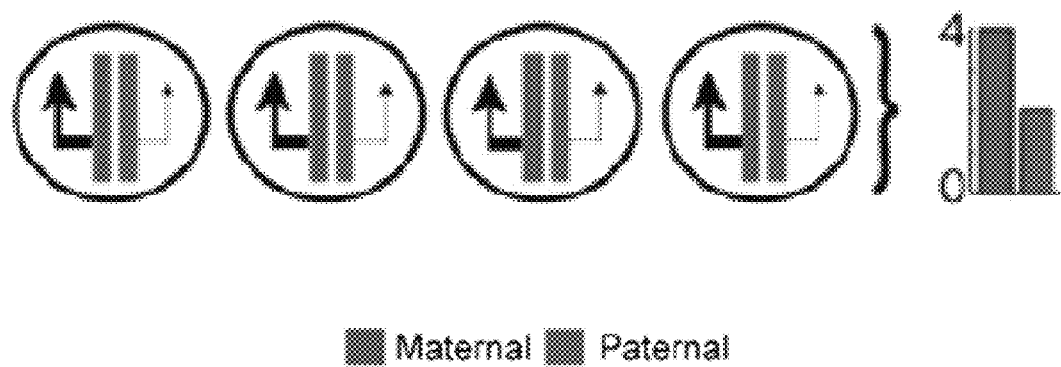
Figure 11C:
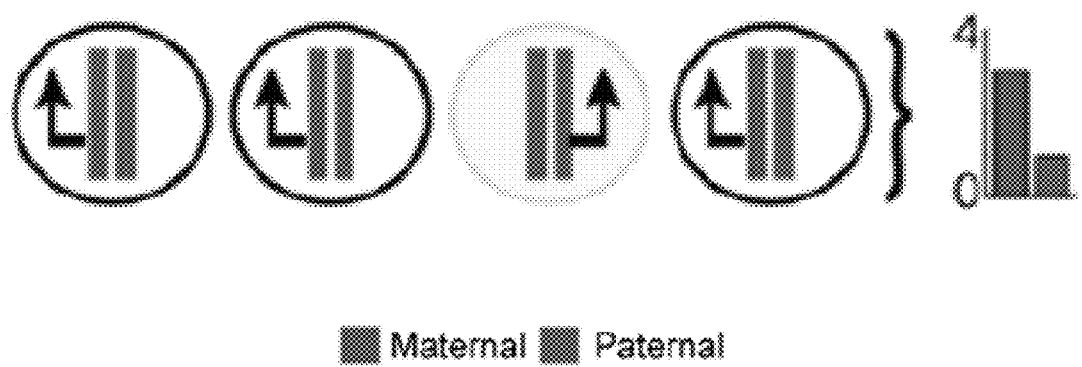
Figure 11D:
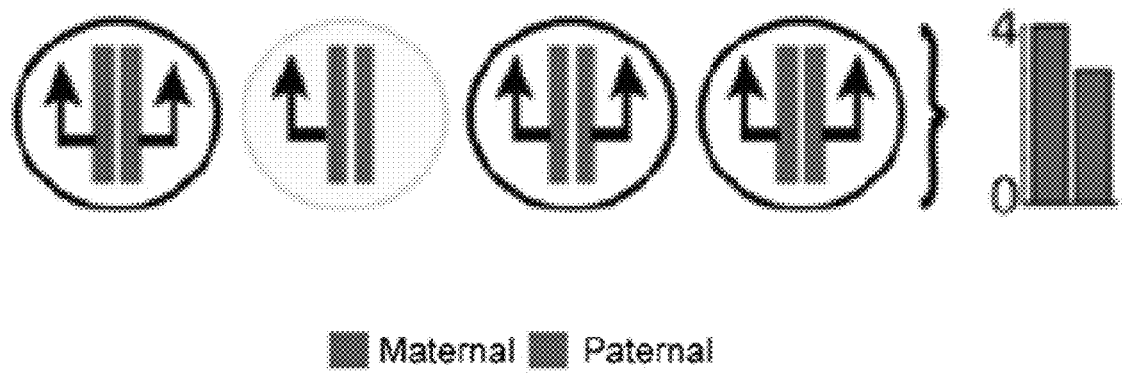
Figure 11E:
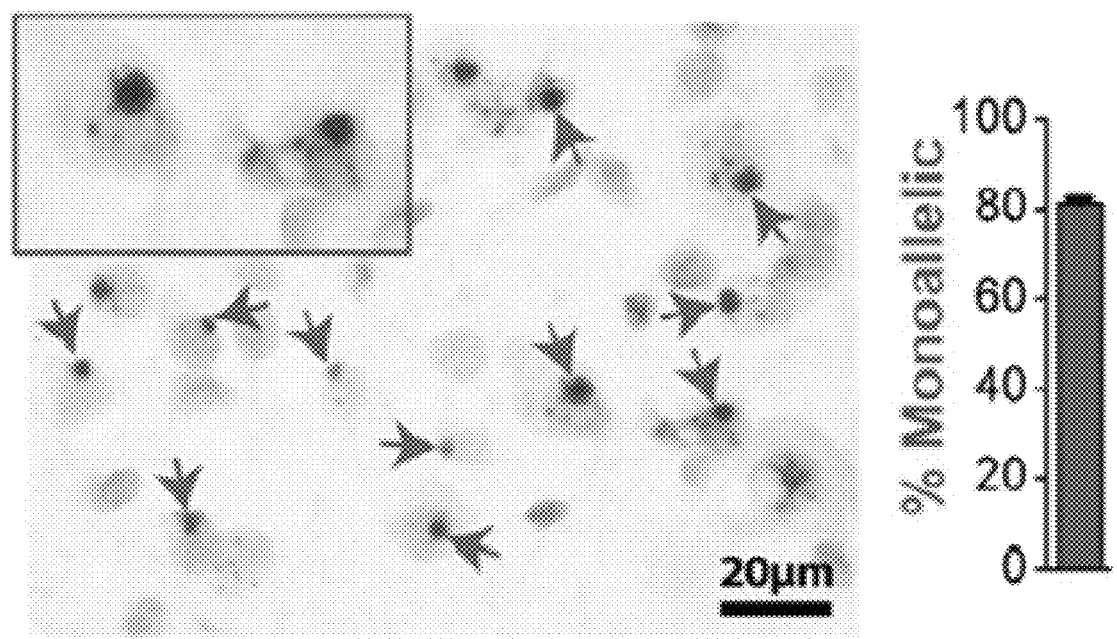

FIG. 11E is an image showing an intronic probe targeting nascent RNA for Meg3 (canonical imprinted) revealed monoallelic expression in cells of the DRN (arrows). Hematoxylin nuclear counterstaining revealed nuclei in cryosections. The proportion of monoallelic cells is indicated in the bar graph.

Figure 11F:
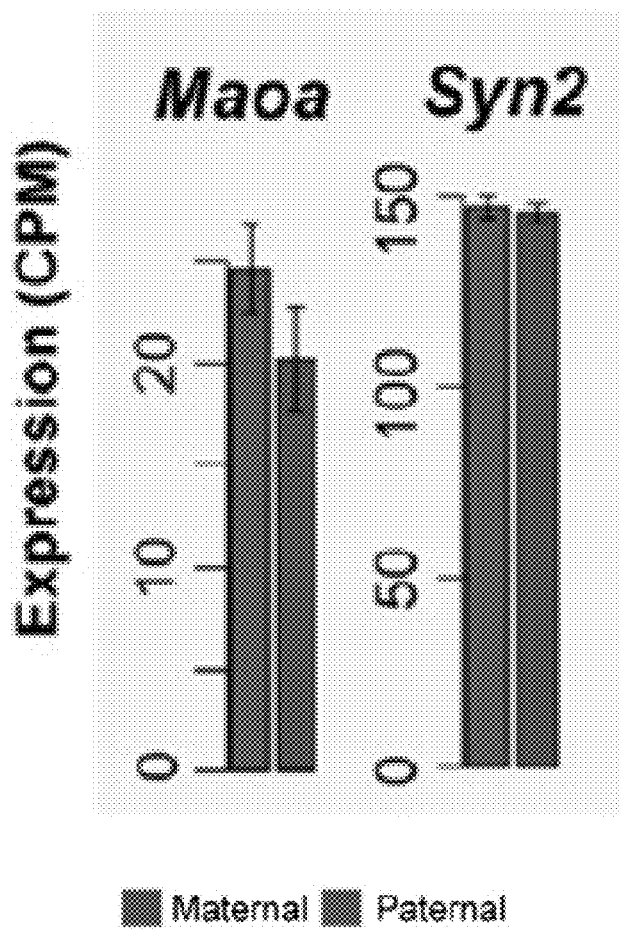
Figure 11G:
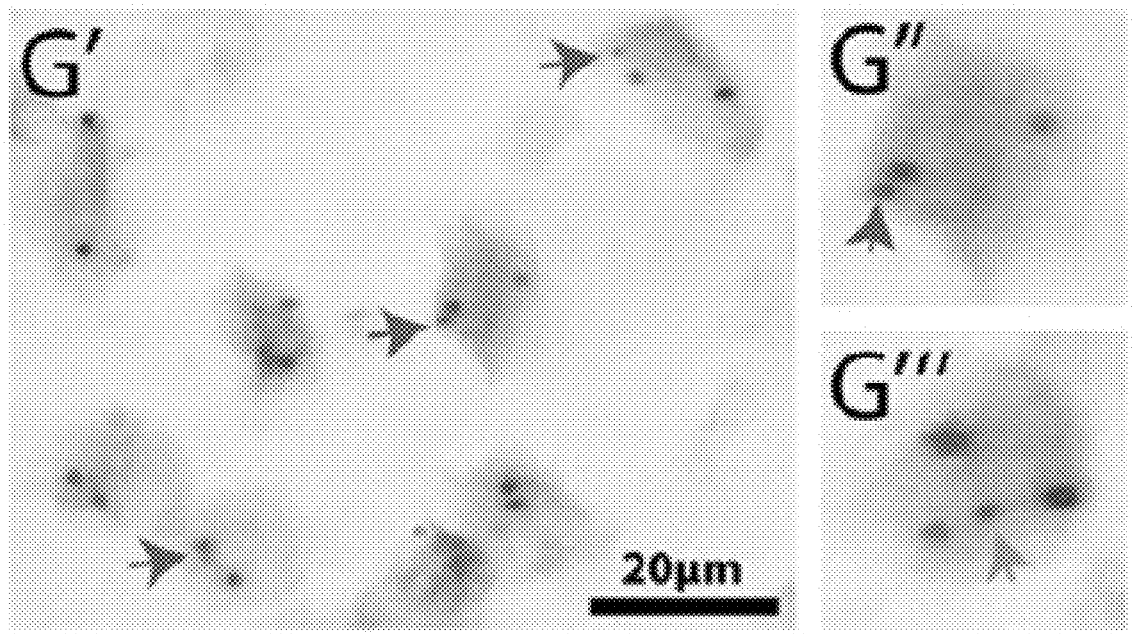
Figure 11H:
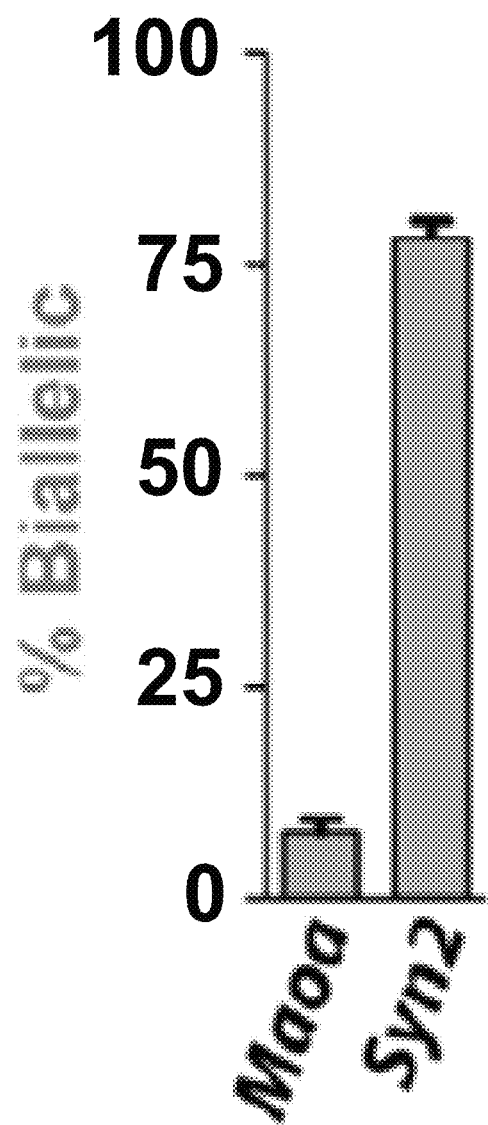

FIG. 11F to FIG. 11H are bar graphs and images showing that RNA-seq revealed maternal bias for the X-linked gene, Maoa, and equal expression of the maternal and paternal alleles for Syn2 (autosomal, ARN data shown). Nascent RNA in situ (right bars) in the ARN reveals largely monoallelic (G' and G'', arrows) and very few biallelic (G''', arrow)Maod cells. In contrast, Syn2 expresses both alleles in most positive cells. The bar graph indicates the percentage of Maoa+ and Syn2+ cells that are biallelic.

FIG. 11I to FIG. 11Q are bar graphs and images showing that RNA-seq revealed maternal and paternal allele expression for Ago2 (I), Ahi1 (L), and Igf2r (O). Intronic probes revealed subpopulations of biallelic (orange arrows) and monoallelic (green arrows) cells in the ARN for Ago2 (J), Ahi1 (M), and Igf2r (P). Bar plots indicate the percentage of monoallelic cells out of the total positive cells in the ARN and DRN.

Figure 12A:
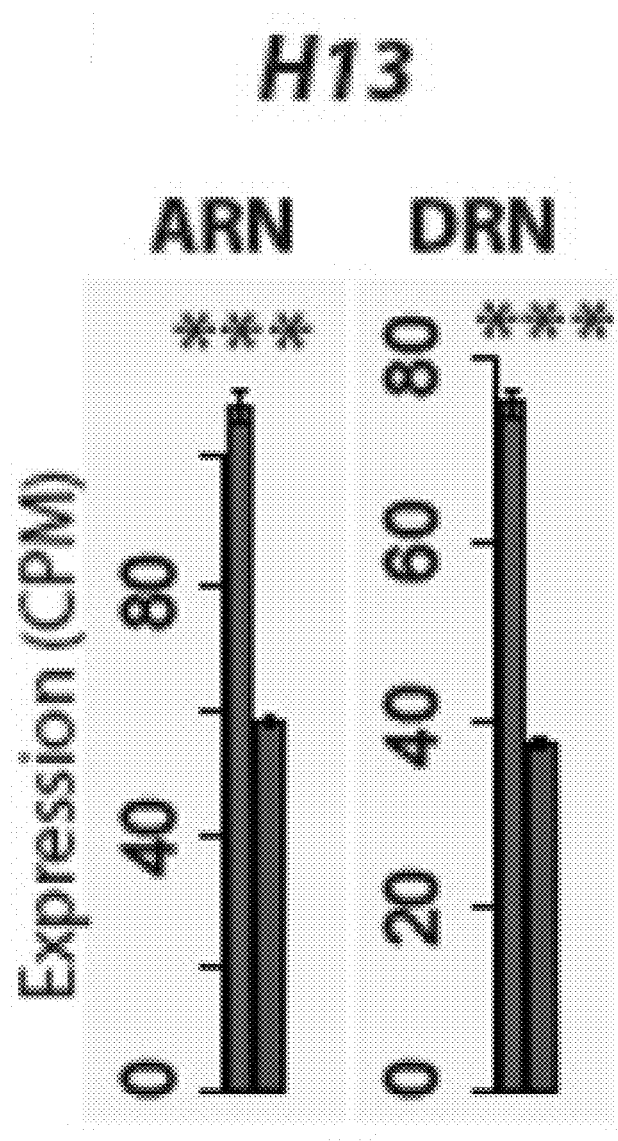

FIG. 12A is a bar plot of the RNASeq data for H13 in the ARN and DRN which demonstrated that a maternal bias existed at the gene level.

Figure 12B:
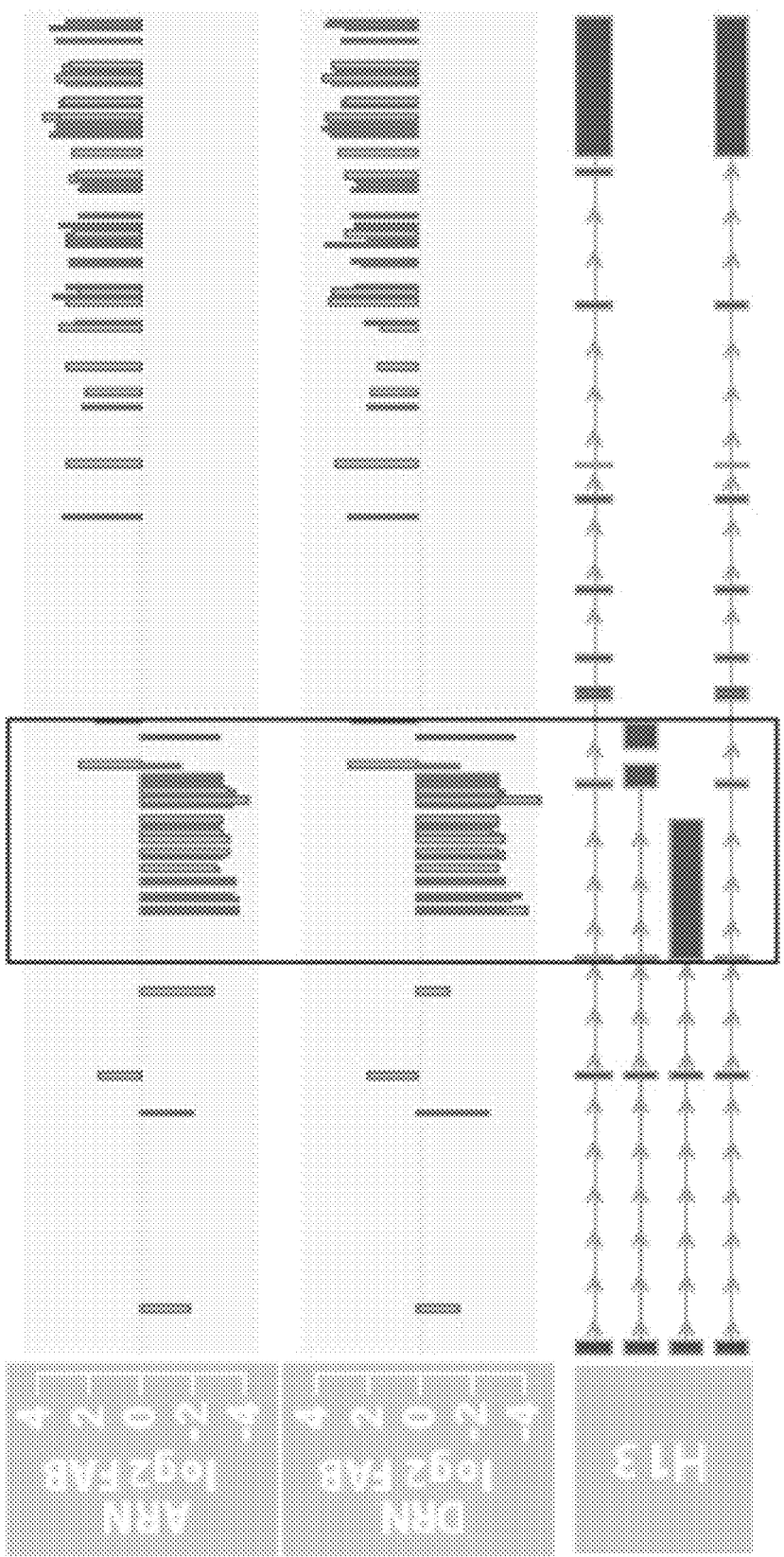

FIG. 12B is a plot of the log 2 fold allele bias (FAB) at the level of individual SNPs (maternal, pink and positive log 2 FAB; paternal, blue and negative log 2 FAB) revealed the existence of distinct maternal and paternal transcripts at the H13 locus. The long H13 transcripts were associated with maternally biased SNP sites and the short transcripts are associated with paternally biased SNP sites.

Figure 12C:
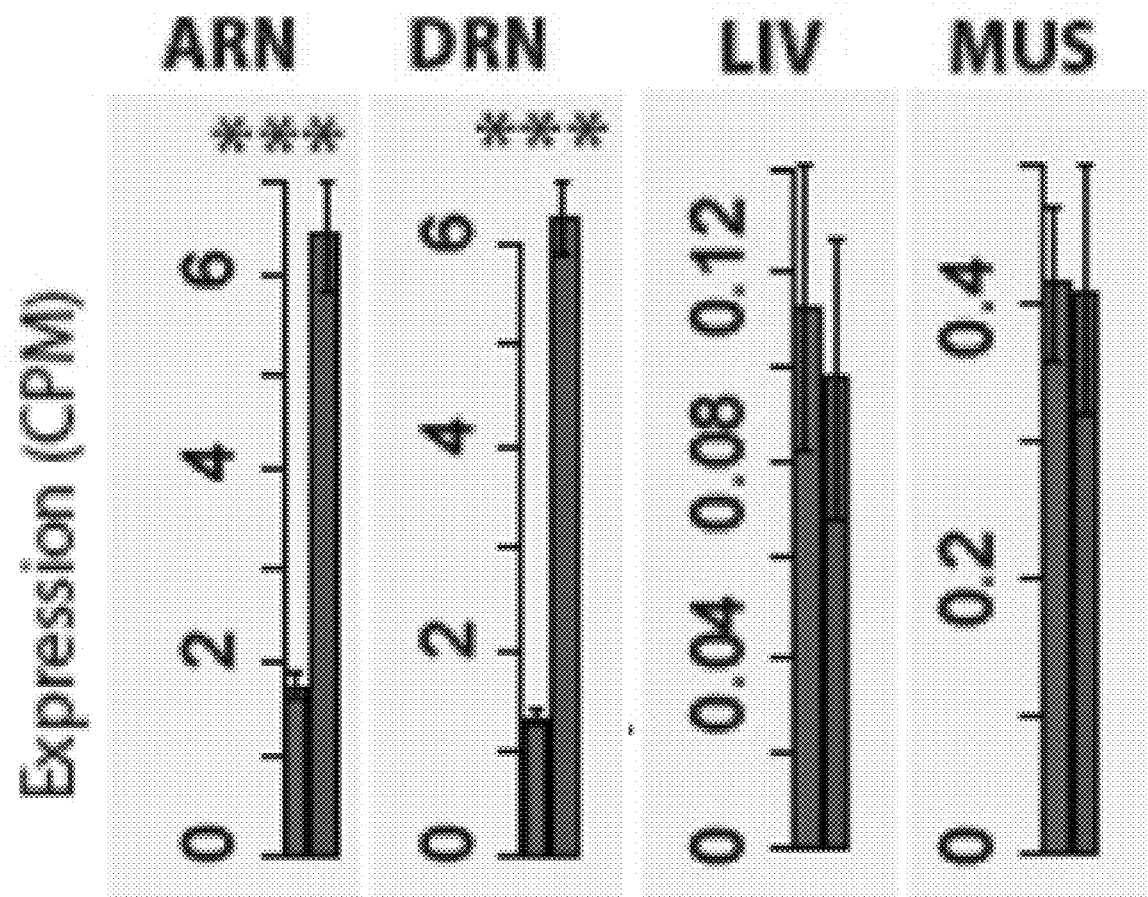

FIG. 12C is a bar plot of the RNASeq data for Gnas in the ARN, DRN, liver, and muscle that demonstrated that a paternal bias exists at the gene level in the brain, but not the liver or muscle, and expression was low in these tissues.

Figure 12D:
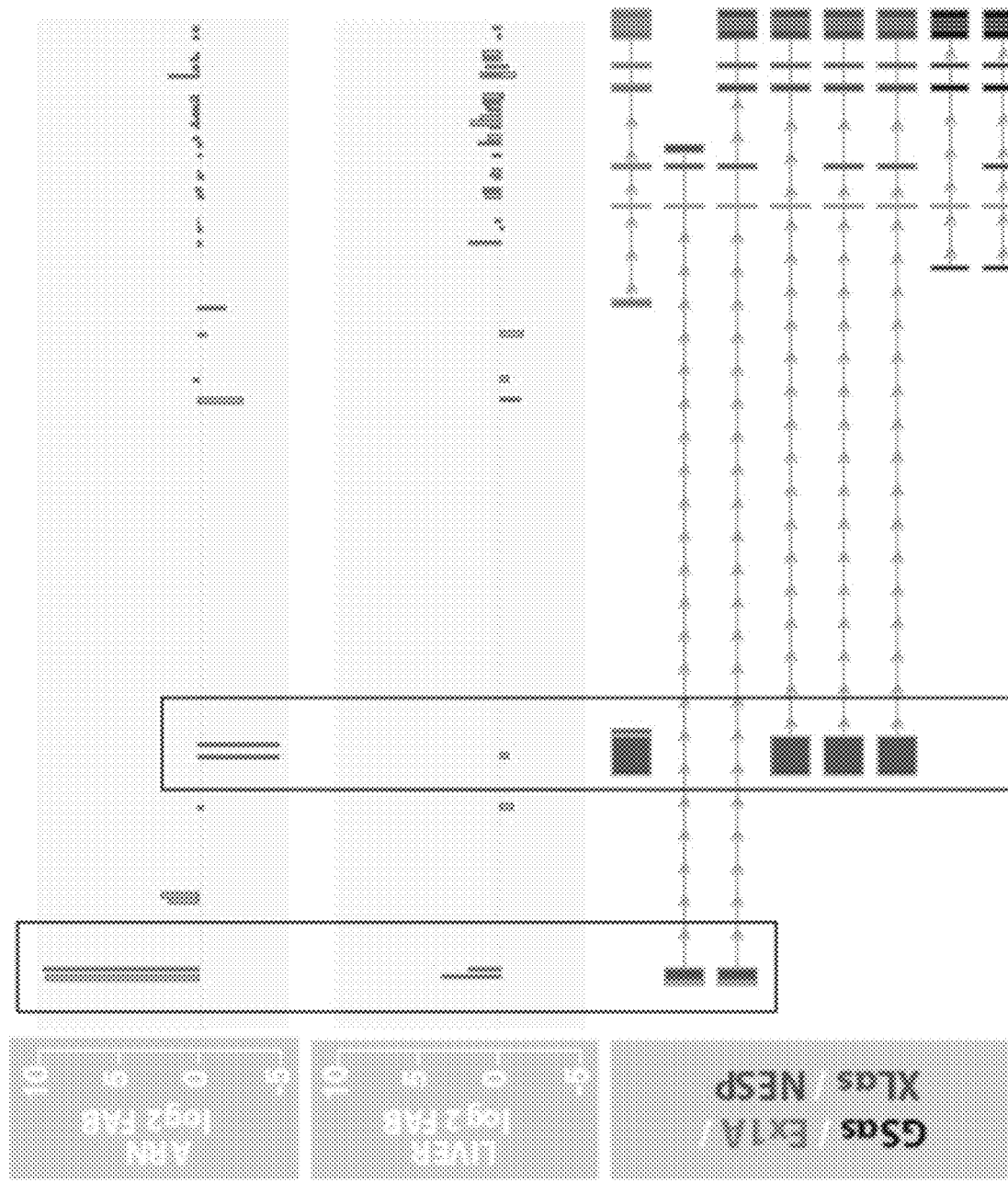

FIG. 12D is a plot of the log 2 FAB at the level of individual SNPs which identified distinct transcripts from the maternal and paternal alleles. A maternal bias was detected for the NESP transcript (red) in the ARN and liver, and the four XLas transcripts (dark blue) were associated with a paternal bias in the ARN (and DRN, not shown). Imprinting effects were not detected for the short GSαs (black) and Ex1A (sky blue) transcripts in any tissue.

Figure 13A:
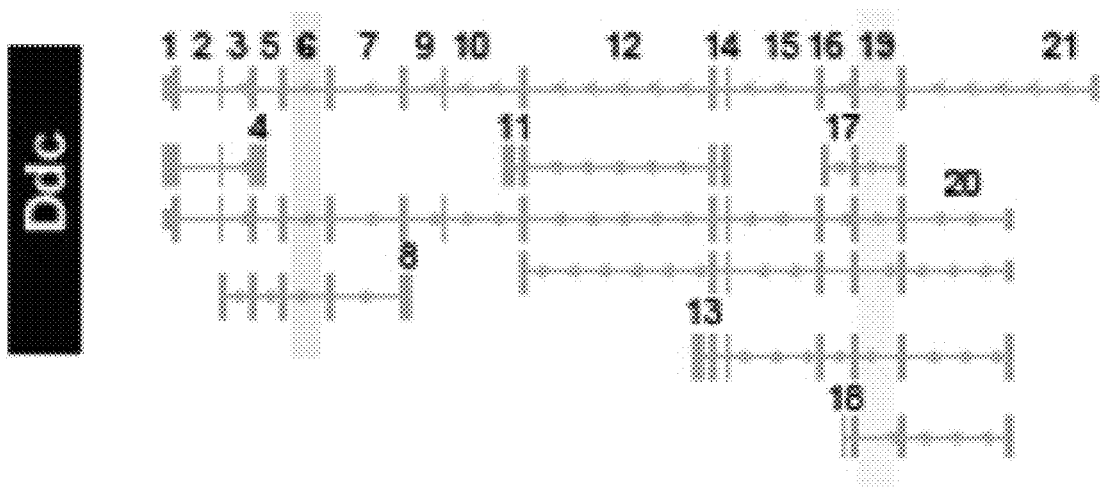

FIG. 13A is a gene model for Ddc isoforms. Introns are numbered based on a flattened gene model that includes all isoforms.

Figure 13B:
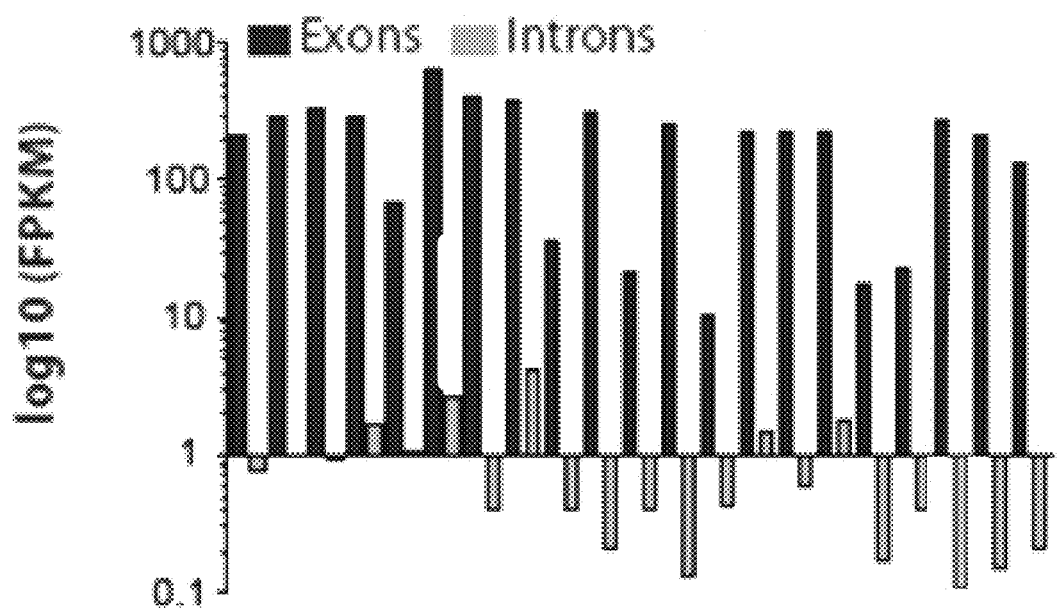

FIG. 13B is a bar graph showing the expression level of Ddc exons and introns in the DRN as determined by RNASeq in B6 mice. Introns that were retained exhibited relatively high expression, while introns that were rapidly processed exhibited low expression in the poly(A) captured mRNA.

Figure 13C:
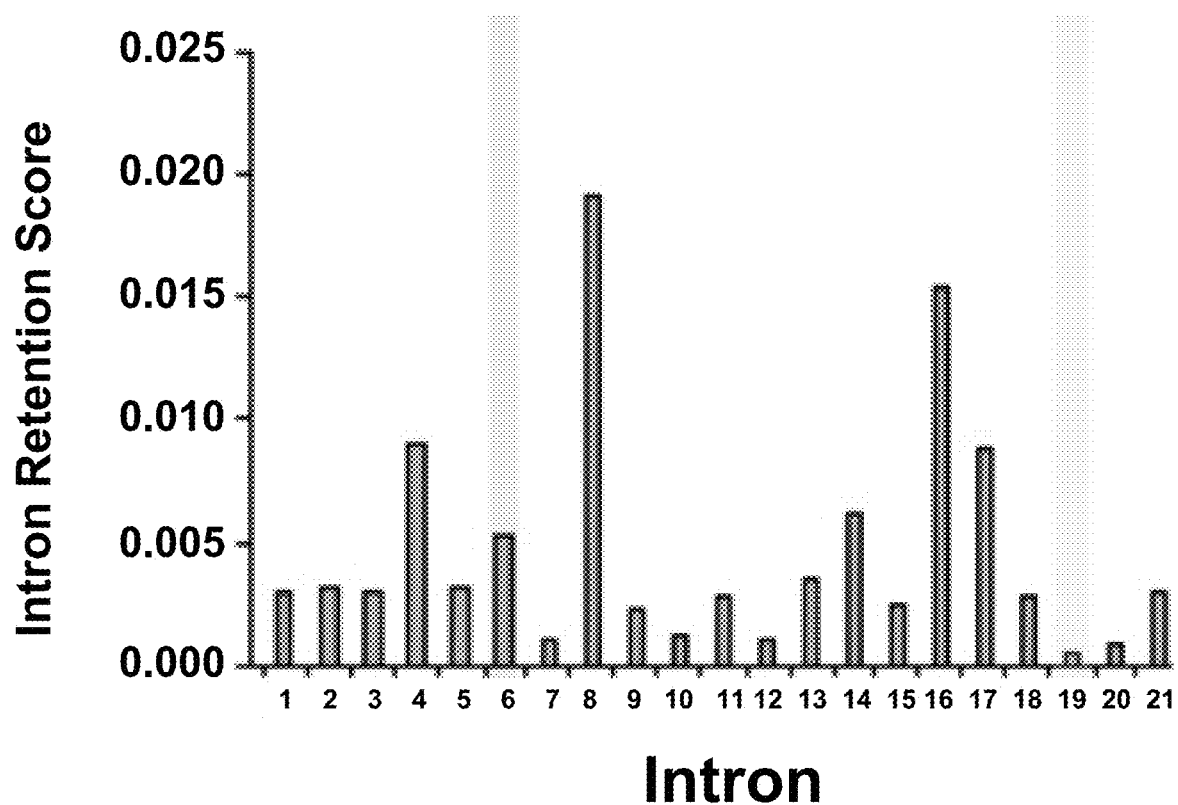

FIG. 13C is a bar graph showing that the intron retention score for each intron was based on the ratio of intron expression level to the mean expression level of the flanking exons. This approach clearly distinguished Ddc introns with high and low retention, including introns 6 and 19, respectively.

Figure 13D:
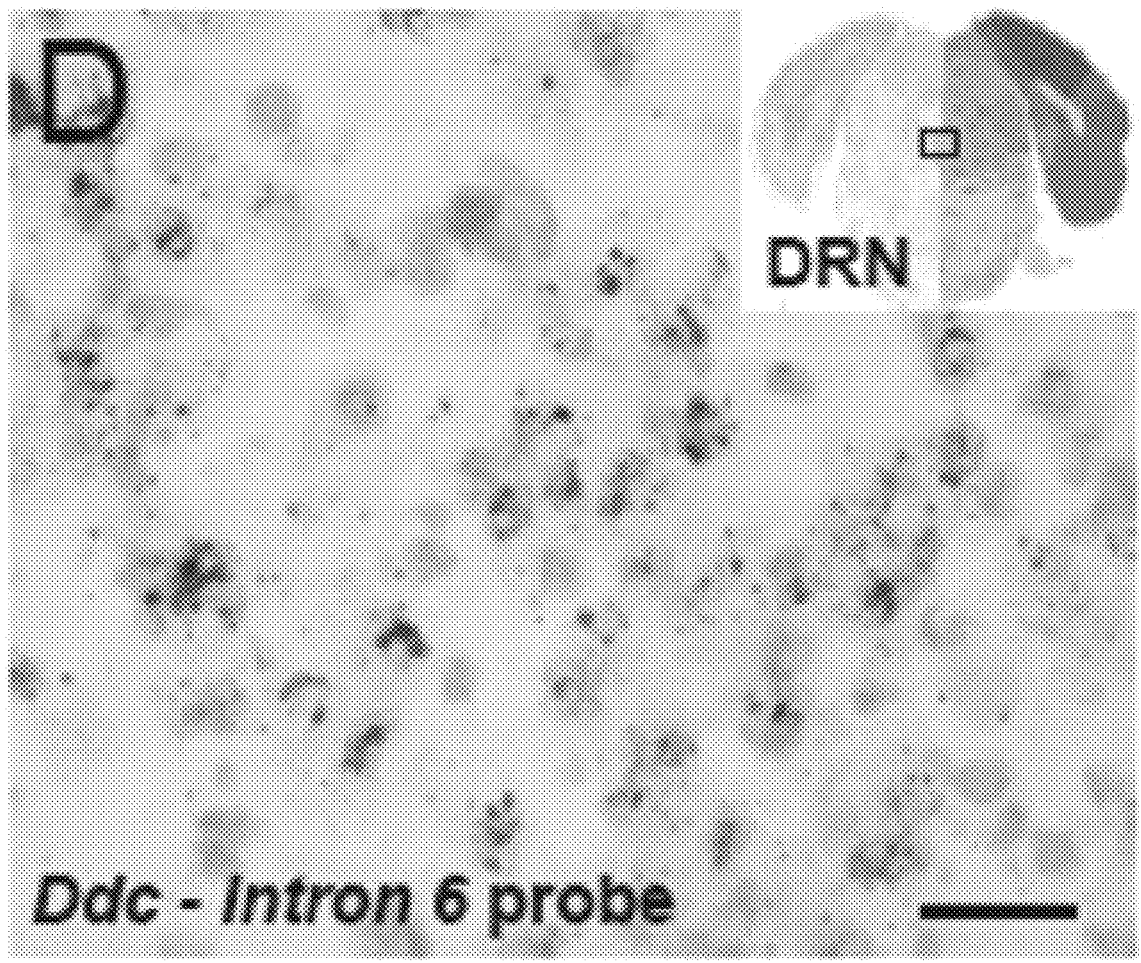
Figure 13E:
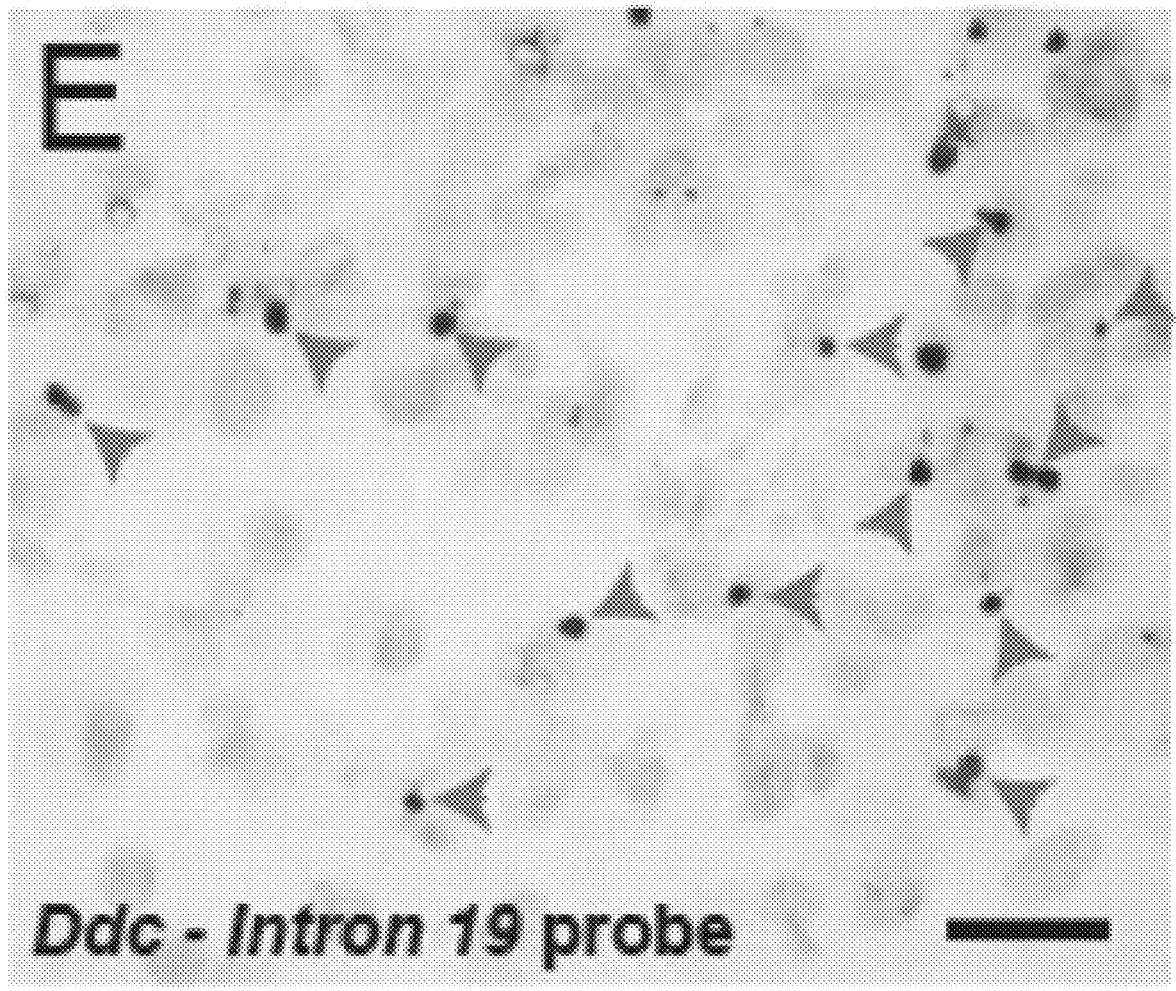

FIG. 13D and FIG. 13E are images showing in situ staining in the DRN for RNAscope probes targeting the retained Ddc intron 6 (D) and the rapidly processed intron 19 (E). The images demonstrated that probes targeting retained introns have a speckled staining pattern and revealed that RNA molecules that retained the intron are distributed throughout the nucleus (D). In contrast, probes targeting rapidly processed introns clearly revealed the focal site(s) of transcription in the nucleus, due to the fact that the RNA containing the rapidly processed intron is located at the site of transcription (E). Both biallelic (orange arrows) and monoallelic (green arrows) cells were clearly visible in the DRN for Ddc.

Figure 13F:
Figure 13G:
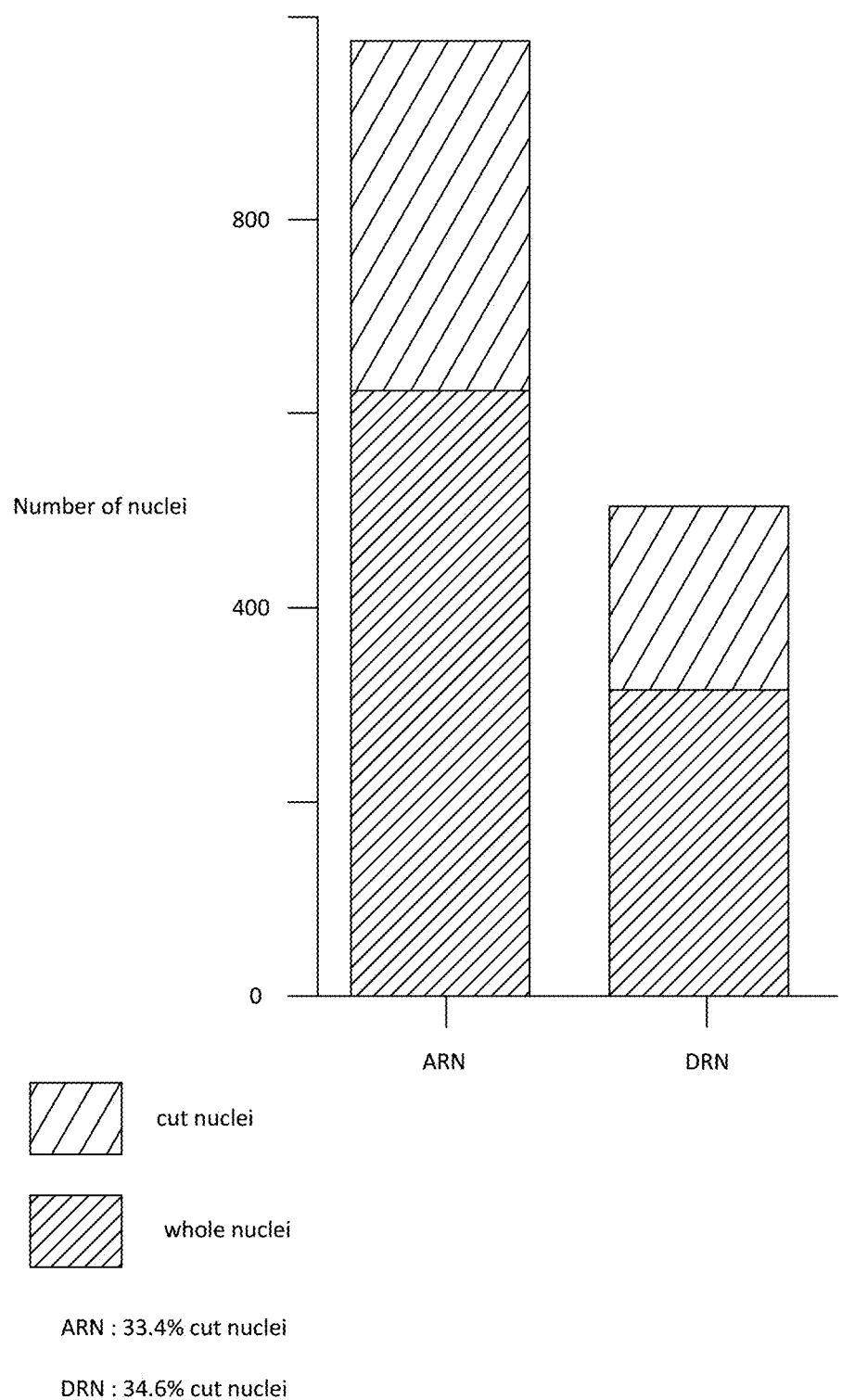

FIG. 13F and FIG. 13G are an image and a bar graph showing an xz cross-section and the quantification of the number of partial nuclei of the ARN and DRN determined from confocal z-stacks of DAPI stained nuclei in the cross-section. Examples of partial (yellow arrows) and whole (pink arrows) nuclei from confocal Z-stack images are shown.

Figure 13H:
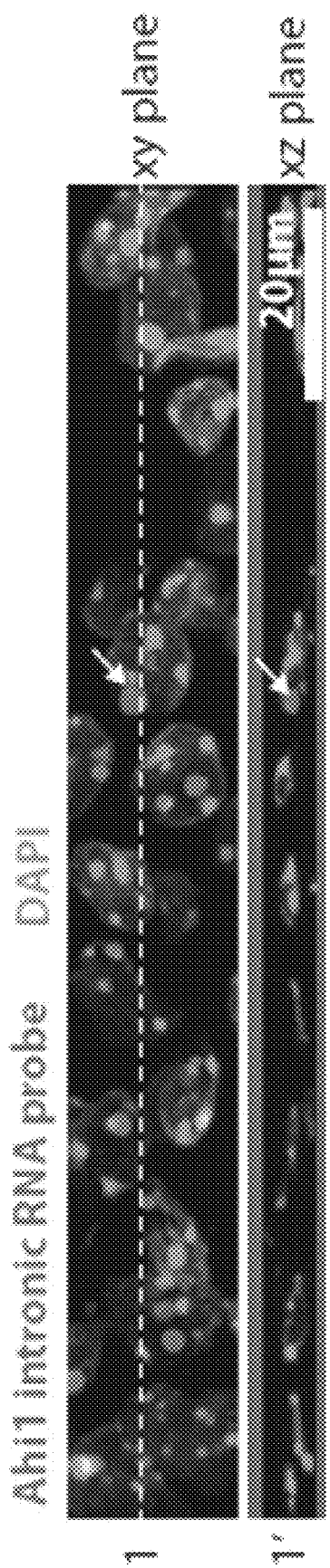
Figure 13I:
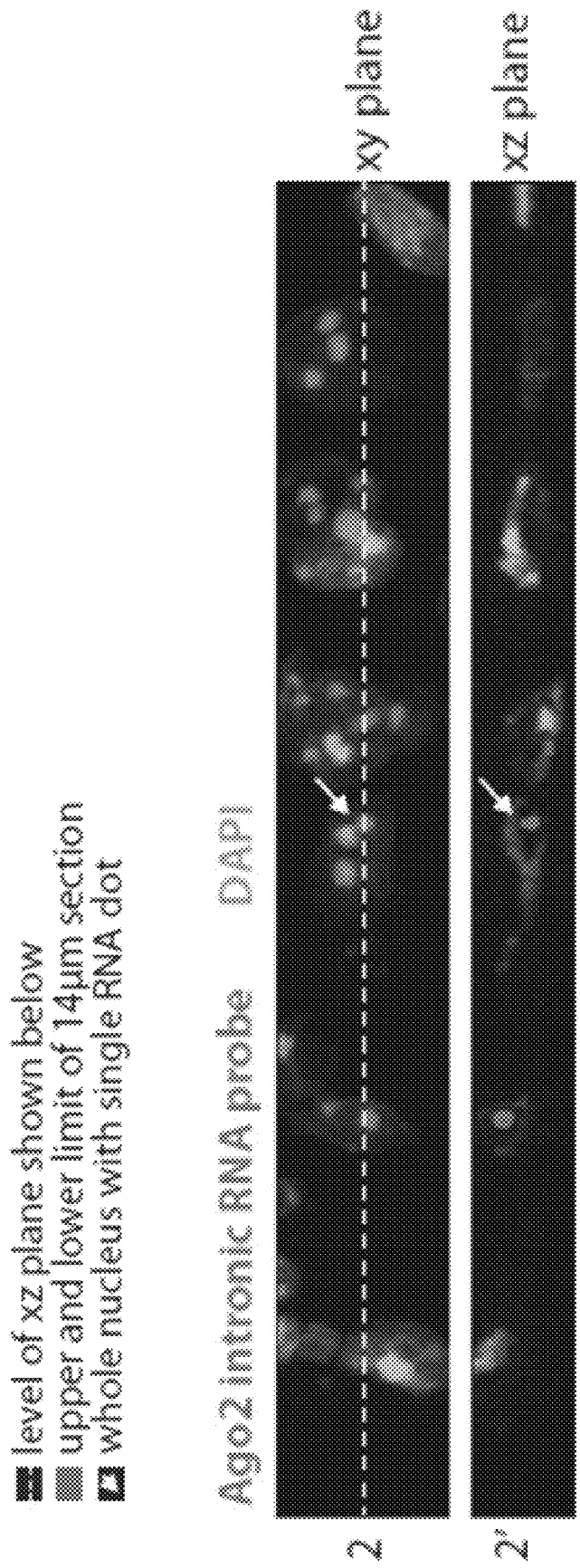

FIG. 13H and FIG. 13I are images showing fluorescent in situ hybridization which detected the nascent RNA for the noncanonical imprinted genes Ahi1 (H) and Ago2 (I). Confocal images revealed subpopulations of biallelic (two transcriptional foci) and monoallelic (one transcriptional site) cells for each gene. Examples of whole nuclei exhibiting monoallelic expression are indicated by the white arrow in the xy and xz planes. These results indicated that monoallelic subpopulations exist and are not due to sectioning artifacts.

Figures 14A, 14B:
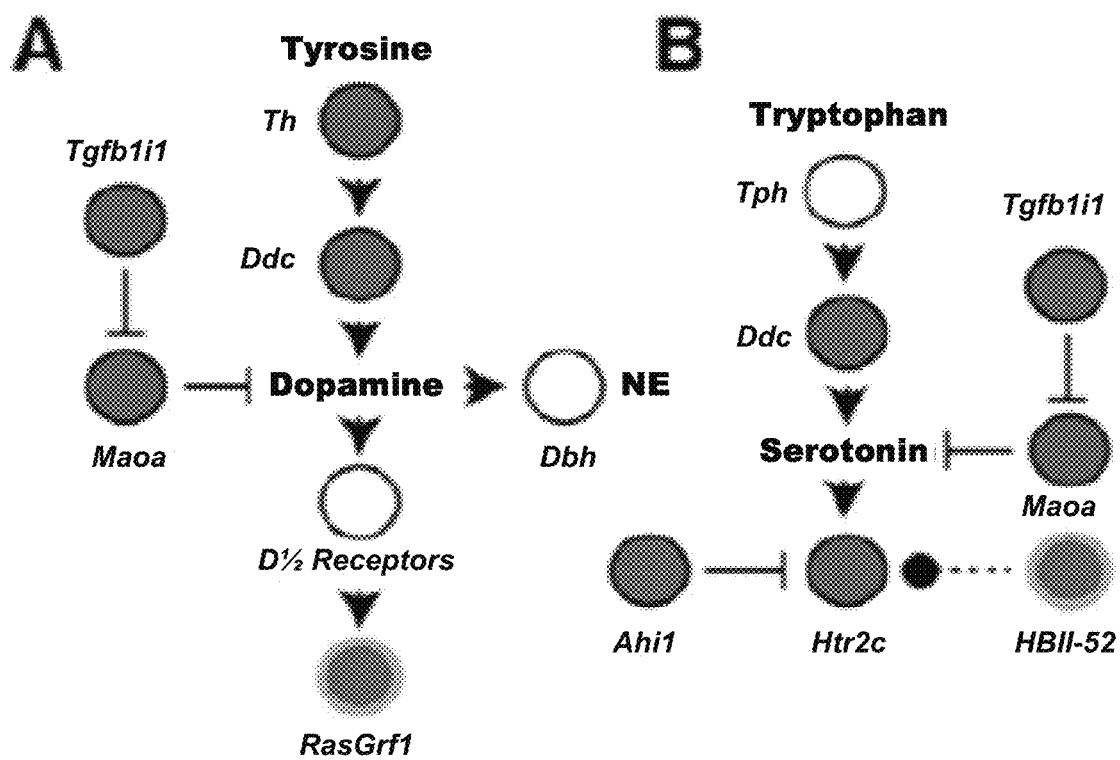

FIG. 14A and FIG. 14B are a summary of canonical (yellow border) and noncanonical (black border) MEGs (red) and PEGs (blue) in the catecholamine (A) and serotonin (B) pathways. X-linked MEGs are indicated in pink.

Figure 14C:
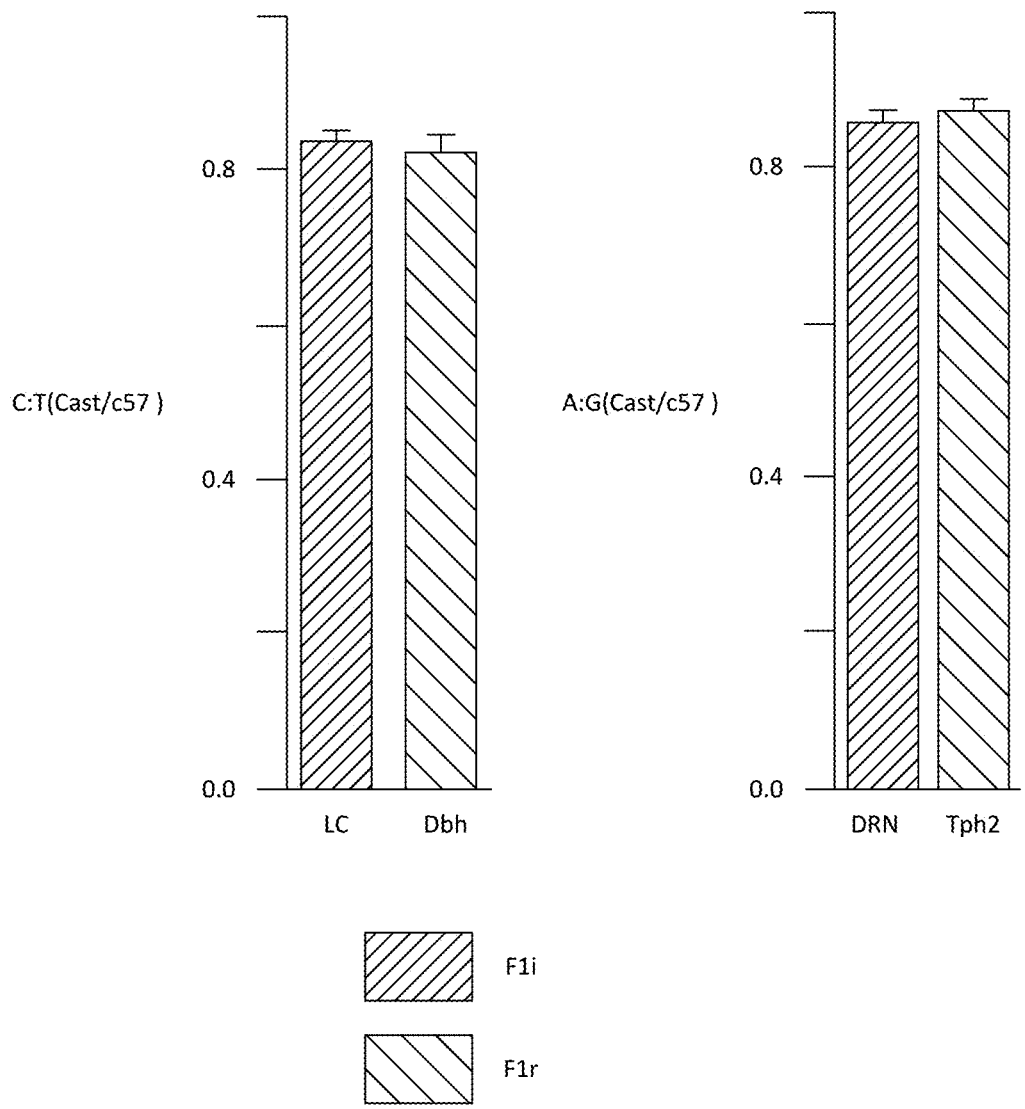

FIG. 14C is a bar graph showing that pyrosequencing revealed that Dbh and Tph2 are not imprinted in the LC and DRN, respectively.

FIG. 14D to FIG. 14G are bar graphs showing pyrosequencing results for Th, Ddc, Tgfbli1, and Ahi1 in the ARN, DRN, VTA, and LC. All genes cross revealed a noncanonical imprinting effect. Only Ddc exhibited a significant interaction between cross and brain region (BR), which revealed brain region differences in the imprinting effect. A Tukey HSD post-test determined that Ddc exhibited a significant maternal bias in the ARN, DRN, and LC, but not the VTA.

Figure 14D:
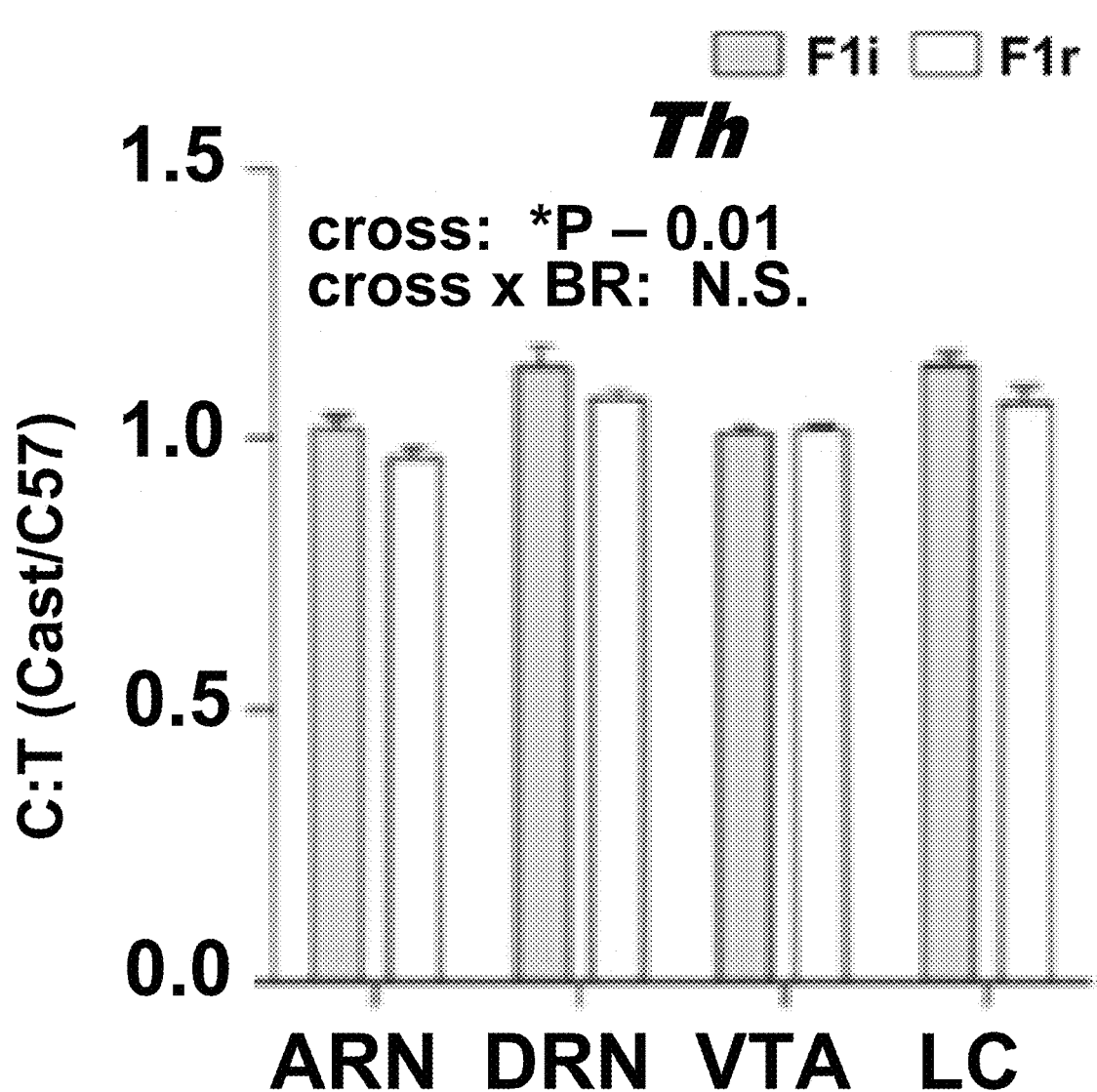
Figure 14E:
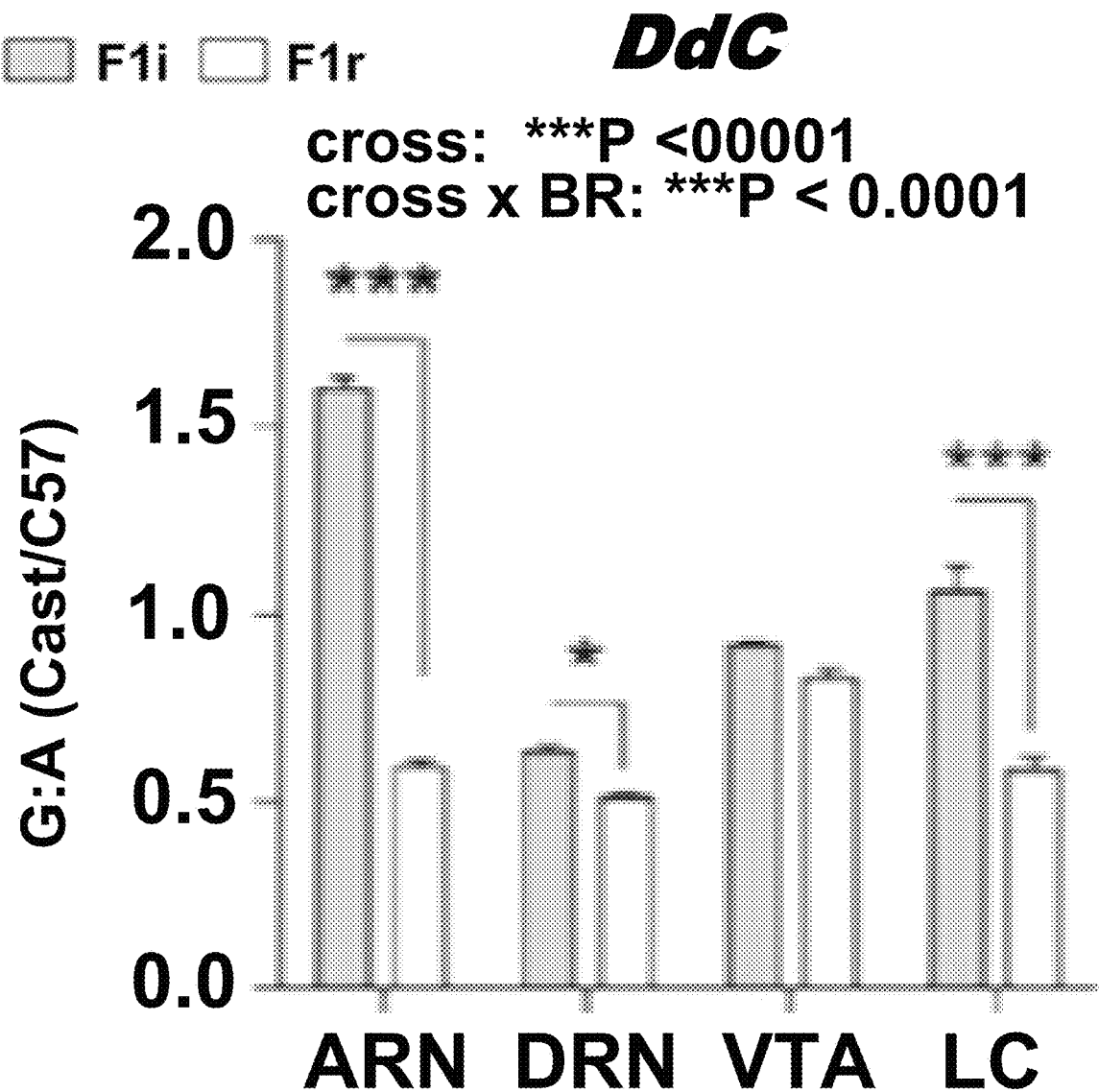
Figure 14F:
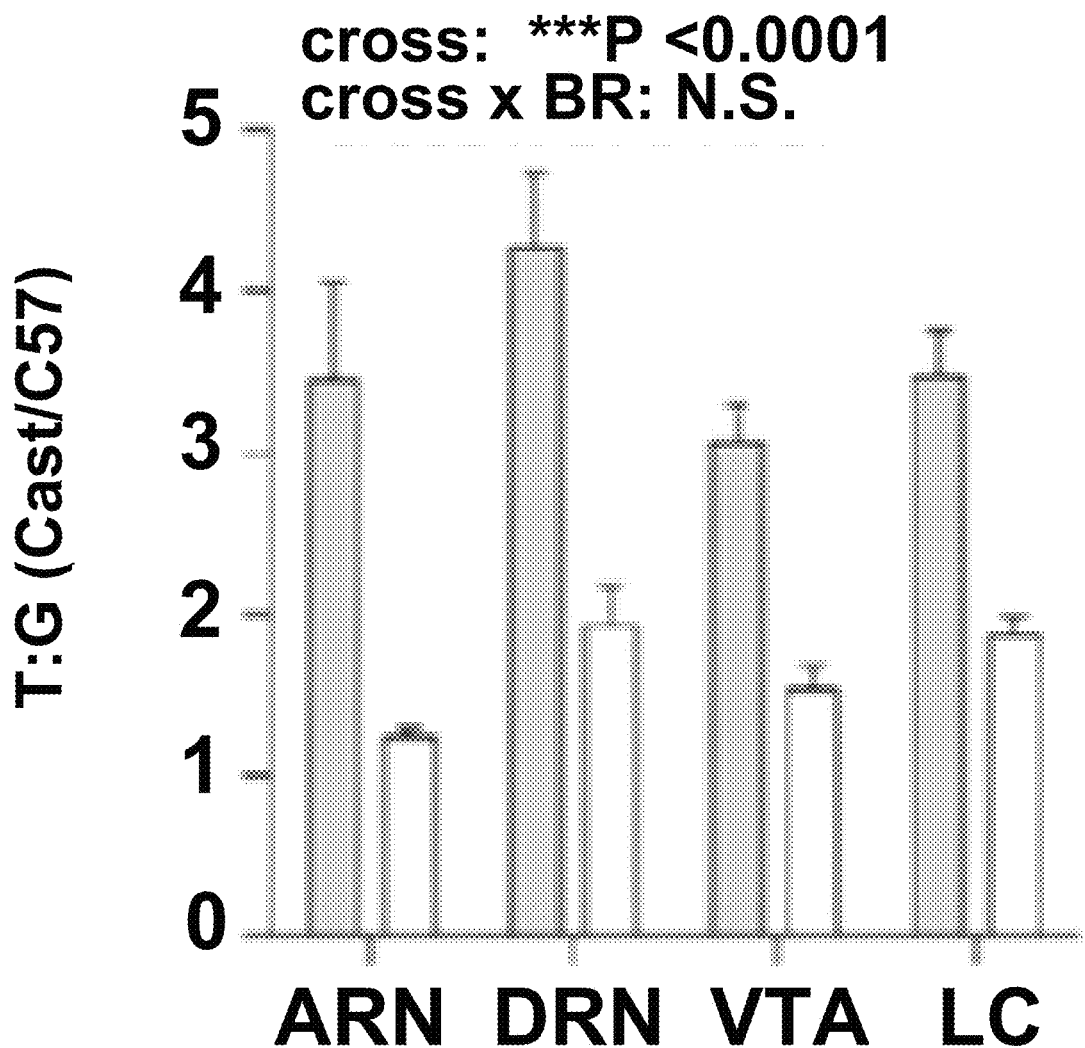
Figure 14G:
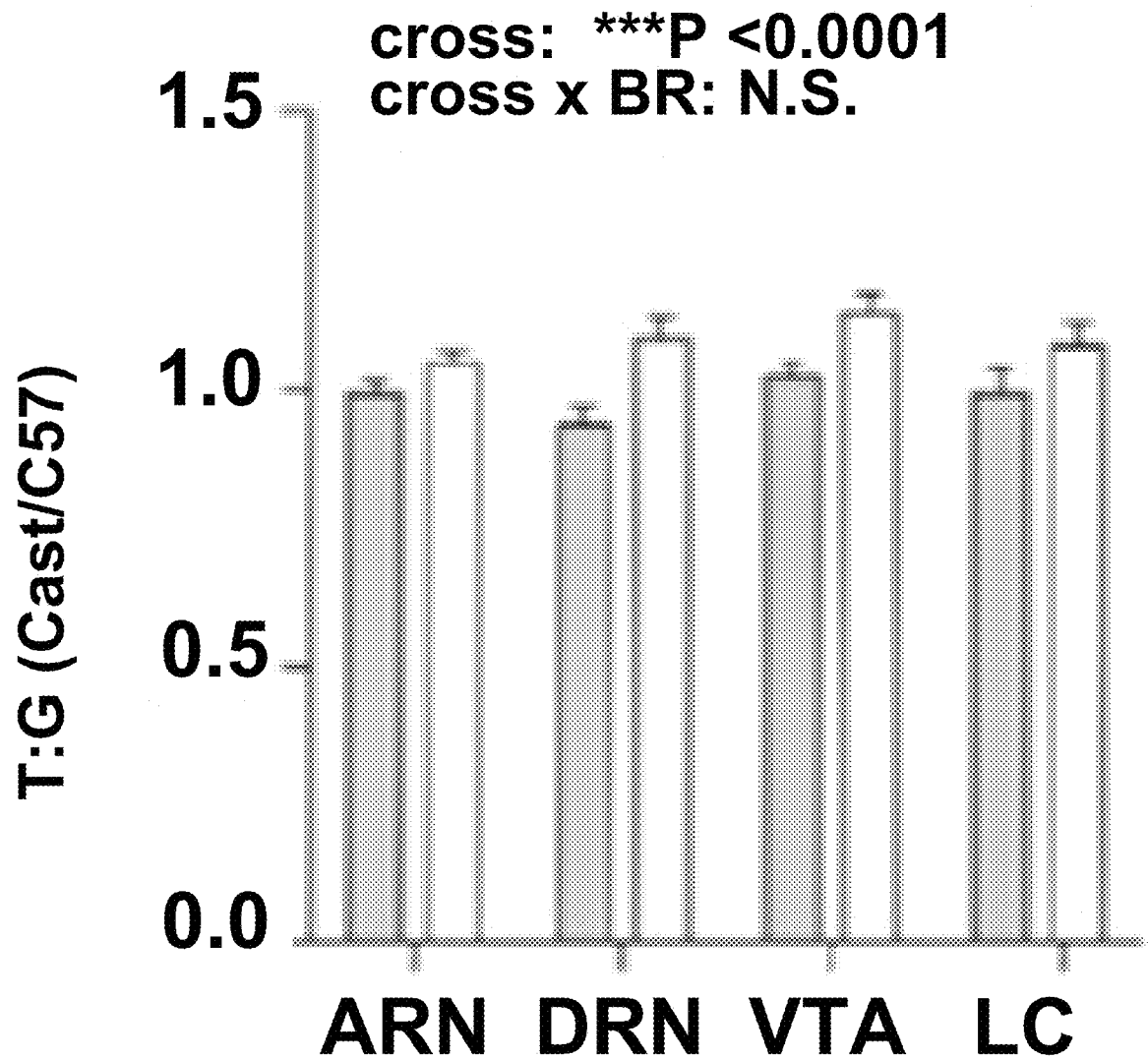
Figure 14H:
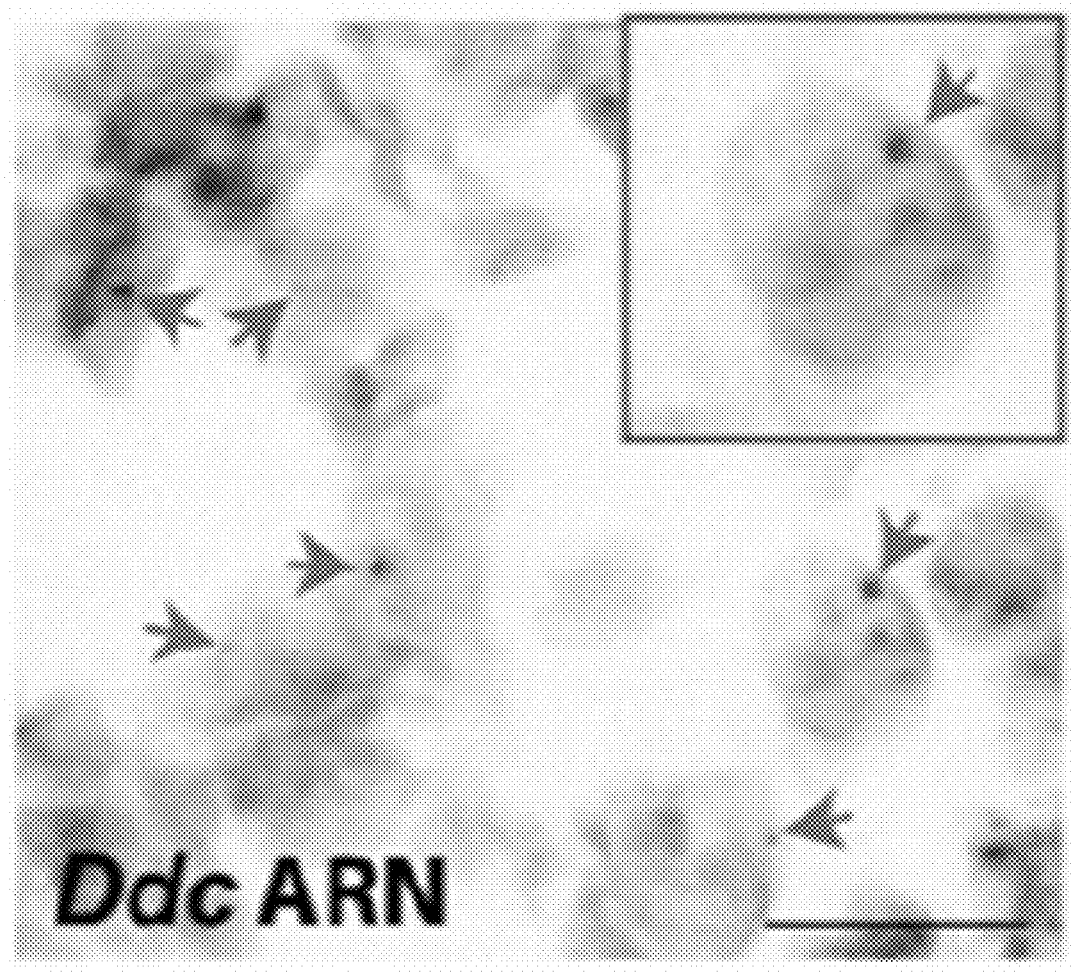
Figure 14I:
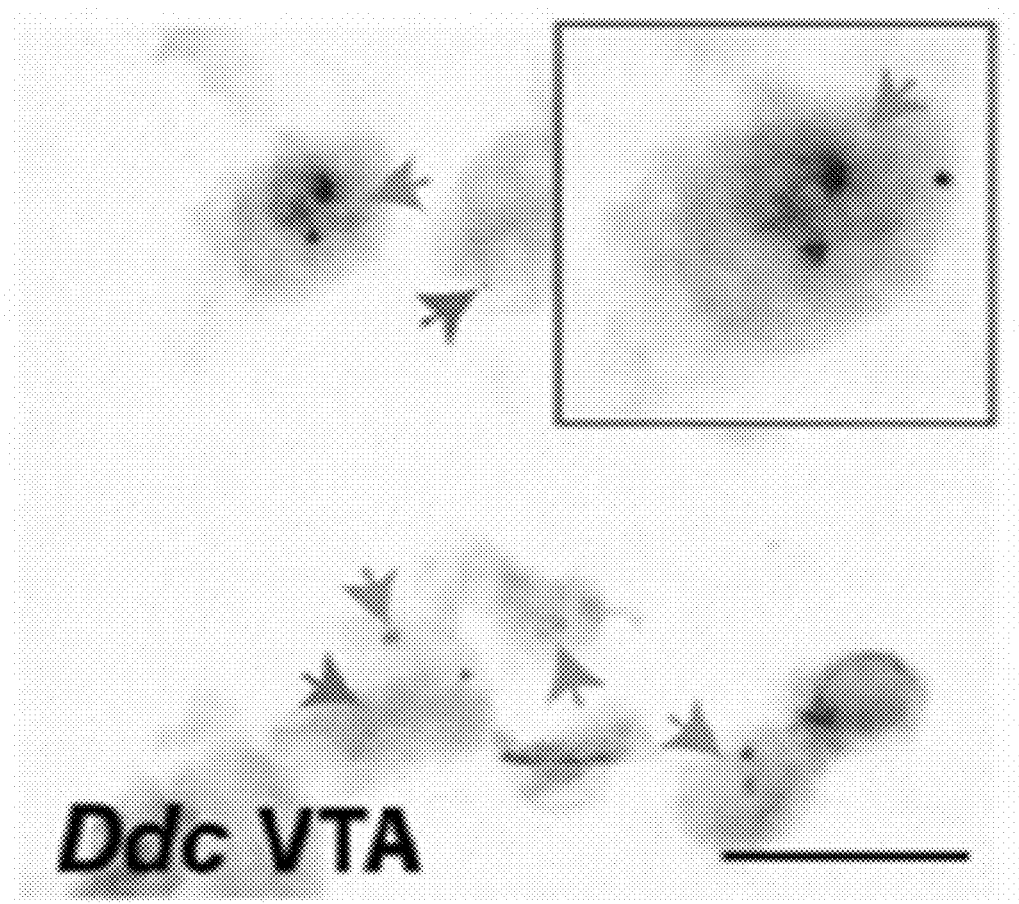

FIG. 14H and FIG. 14I are images showing that Ddc nascent RNA in situ reveals monoallelic and biallelic subpopulations of neurons in the ARN (H) and VTA (I).

Figure 14J:
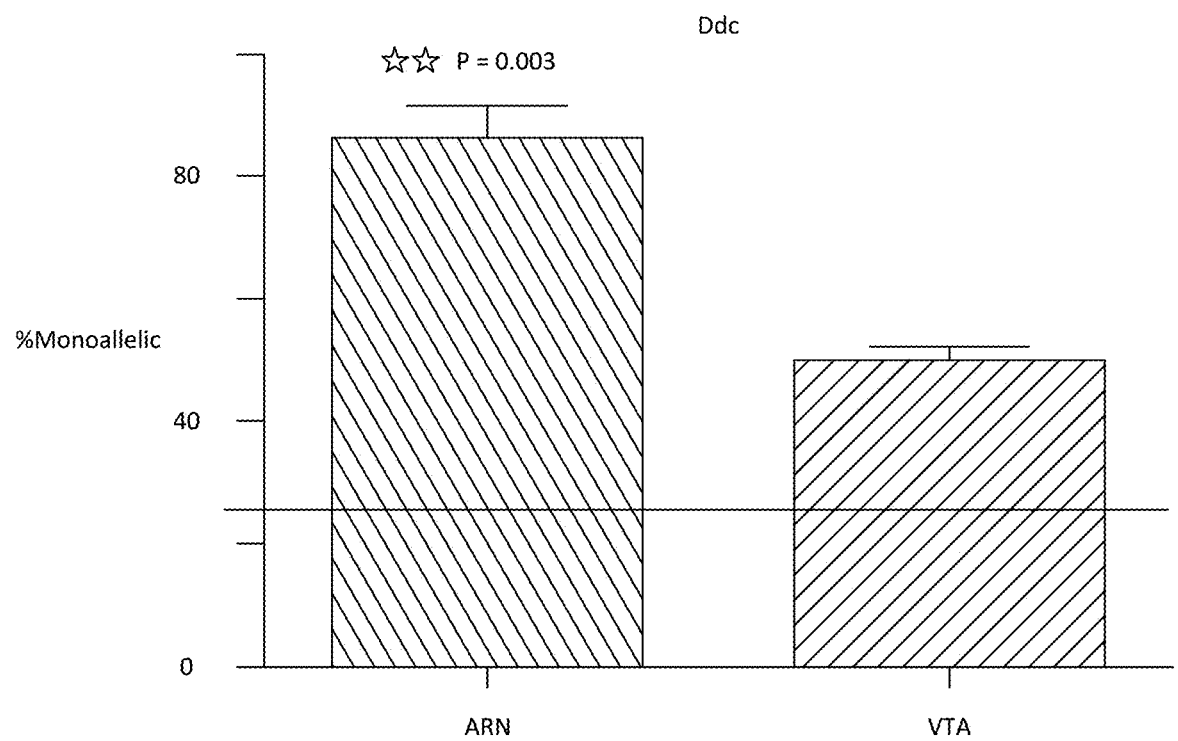

FIG. 14J is a bar graph showing that a significantly larger proportion of Ddc+ cells exhibited monoallelic expression in the ARN compared to the VTA (line indicates Syn2 estimated false monoallelic background).

Figure 14K:
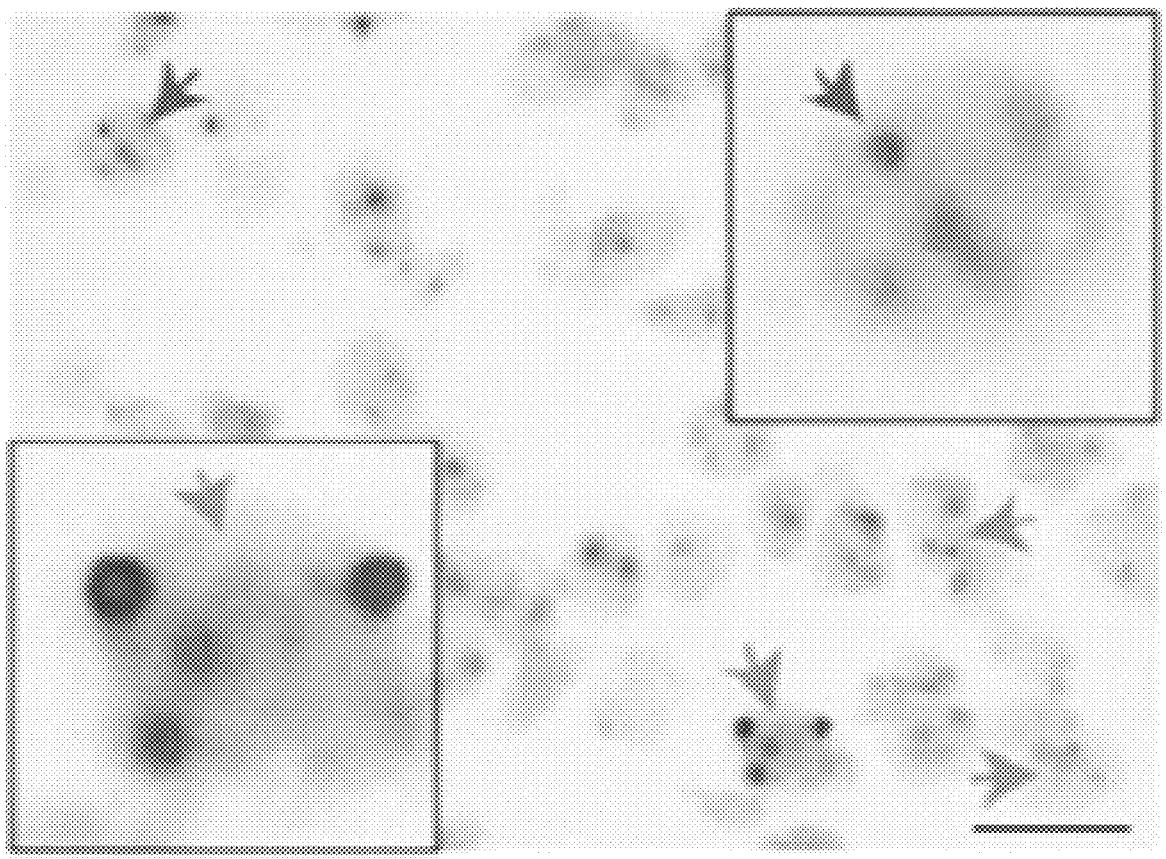

FIG. 14K is an image showing Th nascent RNA in situ (blue) revealed monoallelic and biallelic cells in the brain (ARN shown). Biallelic Syn2 control is shown in dark red.

Figure 14L:
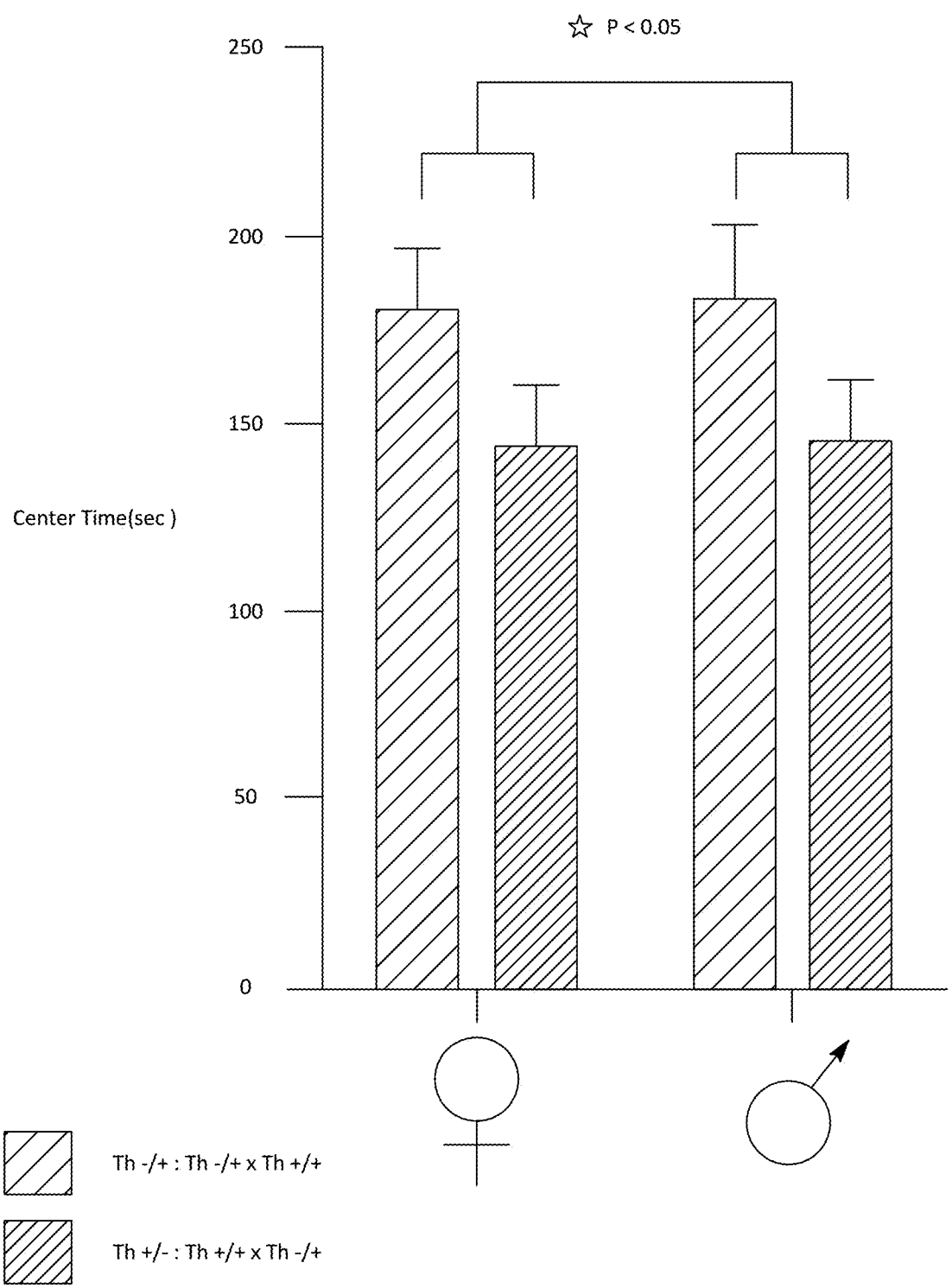
Figure 14M:
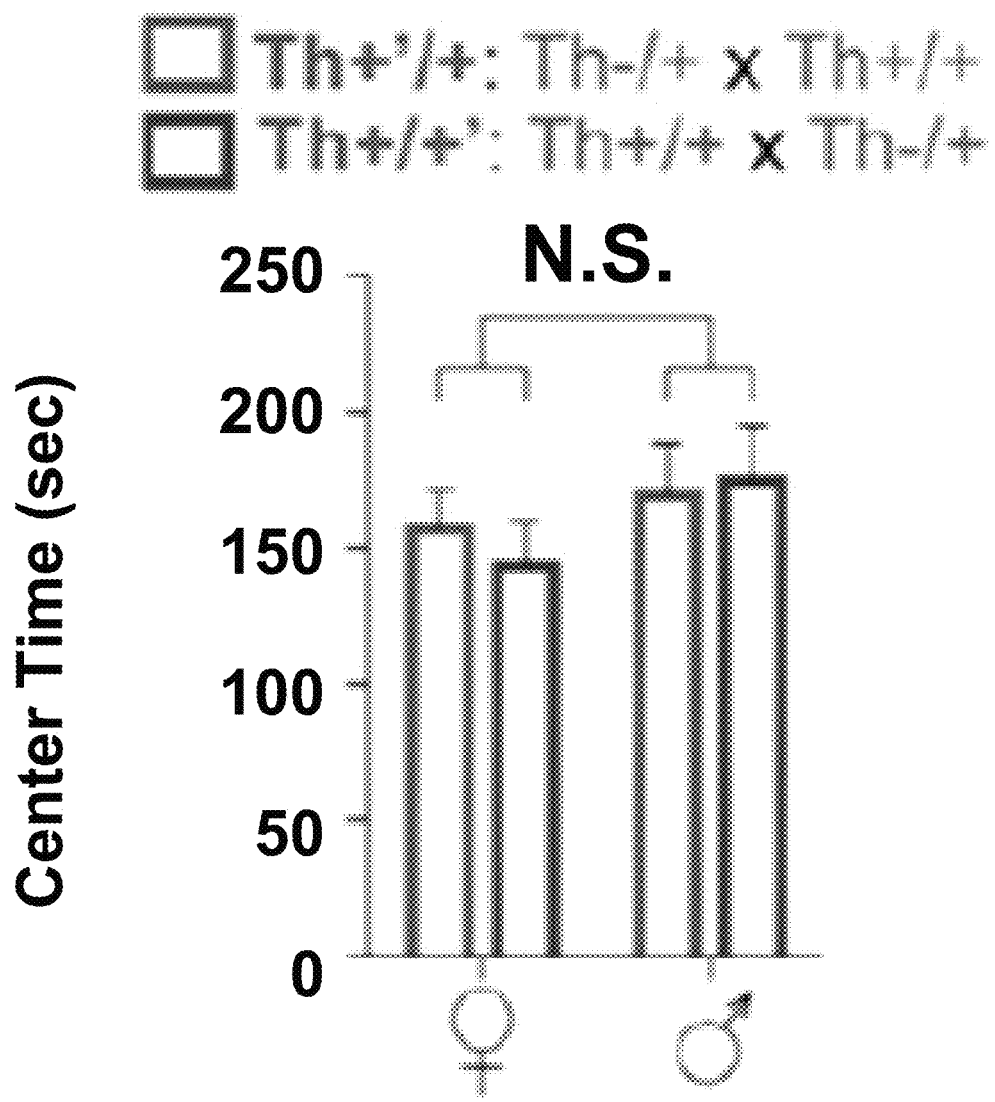

FIG. 14L and FIG. 14M are bar graphs showing the total time in the center region for $Th^{+/-}$ and $Th^{-/+}$ females and males in the open-field task revealed a main effect of the parental origin of the mutant allele.

Figure 14N:
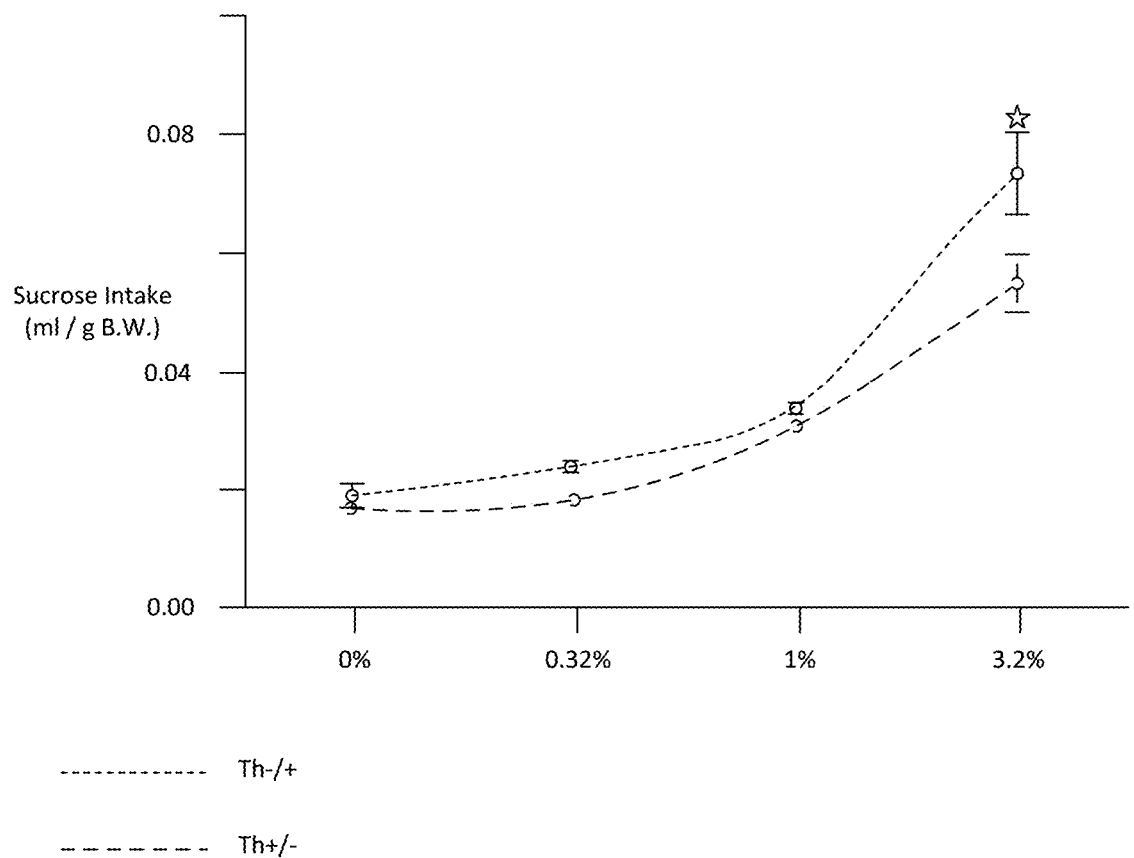

FIG. 14N is a line graph showing that the sucrose solution intake per gram of body weight (BW) at increasing sucrose concentrations revealed a significant increase in sucrose consumption for $Th^{-/+}$ compared to $Th^{+/-}$ offspring for the 3.2% sucrose solution (data for males and females are pooled since no significant sex difference was detected).

Figure 14O:
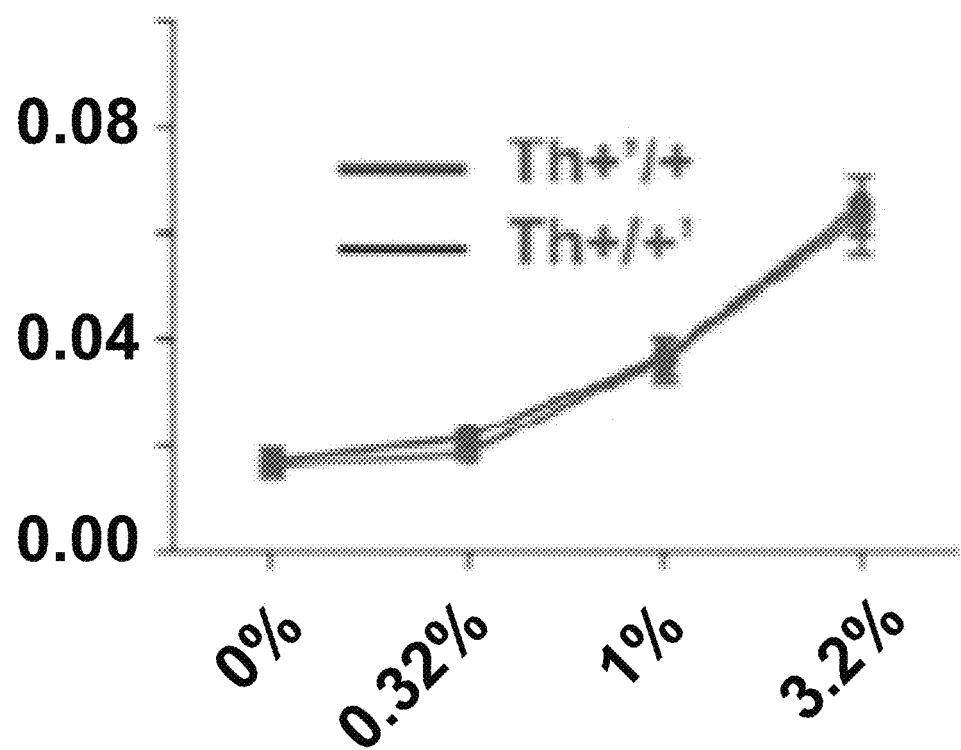

FIG. 14O is a line graph showing that no difference was detected between the wild-type littermates.

Figure 15A:
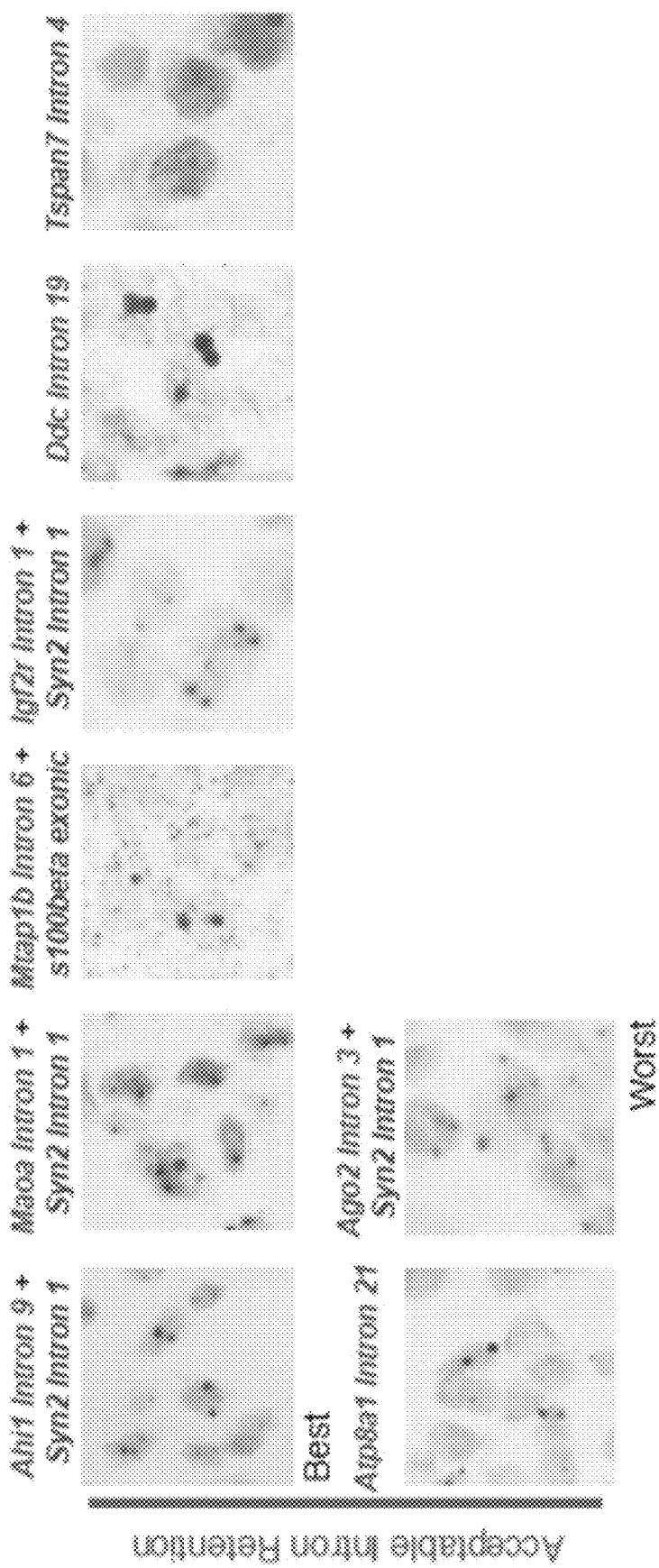

FIG. 15A are images of single and double in situ hybridization labeling in the adult female mouse dorsal raphe for 16 intronic probes and 2 exonic probes (s100beta and Mopb).

Figure 15B:
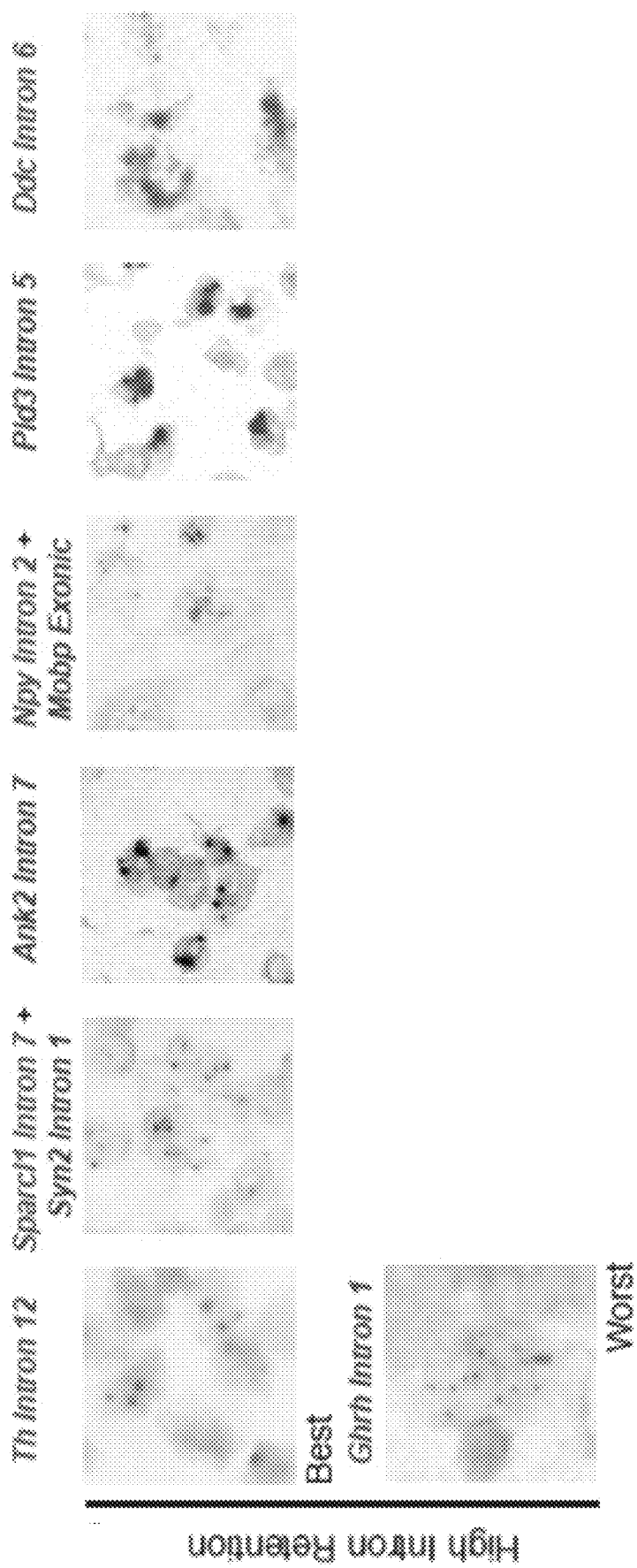

FIG. 15B are images of single and double in situ hybridization labeling in the adult female mouse dorsal raphe for 7 probes that have high levels of intron retention which obscured allelic expression, ordered from best (partial background) to worst (completely obscured).

Figure 15C:
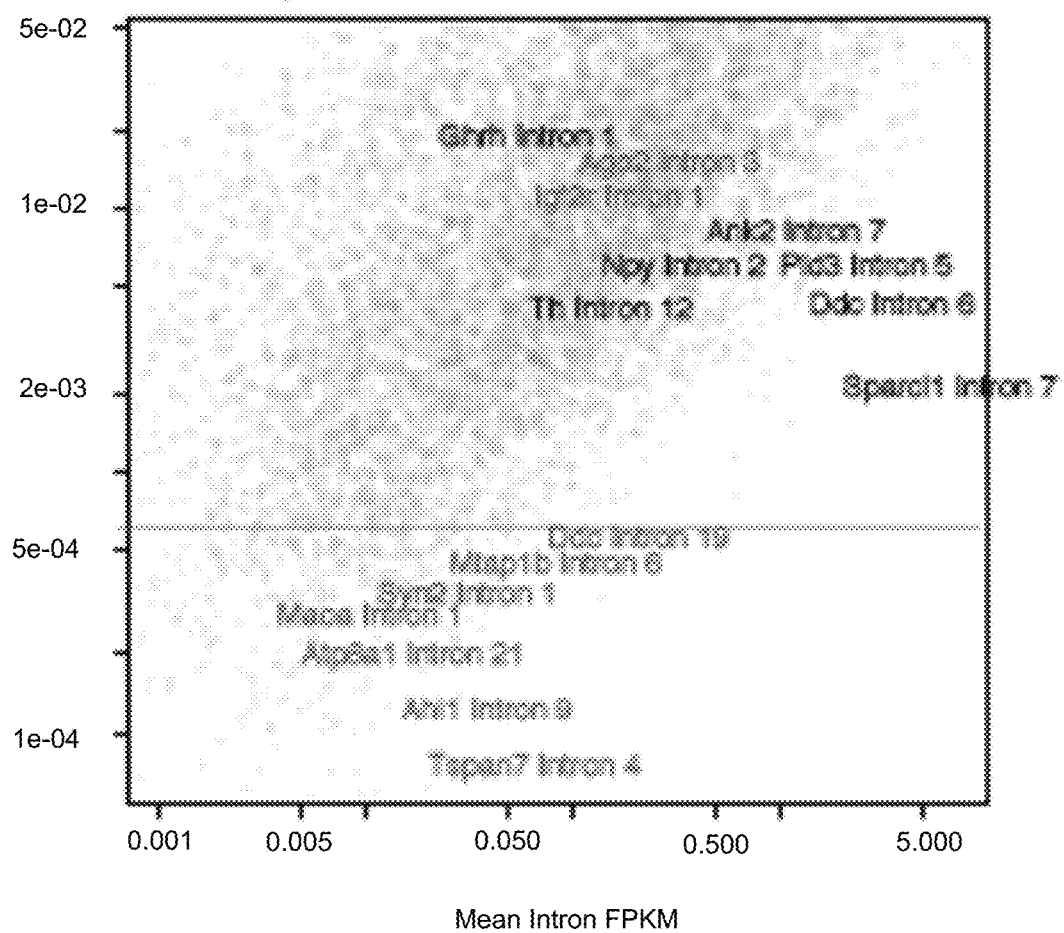

FIG. 15C is a plot of intron retention score versus expression level (FPKM) for polyA purified RNASeq, which revealed that low intron retention scores enriched for probes with improved signal and low background, while genes with high intron retention background labeling showed a high intron retention score by RNASeq.

Figure 15D:
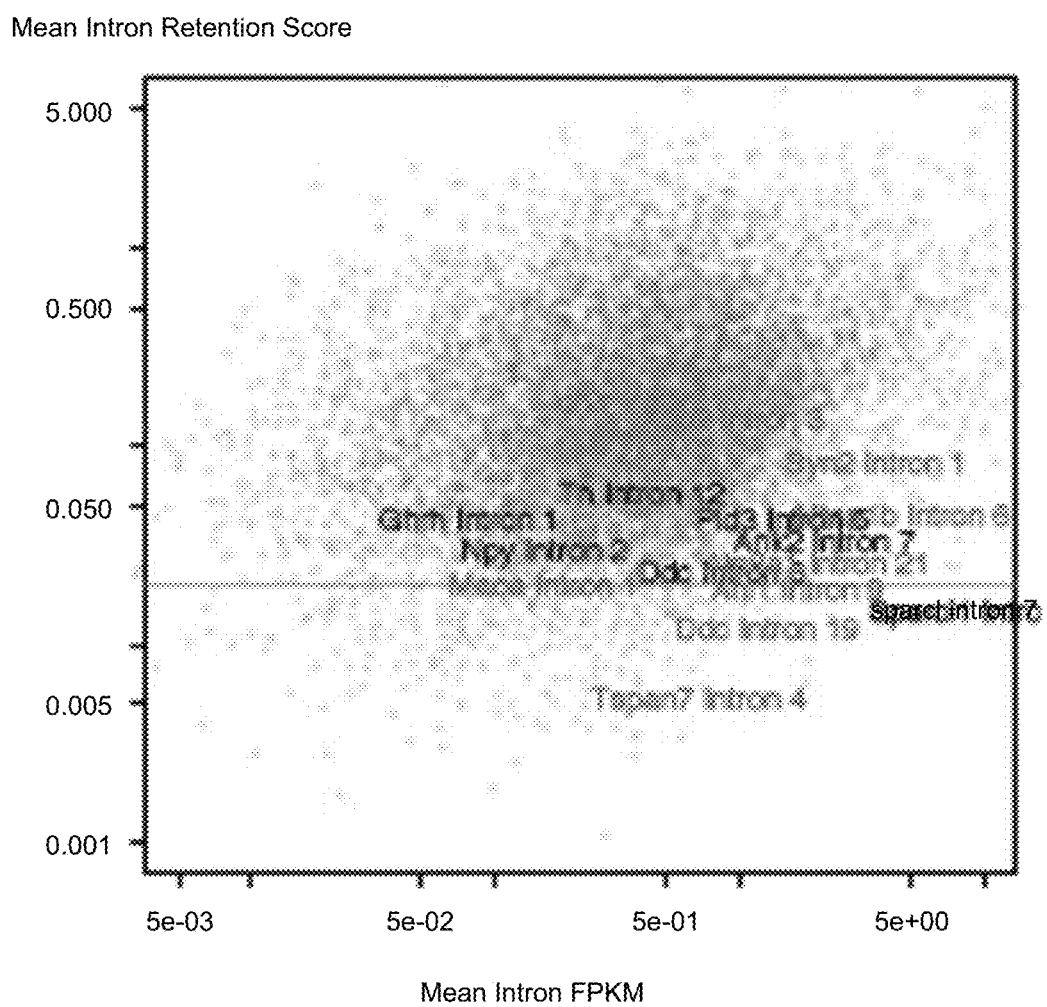

FIG. 15D is a plot of intron retention score versus expression level (FPKM) for whole nuclear transcriptome RNASeq, which revealed relatively poor classification of introns for probes with low versus high background staining.

DETAILED DESCRIPTION OF THE INVENTION

This disclosure provides methods for identifying one or more introns of a gene that are rapidly processed from a nascent RNA molecule transcribed from the gene, which allow for the detection of allele-specific expression of a gene in a single cell.

The terms "gene" or "gene sequence," as used herein, refer to a distinct nucleic acid sequence (DNA or RNA) that directly encodes an RNA molecule or polypeptide. By "nucleic acid sequence" is meant a polymer of DNA or RNA, i.e., a polynucleotide, which can be single-stranded or double-stranded and which can contain non-natural or altered nucleotides. Nucleic acids are typically linked via phosphate bonds to form nucleic acids or polynucleotides, though many other linkages are known in the art (e.g., phosphorothioates, boranophosphates, and the like). The term "allele," as used herein, refers to one of a number (typically two) of alternative forms of the same gene or genetic locus (Feero et al., *N. Engl. J. Med.*, 362 (21): 2001-2011 (2010)).

The term "transcription," as used herein, is the process of creating an equivalent RNA copy of a sequence of DNA, and involves the steps of initiation, elongation, termination, and RNA processing (which includes splicing) (see, e.g., Griffiths et al., eds., *Modern Genetic Analysis: Integrating Genes and Genomes*, 2nd ed., W. H. Freeman and Co., New York (2002)). The term "nascent RNA molecule" refers to an RNA molecule that is in the process of being synthesized or a complete newly synthesized RNA molecule that has not yet undergone posttranscriptional processing. Nascent RNA also is referred to in the art as pre-messenger RNA ("pre-mRNA") or a primary transcript. The term "posttranscriptional processing," as used herein, refers to the modifications made to nascent RNA molecules (or pre-mRNAs) before the nascent RNA molecules exit the nucleus of a cell. Such modifications include, for example, capping of the 5' end of the nascent RNA (typically with a 7-methylguanosine linked to the first nucleotide via a 5'-5' triphosphate bridge), polyadenylation of the 3' end of the nascent RNA, and removal of introns via splicing. In some embodiments, a nascent RNA molecule also can be in the process of posttranscriptional processing, in which case the nascent RNA can be considered a "messenger RNA" (mRNA) that may or may not be polyadenylated.

During transcription of eukaryotic genes, introns are removed from precursor messenger RNA (pre-mRNA), and exons are joined via RNA splicing. Thus, in some embodiments, the one or more nascent RNA molecules comprise one or more exons and introns. The term "exon," as used herein, refers to a nucleic acid sequence present in a gene which is represented in the mature form of an RNA molecule after excision of introns during transcription. Exons are translated into protein(s). The term "intron," as used herein, refers to a nucleic acid sequence present in a given gene which is not translated into protein and is generally found between exons. RNA splicing is catalyzed by a large RNA-protein complex called the spliceosome, which is comprised of five small nuclear ribonucleoproteins (snRNPs) (see, e.g., Watson et al. (eds.), *Molecular Biology of the Gene, 6th Edition*, Cold Spring Harbor Laboratory Press, Cold Spring Harbor, N.Y. (2008)). The borders between introns and exons are marked by specific nucleotide sequences within a pre-mRNA, which delineate where splicing will occur.

The methods disclosed herein comprise providing a cell comprising a gene of interest, and expressing the gene of interest in the cell. Preferred host cells are those that can be easily and reliably grown, have reasonably fast growth rates, have well characterized expression systems, and can be transformed or transfected easily and efficiently. In some embodiments, the cell is a eukaryotic cell. Suitable eukaryotic cells are known in the art and include, for example, yeast cells, insect cells, and mammalian cells. Examples of suitable yeast cells include those from the genera *Hansenula, Kluyveromyces, Pichia, Rhino-sporidium, Saccharomyces,* and *Schizosaccharomyces*. Preferred yeast cells may include, for example, *Saccharomyces cerivisae* and *Pichia pastoris*. Suitable insect cells may include, for example, Sf-9 and HIS cells (Invitrogen, Carlsbad, Calif.), and are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993).

In some embodiments, the cell may be a mammalian cell. A number of suitable mammalian host cells are known in the art, some of which are available from the American Type Culture Collection (ATCC, Manassas, Va.). Examples of suitable mammalian cells may include, but are not limited to, Chinese hamster ovary cells (CHO) (ATCC No. CCL61), CHO DHFR-cells (Urlaub et al., Proc. Natl. Acad. Sci. USA, 97: 4216-4220 (1980)), and 3T3 cells (ATCC No. CCL92). Other suitable mammalian cell lines may include the monkey COS-1 (ATCC No. CRL1650) and COS-7 cell lines (ATCC No. CRL1651), as well as the CV-1 cell line (ATCC No. CCL70). Further exemplary mammalian host cells may include primate cell lines and rodent cell lines, including transformed cell lines. Normal diploid cells, cell strains derived from in vitro culture of primary tissue, as well as primary explants also are suitable. Other suitable mammalian cell lines may include, but are not limited to, mouse neuroblastoma N2A cells, mouse L-929 cells, and BHK or HaK hamster cell lines, all of which are available from the ATCC. Methods for selecting suitable mammalian host cells and methods for transformation, culture, amplification, screening, and purification of such cells are known in the art (see, e.g., Ausubel et al., eds., *Short Protocols in Molecular Biology, 5th ed.*, John Wiley & Sons, Inc., Hoboken, N.J. (2002)).

In some of the methods disclosed herein, a human cell may be used. A number of suitable human cells are known in the art and/or available from the ATCC, and may include, for example, human embryonic kidney (HEK) 293 or 293T cells (ATCC No. CRL1573), HeLa cells, A549 cells, MCF7 cells, HT29 cells, K562 cells, HUVEC cells, HCT 116 cells, Saos-2 cells, and RAMOS cells, among others. Human primary cells may also be used in the methods described herein.

The gene of interest may be endogenous (i.e., native) to a particular cell. For example, the gene of interest may be present in the chromosomal genome or mitochondrial DNA of a particular cell. In some embodiments, the gene of interest may be exogenous to a particular cell, and may be introduced into a cell by "transfection," "transformation," or "transduction." "Transfection," "transformation," or "transduction," as used herein, refers to the introduction of one or more exogenous polynucleotides into a host cell by using physical or chemical methods. Many transfection techniques are known in the art and may include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al, *Mol. Cell Biol.*, 7: 2031-2034 (1987)).

While the methods of this disclosure may be performed using a cell (either in vivo or in vitro), the method also may be performed using a cell-free gene expression system. A "cell-free gene expression system" refers to a composition comprising all of the elements required for transcription and translation of a nucleic acid sequence. Such elements are known in the art and may include, for example, RNA polymerase, transcription factors, splicing factors, tRNA molecules, etc. The cell-free gene expression system may be any suitable composition that enables cell-free transcription and translation. For example, the cell-free gene expression system may comprise the transcription and translation machinery of rabbit reticulocytes, wheat germ extract, *E. coli*, or any other suitable source. Rabbit reticulocytes can translate large mRNA transcripts and carry out post-translational processing, such as glycosylation, phosphorylation, acetylation, and proteolysis. Wheat germ extract is best suited for expression of smaller proteins, and *E. coli* cell-free extracts are capable of carrying out transcription and translation in the same reaction environment. Commercially available cell-free expression compositions may include, for example, rabbit reticulocyte extracts (Promega, Madison, Wis.), pCOLADuet™ (Novagen, Madison, Wis.), EXPRESSWAY™ Linear Expression System (Invitrogen Corp., Carlsbad, Calif.), pIEx™ Insect Cell Expression Plasmids (Novagen, Madison, Wis.), and the Rapid Translation System (Roche Diagnostics Corp., Indianapolis, Ind.).

The gene of interest may encode any suitable gene product, such as an RNA molecule that is subsequently translated into a protein. The gene of interest may encode any suitable protein, including but not limited to, surface proteins, intracellular proteins, membrane proteins, and secreted proteins. In some embodiments, the gene of interest may encode an antibody heavy chain or portion thereof, an antibody light chain or portion thereof, an enzyme, a receptor, a structural protein, a co-factor, a polypeptide, a peptide, an intrabody, a selectable marker, a toxin, a growth factor, or a peptide hormone. In some embodiments, the gene of interest may encode a therapeutic protein that can be used to prophylactically or therapeutically treat a mammal for a disease. Examples of suitable therapeutic proteins may include cytokines, toxins, tumor suppressor proteins, growth factors, hormones, receptors, mitogens, immunoglobulins, neuropeptides, neurotransmitters, and enzymes, among others.

The gene of interest further may comprise expression control sequences, such as promoters, enhancers, polyadenylation signals, transcription terminators, internal ribosome entry sites (IRES), and the like, that provide for the expression of the gene of interest in a host cell. Exemplary expression control sequences are known in the art and described in, for example, Goeddel, *Gene Expression Technology: Methods in Enzymology*, Vol. 185, Academic Press, San Diego, Calif. (1990).

In some embodiments, the cell comprising the gene of interest (whether endogenous or exogenous to the cell) may be grown and maintained under conditions such that the gene of interest is expressed (i.e., transcribed) in the cell, resulting in one or more nascent RNA molecules transcribed from the gene of interest. Suitable methods and systems for in vivo and in vitro gene expression are known in the art and can be used in the context of the methods described herein (see, e.g., Goverdhana et al., *Mol. Ther.*, 12(2): 189-211 (2005); Agha-Mohammadi, S. and Lotze, M. T., *J. Clin. Invest.*, 105(9): 1177-1186 (2000); Lorkowski, S. and Cullen, P. M. (eds.), *Analysing Gene Expression, A Handbook of Methods: Possibilities and Pitfalls*, Wiley-Blackwell (2006); and *Genes and Gene Expression: The NCBI Handbook*, National Center for Biotechnology Information, Bethesda, Md. (2013)).

Following expression of the gene of interest in the cell, the methods of this disclosure may comprise isolating one or more nascent RNA molecules transcribed from gene of interest. The term "isolating," as used herein, refers to removing the one or more nascent RNA molecules from its natural environment (i.e., a cell). Nascent RNA molecules can be distinguished from more mature mRNA molecules because nascent RNA typically is enriched in the nucleus, while mRNA is enriched in the cytoplasm. Therefore, nascent RNA may be enriched for and isolated by performing a nuclear RNA extraction using commercially available kits which allow for separation of nuclear and cytoplasmic RNA from a sample. Such kits are available from a variety of sources, such as, for example, Norgen Biotek Corp. (Thorold, ON, Canada), BioCat GmgH, (Heidelberg, Germany), and Active Motif (Carlsbad, Calif.). Because RNA is unstable due to the ubiquitous presence of RNases present in many cell types, it will be appreciated that special care and precautions may be required for RNA isolation as it may be susceptible to degradation (see, e.g., L. Buckingham and M. L. Flaws, Molecular Diagnostics: *Fundamentals, Methods, & Clinical Applications*, F. A. Davis, Philadelphia, Pa. (2007); and U.S. Patent Application Publication 2002/0192667). Generally, strong denaturants are used in RNA isolation to inhibit endogenous RNases (see, e.g., Doyle, *The Source of Discovery: Protocols and Applications Guide*, PROMEGA, Madison, Wis., (1996)). RNA isolation methods may include, for example, organic extraction methods, spin basket formats, magnetic particle methods, and direct lysis methods. In organic extraction methods, a sample (e.g., a cell culture) is homogenized in a phenol-containing solution and the sample is then centrifuged. During centrifugation, the sample separates into three phases: a lower organic phase, a middle phase that contains denatured proteins and genomic DNA, and an upper aqueous phase that contains RNA. The upper aqueous phase is recovered and RNA is collected by alcohol precipitation and rehydration.

Filter-based, spin basket formats utilize membranes (usually glass fiber, derivitized silica, or ion exchange membranes) that are seated at the bottom of a small plastic basket. Samples are lysed in a buffer that contains RNase inhibitors (typically guanidine salts), and nucleic acids are bound to the membrane by passing the lysate through the membrane using centrifugal force. Wash solutions are subsequently passed through the membrane and discarded. An appropriate elution solution is applied and the sample is collected into a tube by centrifugation. Some formats can be processed by either centrifugation or vacuum using specialized manifolds.

Magnetic particle RNA isolation methods utilize small (e.g., 0.5-1 μm) particles that contain a paramagnetic core and surrounding shell modified to bind to entities of interest. Paramagnetic particles migrate when exposed to a magnetic field, but retain minimal magnetic memory once the field is removed. This allows the particles to interact with molecules of interest based on their surface modifications, be collected rapidly using an external magnetic field, and then be resuspended easily once the field is removed. Samples are lysed in a solution containing RNase inhibitors and allowed to bind to magnetic particles. The magnetic particles and associated cargo are collected by applying a magnetic field. After several rounds of release, resuspension in wash solutions, and recapture, the RNA is released into an elution solution and the particles are removed.

Direct lysis RNA isolation methods involve sample preparation utilizing lysis buffer formulations that disrupt samples, stabilize nucleic acids, and are compatible with downstream analysis. Typically, a sample may be mixed with a lysis agent, incubated for an amount of time under specified conditions, and then used directly for downstream analysis. If desired, samples may be purified from stabilized lysates. By eliminating the need to bind and elute from solid surfaces, direct lysis methods can reduce or eliminate bias and recovery efficiency effects that may occur when using other purification methods.

RNA isolation methods that may be used in the context of the inventive method are described in detail in, e.g., Peirson, S. N. and Butler, J. N., *Methods Mol. Biol.*, 362: 315-27 (2007); Bird, I. M., *Methods Mol. Med.*, 108: 139-48 (2005); and Tan, S. C. and Yiap, B. C., *J. Biomedicine and Biotechnol.*, Article ID 574398 (2009)). RNA extraction kits that may be used in the inventive method include, for example, RNAEASY™ Micro Kit (Qiagen, Hilden, Germany), TRIZOL® Reagents (ThermoFisher Scientific, Waltham, Mass.), and DIRECT-ZOL™ and QUICK-RNA™ kits (Zymo Research Corp., Irvine, Calif.).

The methods described herein may further comprise identifying introns retained in RNA molecules present in the nucleus or cytoplasm. Retained introns may cause background staining that prevents accurate resolution of allele-specific expression by in situ hybridization staining. Retained introns can be identified in cytoplasmic RNA, nuclear RNA, or both nuclear and cytoplasmic RNA. Preferably, retained introns are identified in nuclear RNA, as the nucleus is the cellular location of intron processing and the presence of retained introns in the nucleus may especially impair the resolution of allele-specific expression by in situ hybridization staining.

Once the one or more nascent RNA molecules are isolated from the cell, the present methods may comprise sequencing the one or more nascent RNA molecules. Any suitable method for determining the sequence of a nucleic acid method known in the art can be used in the context of the invention. Recently, the development of high-throughput DNA sequencing methods has led to the development of new methods for both mapping and quantifying the complete set of mRNA transcripts in a cell (i.e., the transcriptome). These methods of RNA sequencing (also referred to as "RNA-Seq") employ deep-sequencing technologies that convert a population of RNA (e.g., polyadenylated mRNA) to a library of cDNA fragments with adaptors attached to one or both ends. Each molecule of the cDNA library, with or without amplification, is then sequenced in a high-throughput manner to obtain short sequences (or short sequence "reads") from one end (single-end sequencing) or both ends (pair-end sequencing). The sequencing reads typically are 30-400 base pairs (bp) in length, depending on the DNA-sequencing technology used. Following sequencing, the resulting reads are either aligned to a reference genome or reference transcripts, or assembled de novo without the genomic sequence to produce a genome-scale transcription map that contains both the transcriptional structure and/or level of expression for each gene.

Any high-throughput sequencing technology may be employed for RNA sequencing. Such technologies are available from commercial sources such as, for example, Illumina, Inc. (San Diego, Calif.), Applied Biosystems Corp. (Foster City, Calif.), Roche Sequencing (Pleasanton, Calif.), and Helicos Biosciences Corp. (Cambridge, Mass.). RNA sequencing methods that can be used in the context of the invention also are described in detail in, for example, Nagalakshmi et al., *Science*, 320: 1344-1349 (2008); Wilhelm et al., *Nature*, 453:1239-1243 (2008); Mortazavi et al., *Nature Methods*, 5: 621-628 (2008); Lister et al., *Cell*, 133: 523-536 (2008); Cloonan et al. *Nature Methods*, 5: 613-619 (2008); Marioni et al., *Genome Res.*, 18(9): 1509-17 (2008); Morin et al., *Biotechniques*, 45: 81-94 (2008); Holt R. A. and Jones S. J., *Genome Res.*, 18: 839-846 (2008); Barbazuk et al., *Plant* 51: 910-918 (2007); Vera et al., *Mol. Ecol.*, 17: 1636-1647 (2008); Emrich et al., *Genome Res.*, 17: 69-73 (2007); Wang et al., *Nature Reviews Genetics*, 10(1): 57-63 (2009); and Wolf, J. B., *Molecular Ecology Resources*, 13: 559-572 (2013)).

The results of RNA sequencing may need to be normalized to remove technical biases inherent in the sequencing approach, such as the length of the RNA species and the sequencing depth of a sample. These biases can be corrected for by expressing RNA-Seq results in terms of reads per kilobase million (RPKM), fragments per kilobase per million (FPKM), or transcripts per kilobase million (TPM). RPKM is calculated as follows:

$$RPKM = \frac{C}{LN}$$

where C is the number of reads on a feature (e.g., a transcript, exon, etc.), L is the length of the feature (in kb), and N is the total number of reads in millions. FPKM is analogous to the RPKM calculation, but instead of read counts, the relative abundances of transcripts are described in terms of the expected biological objects (fragments) observed from an RNA-Seq experiment. RPKM may be used for single-end sequencing, while FPKM typically is used for paired-end sequencing. TPM has been proposed as an alternative to RPKM that respects the average invariance and eliminates statistical biases inherent in the RPKM measure (see, e.g., Wagner et al., *Theory Biosci.*, 131(4): 281-285 (2012)). FPKM, RPKM, and TPM can be determined using any one of a variety of algorithms that have been developed to analyze RNA-Seq data. Such algorithms may include, for example, Cufflinks (Trapnell et al., *Nat Biotechnol.*, 28: 511-515 (2010)), IsoEM (Nicolae et al., *Algorithms Mol Biol.*, 6:9 (2011)), HTSeq (Anders et al., *Bioinformatics*, 31(2):166-9 (2014)), RSEM (Li et al., *Bioinformatics*, 26:493-500 (2009); and Li B. and Dewey, C. N., *BMC Bioinformatics*, 12: 323 (2011), and featureCounts (*Bioinformatics*, 30(7): 923-30 (2014)).

Other tools for analyzing RNA-Seq expression that may be used in the methods of this disclosure may include genome mapping tools (e.g., STAR, GSNAP, MapSplice, and TopHat) and human genome annotation databases (e.g., RefSeq, CSC Known Genes, Ensembl, and GENCODE) (see, e.g., Dobin et al., *Bioinformatics*. 2013, 29(1):15-21; Wu, T. D. and Nacu S., *Bioinformatics*. 2010, 26(7):873-81; Wang et al., *Nucleic Acids Res*. 2010, 38(18):e178; Kim et al., *Genome Biol*. 2013, 14(4):R36; Pruitt et al., *Nucleic acids Res*. 2007, 35(Database):D61-65; Hsu et al., *Bioinformatics*. 2006, 22(9):1036-46; Flicek et al., *Nucleic Acids Res*. 2014, 42(Database issue):D749-55; and Harrow et al., *Genome Res.*, 2012, 22(9):1760-74).

In some embodiments, the methods may comprise determining the fragments per kilobase per millions (FPKM) for each exon and each intron present in a nascent RNA molecule. The borders between introns and exons are marked by specific nucleotide sequences within a pre-mRNA, which delineate where splicing will occur. Such boundaries are referred to herein as "splice sites" and are composed of polynucleotides that are capable of being recognized by the spicing machinery of a eukaryotic cell as suitable for being cut and/or ligated to another splice site. Splice sites allow for the excision of introns present in a pre-mRNA transcript. Typically, the 5 ' splice boundary is referred to as the "splice donor site" or the "5' splice site," and the 3 ' splice boundary is referred to as the "splice acceptor site" or the "3' splice site." Splice sites include, for example, naturally occurring splice sites, engineered or synthetic splice sites, canonical or consensus splice sites, and/or non-canonical splice sites, for example, cryptic splice sites. In addition to the 5 ' and 3' splice sites, RNA splicing also requires a third sequence called the branch point site. The branch point site typically is located entirely within an intron close to its 3' end, and is followed by a polypyrimidine tract.

Once the fragments per kilobase per million (FPKM) has been determined for each exon and each intron present in each nascent RNA molecule, the methods of this disclosure further may comprise calculating an intron retention score (IRS) for each intron of the nascent RNA using the following formula:

$$IRS = \frac{\text{intron } FPKM}{\text{mean } FPKM \text{ for two flanking exons}},$$

wherein the mean FPKM for two flanking exons is the mean FPKM for each exon directly flanking an intron of interest in the nascent RNA molecule. After the IRS score is calculated for each intron of a given nascent RNA molecule, the methods described herein may comprise ranking each intron of the nascent RNA molecule according to the intron retention score for each intron, wherein a lower intron retention score indicates that the intron is rapidly processed and a higher intron retention score indicates that the intron is not rapidly processed. Identifying rapidly processed introns within a nascent RNA molecule allows for the resolution of allele expression at the cellular level for any gene of interest. An intron is considered to be "rapidly processed" if the intron retention score for that intron is less than the mean intron retention score calculated for all of the introns in a gene of interest. The optimal rapidly processed intron for a given gene is present in all the transcripts of the gene interest and has the lowest intron retention score of all of the introns in the gene or target transcripts of interest. Once ranked, candidate rapidly processed introns may be further analyzed by visually inspecting the expression level of flanking exons relative to the rest of the exons of the gene to determine whether one exon is expressed at a significantly higher level than the other exon. In some embodiments, both flanking exons desirably are expressed at equal levels. Flanking exons that are expressed at a level that is similar to or higher than the mean expression level for all exons in the gene indicates that the target region analyzed includes a primary transcript.

This disclosure also provides methods for detecting allele-specific expression of a gene in a single cell. These methods may comprise: (a) providing a cell comprising a gene of interest, (b) expressing the gene of interest in the cell, (c) isolating one or more nascent RNA molecules transcribed from the gene of interest, (d) sequencing the one or more nascent RNA molecules isolated in (c), (e) determining the fragments per kilobase per millions (FPKM) for each exon and each intron present in the one or more nascent RNA molecules, (f) calculating an intron retention score (IRS) for each intron of the one or more nascent RNA molecules, (g) ranking each intron of the one or more nascent RNA molecules according to the intron retention score for each intron, wherein a lower intron retention score indicates that the intron is rapidly processed and a higher intron retention score indicates that the intron is not rapidly processed, (h) designing one or more nucleic acid probes that specifically bind to a rapidly processed intron identified by steps (a)-(g), wherein the one or more probes comprise a detectable label, (i) conducting RNA in situ hybridization on the rapidly processed intron using the one or more probes, and (j) detecting a signal produced by the detectable label, wherein the presence of one signal indicates that the gene of interest is expressed from one allele and the presence of two signals indicates that the gene of interest is expressed from two alleles. Descriptions of nascent RNA molecules, expression, isolation, and sequencing nascent RNA molecules, and calculation of an intron retention score, and components thereof, as set forth above with respect to the method for identifying one or more rapidly processed introns of a gene also are applicable to those same aspects of the aforementioned method for detecting allele-specific expression of a gene in a single cell.

As discussed herein, identifying rapidly processed introns within a nascent RNA molecule allows for the resolution of allele expression at the cellular level for any gene of interest. Little is known about noncanonical imprinting effects that manifest as allele expression biases at the tissue level in mammals including humans. The methods described herein provide a sensitive RNA-seq-based approach that can accurately detect both canonical and noncanonical imprinting effects in any tissue of interest at the cellular level. Following identification of one or more rapidly processed introns, as described herein, the methods may comprise designing one or more nucleic acid probes that specifically bind to a rapidly processed intron. As used herein, the term "probe" refers to an oligonucleotide that hybridizes specifically to a target sequence in a nucleic acid under conditions that promote hybridization to form a detectable hybrid. A probe may contain a detectable label which either may be attached to the end(s) of the probe or may be internally located within the probe sequence. The nucleotides of the probe which combine with the target polynucleotide need not be strictly contiguous, as may be the case with a detectable label internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within a rapidly processed intron of a nascent RNA molecule which hybridizes specifically to at least a portion of a probe oligonucleotide using standard hydrogen bonding (i.e., base pairing). A probe may comprise target-specific sequences and other sequences that contribute to three-dimensional conformation of the probe.

A probe may be designed and synthesized using routine molecular biology techniques known in the art, such as those described in, e.g., Tang et al., *Biotechniques,* 40(6): 759-763 (2006); Espelund et al., *Nuc. Acids. Res.,* 18(20): 6157-6158 (1990); Sambrook et al., *Molecular Cloning: A Laboratory Manual,* 4th ed., Cold Spring Harbor Press, Cold Spring Harbor, N.Y. (2012); and Ausubel et al., *Current Protocols in Molecular Biology,* John Wiley & Sons, New York (2016). RNA probes also may be designed and generated by commercial sources such as, for example, New England BioLabs, Illumina, and Advanced Cell Diagnostics, Inc.

The one or more probes desirably are used to conduct RNA in situ hybridization on a rapidly processed intron. The term "in situ hybridization" or (ISH), as used herein, refers to a technique that allows for precise localization of a specific segment of nucleic acid within a histologic (e.g., tissue) section. One of ordinary skill in the art will appreciate that ISH often is a powerful technique for identifying specific mRNA species within individual cells in tissue sections, providing insights into physiological processes and disease pathogenesis. The underlying basis of ISH is that nucleic acids, if preserved adequately within a histologic specimen, can be detected through the application of a probe that is complementary to the nucleic acid of interest, to which a reporter molecule (or label) is attached. Visualization of the reporter molecule allows localizing DNA or RNA sequences in a heterogeneous cell population, including tissue samples and environmental samples. Several different types of probes may be employed in in situ hybridization reactions, depending on the nature of the target nucleic acid sequence of interest. ISH probes include, for example double-stranded DNA (dsDNA) probes, single-stranded DNA (ssDNA) probes, RNA probes (riboprobes), and synthetic oligonucleotides (PNA, LNA) RNA probes, all of which allow for localization and assessment of gene expression.

The probe used in the methods described herein can be comprised of DNA, RNA, or synthetic oligonucleotide and can be of any suitable size. In some embodiments, the probe may be an RNA probe which comprises about 200 or more (e.g., 250 or more, 300 or more, 400 or more, 500 or more, 600 or more, or 700 or more) nucleotides, but less than about 2,000 (e.g., 1,900 or less, 1,500 or less, 1,400 or less, 1,200 or less, 1,000 or less, 900 or less, 800 or less, or 700 or less) nucleotides. In some embodiments, the probe may comprise about 250 to about 1,500 nucleotides (e.g., about 275, 350, 450, 550, 650, 750, 800, 950, 1,100, 1,250, 1,300, or 1,450 nucleotides), about 250 to 1,000 nucleotides (e.g., about 250, about 375, about 400, about 575, about 675, about 775, about 850, about 900, about 950, or about 975 nucleotides), or a range defined by any two of the foregoing values. It will be appreciated that probes comprising approximately 800 nucleotides may exhibit the highest sensitivity and specificity.

The one or more probes may comprise any detectable label suitable for use in in situ hybridization reactions. Examples of such labels include, but are not limited to, radioactive labels (e.g., $^3$H, $^{32}$P, $^{33}$P, $^{35}$S) or non-radioactive labels such as, for example biotin, alkaline phosphatase, digoxigenin, and fluorescent dye (FISH). In some embodiments, the RNA ISH reaction may be performed using one probe comprising one detectable label. In another embodiment, the RNA ISH reaction may employ two or more probes (e.g., 2, 3, 4, 5 or more probes), each of which may comprise a different detectable label, which allows for simultaneous detection of two or more transcripts of interest. In addition, RNA in situ hybridization may be performed on any type of tissue section suitable for ISH, including, for example, frozen tissues sections, paraffin embedded tissue sections, and/or cells in suspension. Frozen tissue sections may be prepared by snap freezing fresh tissue (rapidly in a −80° C. freezer) followed by embedding frozen tissue in a support medium for thin cryosectioning. The resulting cryosections are lightly and rapidly fixed in 4% paraformaldehyde just prior to processing for hybridization. To prepare paraffin embedded tissue sections, sections may be fixed in formalin then embedded in wax (paraffin sections) before being sectioned. Cells in suspension may be prepared by cytospinning cells onto glass slides followed by fixation with methanol.

In general, in situ hybridization reactions may involve the following steps: probe selection, tissue or sample preparation, pre-hybridization treatment, hybridization and washing, and detection and control. A probe hybridizes to a target sequence at elevated temperature, and then excess probe is washed away (after prior hydrolysis using RNase in the case of unhybridized, excess RNA probe). Reaction parameters such as temperature, salt, and/or detergent concentration may be manipulated to remove any non-identical interactions (i.e., only exact sequence matches will remain bound). Following hybridization and washing, the inventive method further comprises detecting a signal produced by the detectable label, wherein the presence of one signal indicates that the gene of interest is expressed from one allele and the presence of two signals indicates that the gene of interest is expressed from two alleles. Detecting a signal produced by the label allows for localization of the probe in the tissue sample, and the signal may be quantified using autoradiography, fluorescence microscopy, or immunohistochemistry, depending on the label employed. In some embodiments, the method may further comprises comparing the signal produced by the detectable label to an internal control gene that exhibits biallelic expression. In this regard, the thickness of cryosectioned tissue samples may influence the number of monoallelic versus biallelic cells detected, as partially cut nuclei may appear to be monoallelic due to elimination of one allele during sectioning. Therefore, a biallelic control gene (e.g., synapsin gene for brain tissue) may allow one to determine rates of false monoallelic cells in a sample.

Methods and reagents for RNA in situ hybridization are further described in detail in, for example, Wilcox, J. N., *J Histochemistry and Cytochemistry.,* 41(12): 1725-1733 (1993); Kumar, A., *Int. J. Applied Biology and Pharmaceutical Technology,* 1(2): 418-430 (2010); Zeller et al., *Curr Protoc Mol Biol.,* Chapter 14:Unit 14.3 (2001); Wang et al., *J of Mol. Diagnostics,* 14(1):22-29 (2012); Wang et al., *J of Mol. Diagnostics,* 15(2):210-219 (2013); and U.S. Pat. Nos. 7,709,198; 8,604,182; 8,658,361; 8,951,726; 7,709,198; 8,658,361; and 7,709,198. The RNA in situ hybridization reaction described herein also may be performed using any one of a variety of commercially available systems that allow for highly sensitive and specific detection of single RNA molecules expressed in a cell. Such systems include, for example, RNAscope® Technology (Advanced Cell Diagnostics, Inc., Newark, Calif.); ViewRNA® (Affymetrix, Inc., Santa Clara, Calif.); and Stellaris® (LGC Biosearch Technologies, Petaluma, Calif.).

The methods for detecting allele-specific expression of a gene in a single cell described herein provide probes that allow for detection of RNA molecules in situ at a sensitivity level of one copy per cell. Thus, as discussed above, the presence of one signal from a detectably labeled probe indicates that a gene of interest is expressed from only one allele (i.e., monoallelic expression) in a particular cell, while the presence of two signals from a detectably labeled probe indicates that a gene of interest is expressed from two alleles (i.e., biallelic expression) in a particular cell. The amount of gene expression corresponding to a detected signal may then be determined using any suitable method known in the art for quantifying gene expression, such as, for example, microarray analysis, northern blot, reverse-transcriptase PCR (RT-PCR), quantitative PCR (qPCR), differential display, serial analysis of gene expression (SAGE), and RNA sequencing analysis (RNA-Seq) (see, e.g., Mantione et al., *Med. Sci. Monit. Basic Res.,* 20: 138-141 (2014); Schwanhausser et al., *Nature,* 473: 337-342 (2011); and Lorkowski, S. and Cullen, P. M. (eds.), *Analysing Gene Expression, A Handbook of Methods: Possibilities and Pitfalls,* Wiley-Blackwell (2006)). In a further embodiment, the number of cells in a sample which exhibit monoallelic versus biallelic expression of a gene of interest also can be determined. The degree to which a particular gene of interest exhibits a monoallelic or biallelic expression pattern, as determined using any one or combination of the above-described methods, can be used to determine whether the gene exhibits canonical or noncanonical imprinting. A gene exhibits canonical imprinting when at least 99% of expression thereof arises from one parental allele in at least one tissue type, indicating allele silencing. Imprinted genes with greater than 1% of expression arising from the repressed allele are referred to as exhibiting noncanonical imprinting, since they exhibit an allele expression bias. Unlike most canonical imprinting effects, noncanonical imprinting effects are highly tissue specific.

The methods described herein may be used in a variety of diagnostic and research applications to determine whether a subject is expressing one or both alleles for any given gene. For example, the methods may be used for diagnostic testing of allele expression in tumor samples (e.g., tumor biopsy), blood samples, or other biological samples of interest. In this manner, the inventive method may be used to diagnose human genomic imprinting disorders. In this respect, approximately 1% of all mammalian genes are thought to be imprinted in some way (see, e.g., Genetic Science Learning Center. "Genomic Imprinting" Learn.Genetics; learn.genetics.utah.edu/content/epigenetics/imprinting/). Imprinted genes may play an important role in embryogenesis, autism, cancer, obesity, diabetes, and psychological disorders (see, e.g., Butler, M. G., *J. Assist. Reprod. Genet.,* 26(9-10): 477-486 (2009); and Wilkins, J. F. and Ubeda, F., *Prog. Mol. Biol. Transl. Sci.,* 101: 401-45 (2011)). Indeed, mis-regulation of imprinted gene expression (loss of imprinting (LOI)) is observed frequently in a large variety of human tumors, and is considered the most abundant alteration in cancer (Jelini, P. and Shaw, P., *J. Pathol.,* 211(3): 261-268 (2007); and Joyce, J. A., and Schofield, P. N., *Mol. Pathol.,* 51(4): 185-190 (1998)).

The methods also may be used to perform large-scale genetic screening to identify whether allele-specific expression effects occur in specific diseases of interest. For example, many human disorders are caused by heterozygous mutations in one allele, and subpopulations of cells that only express one allele could be at greater risk for disease if that allele is mutated. The methods described herein also can be used in drug screening assays.

For example, the methods described herein can be used to screen for agents (e.g., small molecules or drugs) that can change allele-specific expression for one or several genes in cells (e.g., agents that change cellular gene expression from monoallelic to biallelic or from biallelic to monoallelic). The methods described herein also can be used to identify gene expression biomarkers of disease risk and/or status based on biallelic or monoallelic expression of genes in blood cells and/or tissue biopsies, optionally in combination with genome sequence data that indicates mutated and/or healthy genomic loci. The methods described herein also can be used as a diagnostic or prognostic tool to assess disease risk or determine the inheritance pattern of a particular disease. Any disease that is affected, or potentially affected, by imprinting effects (either canonical or noncanonical), may benefit from the application of the inventive methods for diagnostic/drug discovery. Examples of such diseases include, but are not limited to, Prader-Willi syndrome, Angelman syndrome, Silver-Russell syndrome, Beckwith-Wiedemann syndrome, Albright hereditary osteodystrophy, uniparental disomy, certain types of cancer, autism, schizophrenia, obsessive-compulsive disorder (OCD), attention-deficit hyperactivity disorder (ADHD), bipolar affective disorder (BPAD), Klinefelter syndrome, Turner syndrome, diabetes, and obesity.

EXAMPLES

The following examples further illustrate the invention but, of course, should not be construed as in any way limiting its scope. Data relating to deep sequencing, transcriptome-wide imprinting analysis, autosomal gene imprinting analysis (1% FDR cutoff), candidate canonical and noncanonical imprinted gene clusters, pyrosequencing, and analysis of noncanonical imprinted genes in wild-derived mouse trios described below are included on the CD-ROM submitted herewith, which is incorporated by reference in its entirety herein.

Example 1

This example demonstrates a method for identifying SNPs that distinguish between Cast and B6 alleles.

Adult female F1 hybrid offspring were generated from reciprocal crosses of CastEiJ (Cast) and C57BL/6J (B6) inbred strains, and the transcriptome of the initial (F1i: Cast mother×B6 father) and reciprocal (F1r: B6 mother×Cast father) hybrid offspring were evaluated by RNA-seq. Base calls at single nucleotide polymorphism (SNP) sites were used to distinguish expression from maternal and paternal alleles (Gregg et al., *Science,* 329: 682-685 (2010), Gregg et al., *Science,* 329: 643-648 (2010)).

Many advances were made to improve the methodology for detecting imprinting effects as detailed in FIG. 1. For each tissue analyzed, specifically the arcuate nucleus (ARN), dorsal raphe nucleus (DRN), liver, and muscle, eight to nine biological replicates were performed for each cross. The ARN, DRN, liver and thigh muscle were microdissected from female F1 hybrid mice at 8-10 weeks of age. To analyze SNPs in the parents, these tissues were dissected from C57BL/6J and CastEiJ breeders at approximately 6 months of age following the birth of litters. The ARN dissection includes the ventral medial hypothalamus. The DRN dissection includes portions of the ventral periaqueductal grey. The tissues were stored in RNAeasy Kit lysis buffer (Qiagen) at −80° C. until the RNA was extracted using the RNAeasy Micro Kit (Qiagen). RNA was pooled from 4-5 daughters from different litters to provide ~3 of total RNA for each biological replicate. To reduce variance related to dissections and to maintain library complexity, the RNA was pooled equally from 4-6 animals for each biological replicate and libraries were constructed from ~2-3 µg of total RNA. This approach reduced technical variance related to the microdissection of the tissues, provided additional statistical power by including more animals in the analysis, and increased the complexity of the starting library, since a single animal only yields ~0.5 µg of RNA from the arcuate nucleus (ARN) or the dorsal raphe nucleus (DRN). Samples were prepared for RNASeq using the TruSeq RNA sample preparation kit v2 (RS-122-2001, Illumina). Single-end sequencing of the libraries was performed using the HiSeq 2000 (Illumina). Deep sequencing was then performed, generating 80-100 million, 59 bp single-end reads per replicate. The acquisition of large numbers of reads (increased sampling) was performed to accurately assess allele-specific expression effects for genes with lower expression levels. In total, 68 RNASeq datasets were generated with this approach to analyze imprinting effects in the ARN, DRN, liver and muscle.

To develop a sensitive and accurate approach, SNP sites that accurately discriminate between the expression of Cast and B6 alleles were first defined. SNPs and indels that differentiate the Cast and B6 mouse strains have been publically annotated based on genome sequence data. However, technical effects related to library prep and read alignment, and biological effects related to genetic drift and RNA editing, could impact the fidelity of these sites for the measurement of allele-specific expression levels in the RNASeq data. Therefore, to first define a set of high fidelity SNP sites, RNASeq was performed on the ARN, DRN, liver, and muscle from the Cast and B6 mothers and fathers used to generate the Fli and Flr offspring in the breeding colony. The B6 parent transcriptome data was aligned to the mm9 reference genome and methods implemented in SamTools were used to define polymorphic sites (Li, Bioinformatics, 27: 2987-2993 (2011); Li, Bioinformatics, 27: 1157-1158 (2011); Li et al., Bioinformatics, 25: 2078-2079 (2009)). This analysis defined 86,335 sites that were heterozygous or homozygous at the transcriptome level relative to the mm9 annotated genome sequence in the B6 breeders; subsequently all of these variant sites were omitted from the study. Next, the Cast parent transcriptome data was aligned to the mm9 genome sequence, which identified over 1 million heterozygous or homozygous sites; again, all of the heterozygous sites, as well as all indels and SNP sites within 59 bp (one read length) of an indel, were omitted. Further analysis was then focused on the remaining homozygous SNP sites.

Figure 1C:
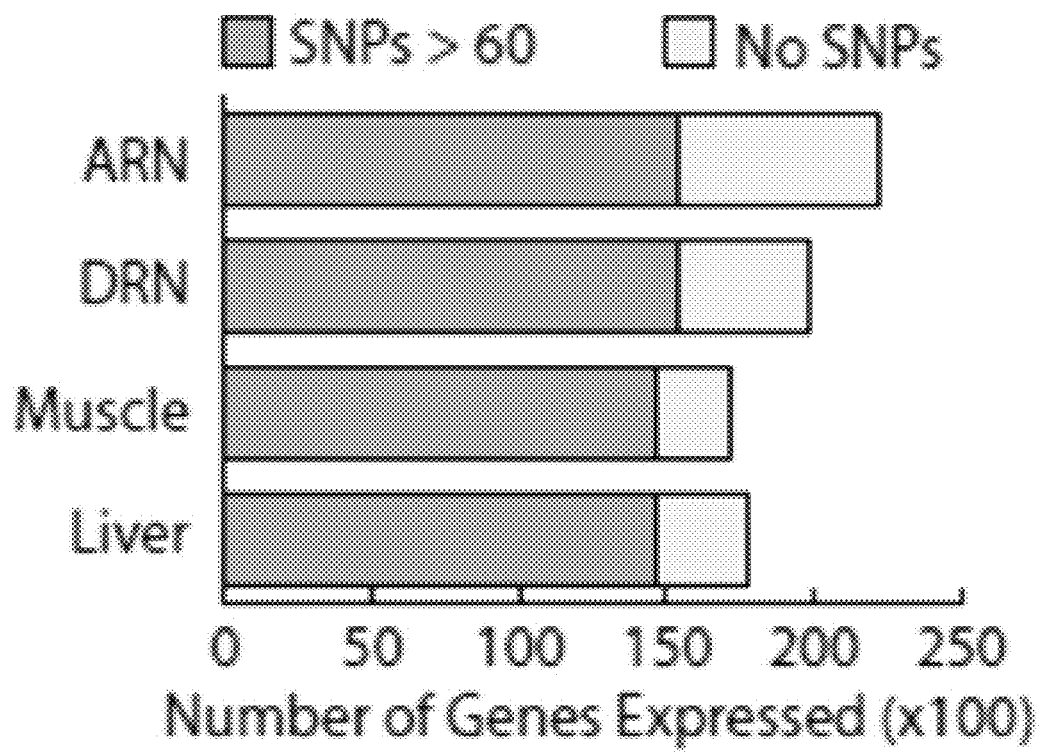
FIG. 1C is a bar graph showing the number of genes expressed in each tissue type, and the proportion with SNPs that have a quality score greater than or equal to 60.
Figure 1D:
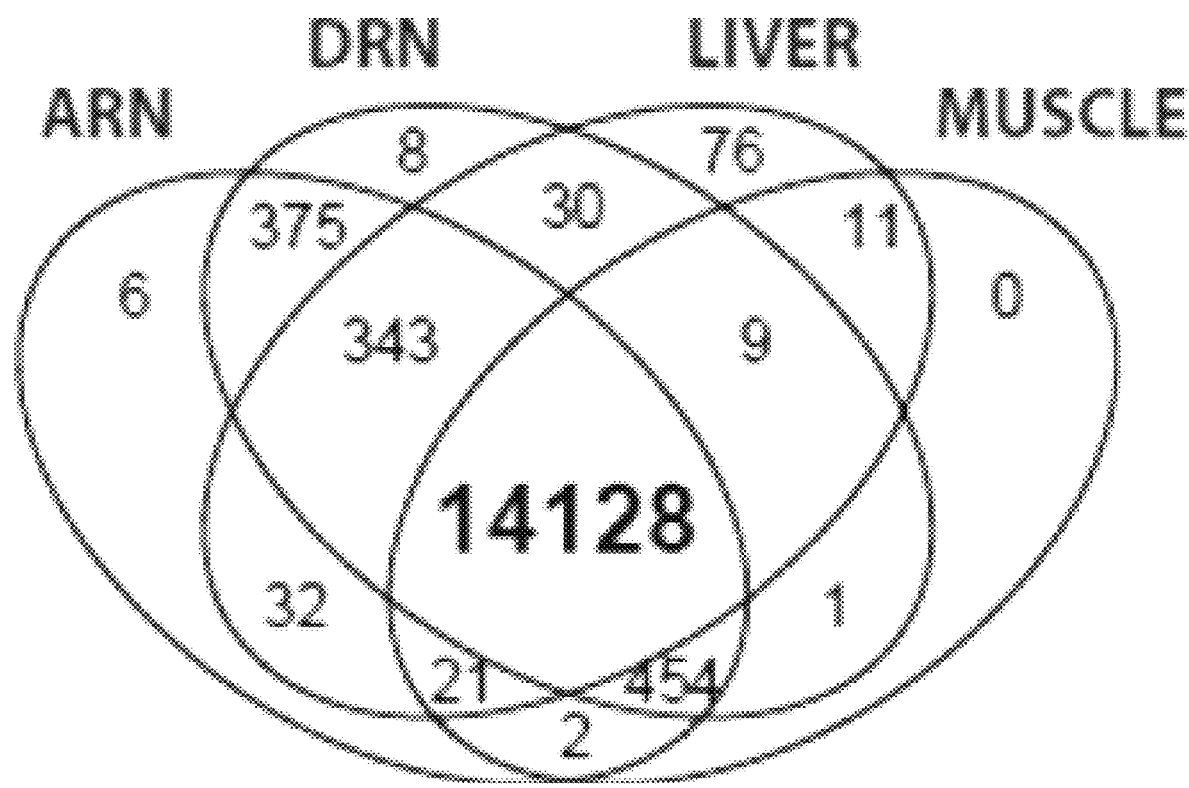
FIG. 1D is a Venn diagram showing the number of genes assessed for imprinting in each tissue type.
Figure 1E:
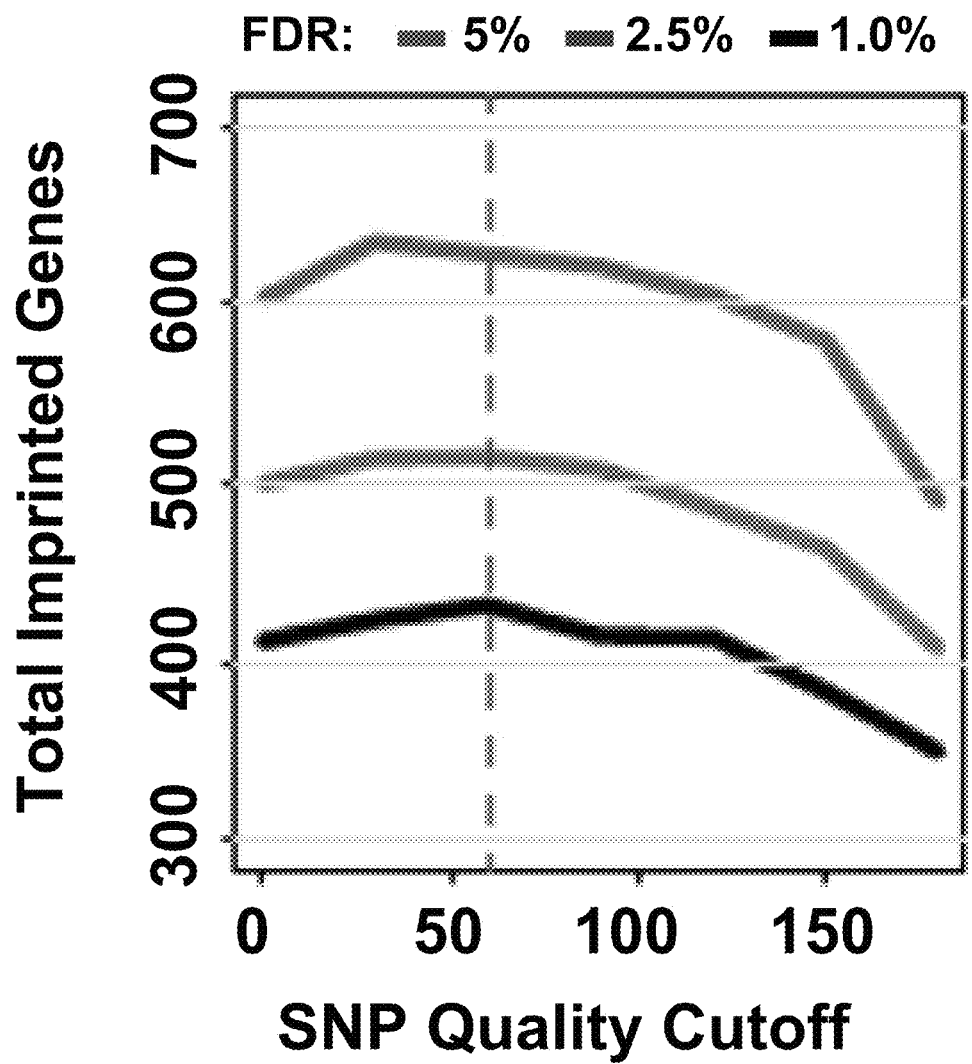
FIG. 1E and FIG. 1F are line graphs showing that a SNP quality score cutoff of 60 maximizes the sensitivity to detect imprinting effects at the 1% FDR cutoff (E) and increases the sensitivity to detect imprinting for X-linked genes compared to less stringent SNP quality cutoffs (F).

SamTools was used to compute a statistical quality score for each variant site. By enforcing a stringent SNP quality score cutoff of 60, a table of 400,820 SNP sites was constructed that permits an analysis of allele-specific expression effects in the data. Greater than 99% of these SNPs w present in the publically annotated variant files for Cast and B6 genomes, which confirms the fidelity of the SNP sites between the genome and transcriptome data. For this SNP set, it was found that 93% of SNP sites located greater than 59 bp (one read length) apart from each other in the same imprinted gene (1% FDR) agreed in terms of the direction of the parental bias (based on ARN, FIG. 1B). The mean number of SNPs per imprinted gene was 11 at this cutoff (FIG. 1B), and imprinting was evaluated for 68% of genes expressed in the ARN, 77% in the DRN, 85% in the muscle, and 82% in the liver (FIG. 1C). In total, the imprinting effects for 15,496 genes were analyzed in the mouse genome, 91% of which were expressed in all four tissues (FIG. 1D). Thus, the SNP set yields excellent coverage and reproducibility between SNPs in the same gene for imprinting effects. It was further found that this SNP set slightly improved the sensitivity to statistically detect imprinting effects in the data at a stringent 1% FDR compared to lower quality score cutoffs (FIG. 1E). The same finalized reference SNP set was used for the analysis of imprinting in each tissue type.

Figure 1F:
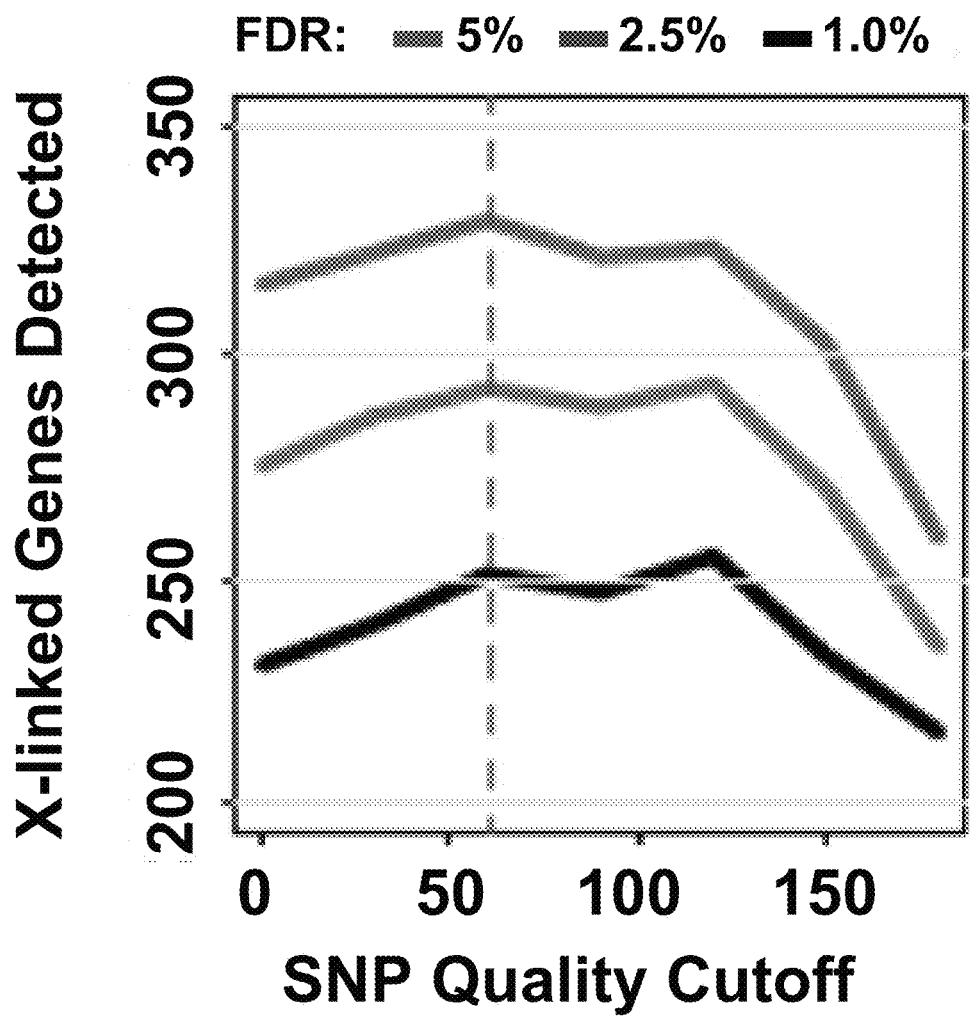

Next, a method was developed to evaluate the SNP set based on internal controls for noncanonical imprinting effects. Maternally-inherited mitochondrial genes or known canonical imprinted genes could serve as internal controls, but these genes exhibit complete allele silencing and are therefore not representative of noncanonical imprinting effects. Previous studies have demonstrated that parent-of-origin effects influence X-inactivation (Chadwick et al. Mamm. Genome, 16: 691-699 (2005); Fowlis et al., Genet. Res., 58: 63-65 (1991)) and that a bias exists to express the maternally inherited X chromosome (Xm) in female mice (Calaway et al., PLoS Genet. 9: e1003853 (2013); Gregg et al., Science, 329: 682-685 (2010); Wang et al., Genome Biol., 11: R79 (2010)). It was reasoned that this maternal X chromosome bias could serve as a powerful internal control to evaluate the detection of noncanonical imprinting effects involving an allele bias. It was determined that between 80-90% of ~500 X-linked genes analyzed in this study exhibited a maternal bias in each of the four tissue types (FIG. 3A). Histogram plots of the distribution of p-values for imprinting effects for X-linked genes indicated that the Xm bias is statistically detected in the data for most genes (FIG. 3B, and see below for statistical methods). Thus, by evaluating the proportion of maternally biased X-linked genes that are discovered at specific p-value cutoffs, insights are gained into whether different parameters, such as the SNP quality score improve the signal-to-noise in the data by increasing or decreasing the proportion of maternally biased X-linked genes detected. Importantly, it was found that the SNP set yields improved detection of the maternal bias for X-linked genes compared to SNP quality score cutoffs less than 60 (FIG. 1F). Increasing the stringency of the quality score to cutoffs higher than 60 did not improve the signal: noise characteristics of the data at 1%, 2.5% and 5% controlled FDRs (FIG. 1F).

Figure 1G:
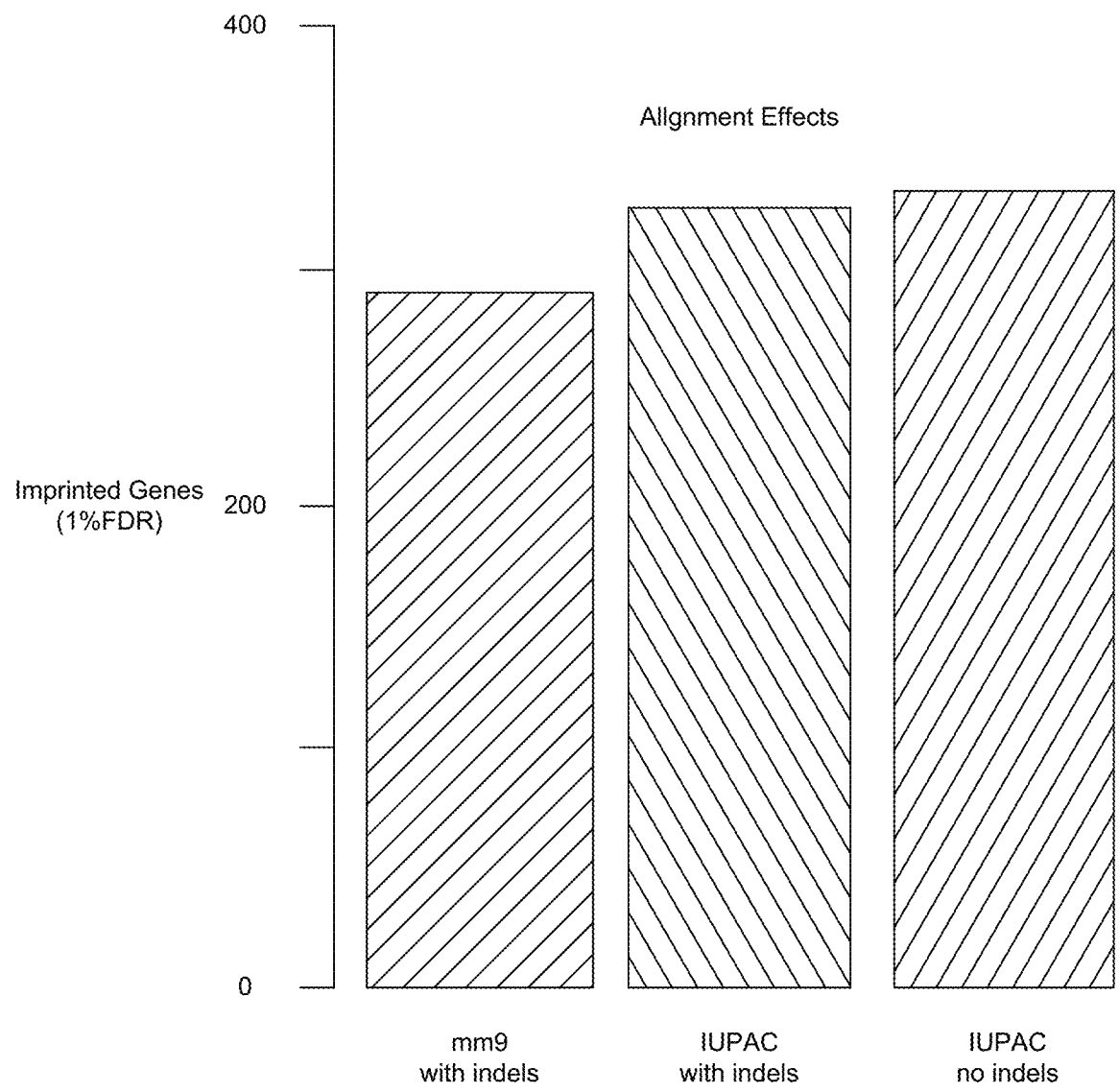
FIG. 1G is a bar graph showing the total number of imprinted genes discovered at a 1% FDR following alignment to the mm9 genome (first bar) versus alignment to an unbiased reference genome with IUPAC codes for Cast versus B6 SNP sites (second and third bars).
Figure 1H:
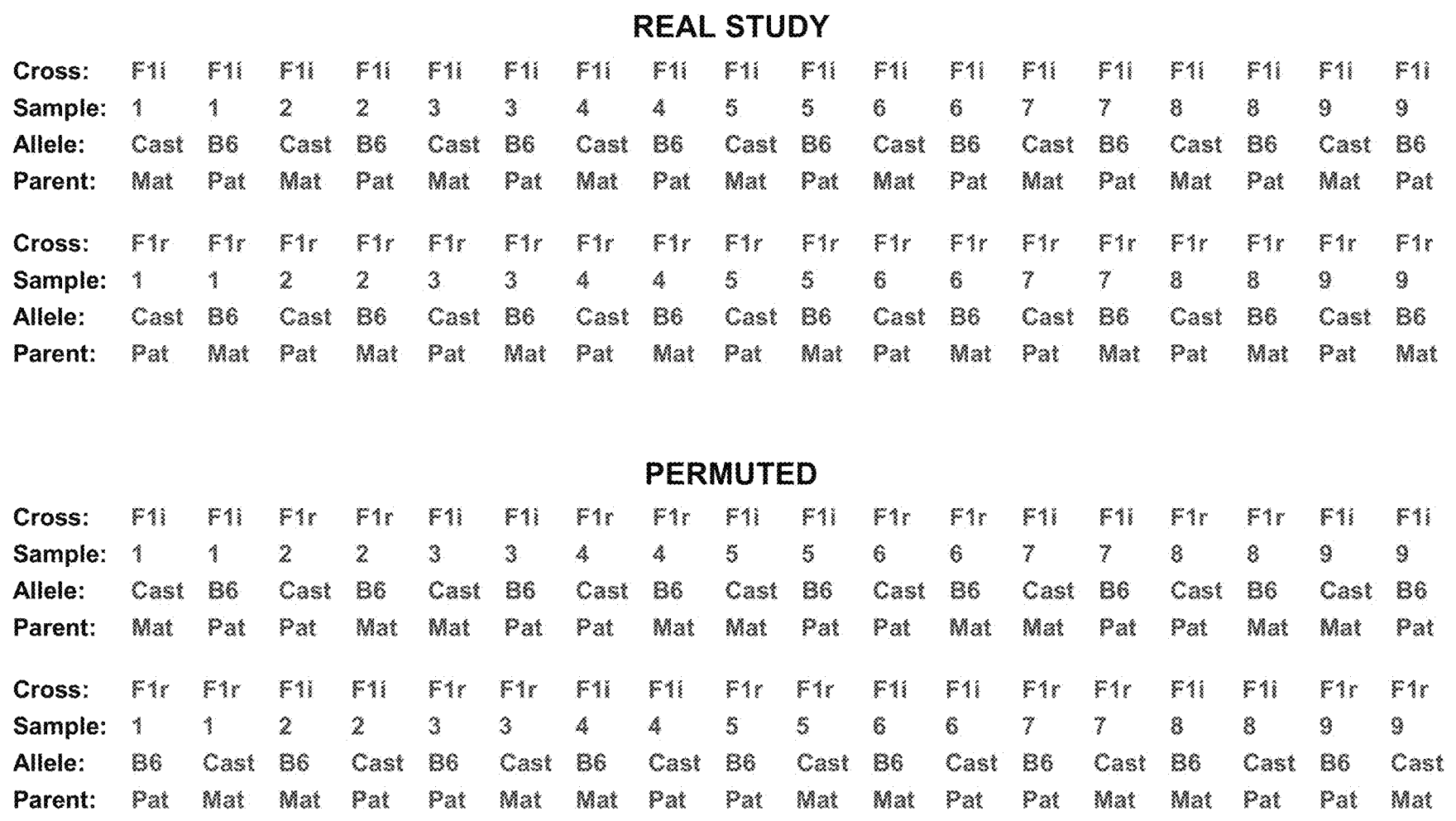

Novalign was used for the alignment of the Fli and Flr hybrid offspring RNASeq data, which allows for the incorporation of IUPAC base codes at polymorphic sites in the reference genome sequence, thereby reducing alignment biases and allowing for the utilization of a synthetic genome that incorporates both Cast and B6 sequence information. This alignment strategy improved the sensitivity to detect imprinting effects by ~11% compared to aligning to the mm9 reference genome sequence. The sensitivity to detect imprinting was further increased by omitting regions containing indels, which cannot be accommodated by IUPAC codes (FIG. 1G). While improving the sensitivity to detect imprinting effects compared to aligning to the B6 genome, this alignment strategy did not change the proportion of maternally biased X-linked genes detected as a fraction of all imprinted genes detected at different p-value cutoffs, indicating that the specificity is largely unchanged by these different alignment strategies (not shown). This analysis only included reads with unique alignments and excluded reads with multiple alignments.

To quantify allele-specific expression and imprinting effects, a custom analysis pipeline was generated that tallied the total number of Cast and B6 allele reads for each ensemble-annotated gene based on the SNP set. Due to the fact that a single read can cross multiple SNP sites, this approach was adjusted to ensure that each read is tallied only once and the tallies were summed together across all SNPs for a given gene to arrive at a gene-level analysis. To statistically define imprinting effects across F1i and F1r biological replicates for each tissue, a generalized linear modeling (glm) approach was used that was implemented in the statistical package edgeR (McCarthy et al., *Nucleic Acids Res*, 40: 4288-4297 (2012); Robinson et al., *Bioinformatics*, 26: 139-140 (2010)). This approach tested for a main effect of the parent by contrasting the full model: (allele counts sample (1, 2, 3 . . . 18)+strain (Cast versus B6)+ parent (maternal versus paternal)) to the reduced model (allele counts~sample+strain). Thus, the approach absorbs variance in the data related to sample effects and strain-specific allelic effects. This was important since most autosomal and X-linked genes exhibit a Cast or B6 allele bias due to genetic strain effects. It was found that this glm implementation in edgeR had increased sensitivity and specificity for the detection of imprinting effects compared to other statistical methods tested. In this approach, normalization factors for library size are computed from the entire raw read count dataset and then applied to the allele count dataset in the DGEList object. To estimate type I statistical errors (FDR) in the data at different p value cutoffs, an FDR estimation approach was devised that involved randomly permuting the allele-specific expression data. In this approach, data was intermingled from F1i and F1r samples in each permutation, which has the effect of scrambling the parental origin of the samples relative to the glm design matrix (FIG. 1H). For each permutation, the number of false positives was calculated at different p-value cutoffs, which reached a plateau after ~500 iterations. Therefore, for each dataset, this approach was used to calculate the mean number of false positives detected at each p-value cutoff and compared this to the actual number of genes detected in order to estimate the FDR (false/actual) (FIG. 1). In practice, this approach yielded results that were slightly more conservative than the Benjamini-Hochberg (BH) correction method for the DRN, liver and muscle datasets and similar to the BH method for the ARN dataset.

Finally, a method was devised to estimate type II statistical errors (false negatives) in the data. In the past, studies have used known canonical imprinted genes (Wang et al., *PLoS ONE*, 3: e3839 (2008)) or X-linked genes in males as internal positive controls (Gregg et al., *Science*, 329: 643-648 (2010)). However, these effects involved allele-specific silencing, and are therefore were not appropriate internal controls for the detection of noncanonical imprinting effects. As introduced above, the devised approach took advantage of the Xm expression bias that occurs in female mice and was clearly detected in the ARN, DRN, muscle and liver in this study (FIG. 3A and FIG. 3B). Thus, insights were gained into the type II statistical errors at different p value cutoffs by determining the proportion of maternally biased X-linked genes that were detected. For example, in the ARN at a controlled FDR of 1%, ~35% of the expressed and maternally biased X-linked genes were detected in this tissue (FIG. 3C). Therefore these internal controls suggested that screening for noncanonical imprinting effects was not saturated.

Example 2

This example demonstrates the identification of imprinted genes in the brain, liver, and muscle of adult female mice.

As discussed in Example 1, the offspring from the Cast× B6 crosses were analyzed for tissue-specific imprinting effects in the arcuate nucleus (ARN), dorsal raphe nucleus (DRN), liver, and muscle. The number of imprinted genes was determined across a range of p value cutoffs ($p=1\times10-6$ to $p=0.1$) (FIG. 2A), and revealed that hundreds of genes exhibited significant imprinting effects in the ARN and DRN (FIG. 2A), but fewer existed in the muscle and very few in the liver (FIG. 2B). For each data set, the p value cutoff that yields a conservative 1% false discovery rate (FDR) was identified to define a high confidence set of imprinted genes (FIG. 2A to FIG. 2C). A total of 328 imprinted genes were identified in the ARN, of which 158 were autosomal and 170 are X-linked (FIG. 2C). Additional, it was found that the ARN had 79% more autosomal imprinted genes than the DRN (93 imprinted genes), 110% more than the muscle (75 imprinted genes), and over 5-fold more than the liver (30 imprinted genes) (FIG. 2C and FIG. 2D). Out of the 69 imprinted genes detected specifically in the ARN (FIG. 2D), 48 genes (70%) showed the same direction of allele bias in the DRN, but the magnitude of the bias was stronger in the ARN (ARN mean allele bias, 65%; DRN mean allele bias, 16%).

This analysis uncovered autosomal imprinting effects that were specific to each tissue type (FIG. 2D). It was found that there were over twice as many autosomal imprinted genes in the brain (ARN+DRN: 172 genes) compared to the nonneural tissues (muscle+liver: 83 genes), which was statistically significantly ($p=7.5\times10-5$, Fisher's exact test) (FIG. 2E). At the 1% FDR cutoff, 198 X-linked genes were further detected, and 75% of these were specifically identified in the ARN (170 X-linked genes) (FIG. 2C and FIG. 2F). Thus, both autosomal and X-linked imprinting effects are enriched in the brain, and highly enriched in the ARN.

A list was compiled of the 151 accepted imprinted genes from available public repositories (Schulz et al., *Epigenetics*, 3: 89-96 (2008)), and 98 were found to be ENSEMBL-annotated for the mouse. From this list, it was determined that 142 of the 209 autosomal imprinted genes identified were not among the previously annotated imprinted genes, while 66 were known. Approximately 79% of the unannotated imprinted genes were found in the brain only (FIG. 2E). To determine whether these tissue differences are specific to imprinting, allele expression effects were analyzed in the hybrid data that arose due to genetic differences between Cast and B6 alleles (strain effects). Strain effects were statistically detected with a generalized linear model (glm) that tests for a main effect of the strain of the allele, rather than the parental origin. This approach revealed that the majority of autosomal and X-linked genes exhibited a significant bias to express either the Cast or B6 allele in each tissue (FIG. 2G, 1% FDR). Thus, the tissue differences for imprinting, which involved enrichments in the brain and a paucity of effects in the liver, do not occur for strain-related genetic allelic effects.

Insights were gained into the sensitivity of these methods by taking advantage of the known Xm expression bias in somatic tissues of female mice (Calaway et al., *PLoS Genet.* 9: e1003853 (2013); Chadwick et al. *Mamm. Genome*, 16, 691-699 (2005); Fowlis et al., *Genet. Res.*, 58: 63-65 (1991); Gregg et al., *Science*, 329: 682-685 (2010); Wang et al., *Genome Biol.*, 11: R79)). Between 80%-90% of X-linked genes exhibited a maternal allele expression bias in each of the four tissue types (FIG. 3A and FIG. 3B). With a 1% FDR cutoff, it was found in the ARN that 170 (35%) of the 492 total expressed and maternally biased X-linked genes were statistically detected as imprinted (FIG. 3C). In the DRN, 38

(8%) of the 499 maternally biased X-linked genes were detected. For the liver and muscle, only three (0.7%) and 12 (2%) of the 421 and 414 maternally biased X-linked genes were detected, respectively. By relaxing the cutoff to a 20% FDR, the maternal bias was statistically detected for over 70% of maternally biased X-linked genes in the ARN and DRN. Thus, at the 1% FDR cutoff, this screen is not saturated and is powered to discover imprinting effects that are similar to the most robust maternally biased X-linked genes in the ARN.

Example 3

This example demonstrates a comparison of canonical and noncanonical imprinting effects.

A comparison was done on the prevalence of autosomal canonical versus noncanonical imprinting effects. Canonical imprinted genes were defined as those that have at least 99% of expression or more arising from one parental allele in at least one tissue type, indicating allele silencing. The Illumina sequencing error rate is estimated to be ~0.01%-0.1% (Loman et al. *Nat. Biotechnol.*, 30: 434-439 (2012); Meacham et al., *BMC Bioinformatics*, 12: 451 (2011)), and there is a one in four chance that an error will result in a B6 read being assigned as a Cast read (or vice versa) at a given SNP site. Thus, the 1% expression cutoff for allele-silencing effects is slightly higher than the expected background of ~0.025%. All imprinted genes were classified with greater than 1% of expression arising from the repressed allele as noncanonical, since they exhibited an allele expression bias. For example, Peg3 is a canonical imprinted gene that expresses the paternal allele and silences the maternal allele in all tissues types (FIG. 4A). In contrast, Agog is a noncanonical imprinted gene that exhibits a bias to express the maternal allele in the ARN and DRN but not the liver or muscle (FIG. 4B). A total of 24 canonical imprinted genes were found that exhibited allele silencing in at least one tissue (FIG. 4C). In contrast, 186 autosomal genes were found that exhibited a significant bias to express either the maternal or paternal allele, and 142 of these had not previously been annotated (FIG. 4D). Therefore, noncanonical imprinting effects are ~8-fold more prevalent than strict canonical imprinting effects.

Interestingly, 79% of canonical imprinted genes were expressed and imprinted in both neural and non-neural tissues (FIG. 4C), but only 12% of noncanonical imprinted genes met these criteria (FIG. 4D). It was further found that 64% of noncanonical imprinted genes were specific to the brain, 20% were specific to the muscle, and only 2% were specific to the liver (FIG. 4D). Particularly striking was that 37% of noncanonical imprinted genes were specific to the ARN. Thus, unlike most canonical imprinting effects, noncanonical imprinting effects were highly tissue specific.

Canonical imprinted genes were typically located in gene clusters in the genome, which are defined by shared regulatory elements. Retrospectively, the terms "clustered" and "remote" imprinted genes were defined according to whether they were located within 1 Mb of another imprinted gene in the genome. It was found that 92% (22 out of 24) of canonical imprinted genes were located in a cluster (FIG. 4E). In contrast, only 57% of noncanonical imprinted genes were located in a cluster, while 43% resided in remote regions of the genome that were not close to other imprinted genes (FIG. 4E). In total, evidence was found for 24 candidate imprinted gene clusters on 12 chromosomes. These results reveal that noncanonical imprinting arises both near canonical imprinted gene clusters and in novel genomic regions.

Example 4

This example demonstrates that noncanonical imprinting effects may arise independently from canonical imprinting.

The results in Example 2 indicated that noncanonical imprinted genes were not simply bystanders in close proximity to canonical imprinted genes, since many reside in novel regions of the genome. Therefore the relationship between canonical and noncanonical imprinted genes was further examined. For example, Plagl1 is a canonical PEG (paternally expressed gene) in a micro-imprinted domain that is not thought to involve a gene cluster (Iglesias-Platas et al., *Nucleic Acids Res.*, 41: 2171-2179 (2013)). A neighboring gene, called Phactr2, has been previously shown to exhibit noncanonical imprinting in the mouse placenta (Wang et al., *Genetics*, 189: 109-122 (2011)). A maternal bias was uncovered for four genes near Plagl1, which include Sf3b5, Ltv1, Phactr2, and Fuca2 (FIG. 5A). Interestingly, Plagl1 exhibited canonical imprinting in all four tissues (FIG. 5B); however, the neighboring noncanonical imprinting effects were highly tissue specific. Sf3b5 and Ltv1 exhibited a maternal allele bias specifically in the ARN (FIG. 5C and FIG. 5D). Phactr2 exhibited a maternal bias in the ARN and DRN, but not the liver or muscle (FIG. 5E). Additionally, Fuca2 exhibited a maternal bias in the ARN and muscle, but not the DRN or liver (FIG. 5F). The strength of the maternal bias for these effects was not simply decreased as a function of the distance from Plagl1, since Phactr2 exhibited a stronger bias than either Sf3b5 or Ltv1.

To further analyze allele-specific expression effect, pyrosequencing was performed with the following reagents: Pyromark Gold Q24 reagents (970802, Qiagen), Pyromark Q24 cartridge (979202, Qiagen), Pyromark Q24 plate (979201, Qiagen), Pyromark Binding Buffer (979002, Qiagen), Denaturation Solution (979007, Qiagen), Pyromark annealing buffer (979009, Qiagen), Pyromark wash buffer (979008, Qiagen), streptavidin-sepharose column (17-5113-01, GE). Primers were designed using Pyromark Assay Design AW software (PyroMarkQ24 2.0.6, Qiagen). Pyrosequencing was performed and analyzed using the PyroMark Q24 system and software (Qiagen). Amplification primers and sequencing primers are provided in Table 1 for mRNA and chIP studies. For each experiment, SNP sites were identified that discriminate Cast and B6 alleles, and ~100-150 base pairs surrounding the SNP site was amplified. The sequencing primer was designed upstream of the SNP site and the ratio of Cast versus B6 base calls was determined in each sample according to the Pyromark software. 4-8 biological replicates were analyzed for each cross and the Cast:B6 allele expression (mRNA) or enrichment (chIP) ratio for each replicate was calculated. Using a one-tailed t-test for RNASeq validation studies and a two-tailed t-test for chIP studies, the Cast:B6 allele expression or enrichment ratio was compared between the Fli and Flr hybrid offspring to test for statistically significant differences between the two crosses. Significant differences in the Cast:B6 allele expression or enrichment ratio between Fli and Flr offspring arose due to parent-of-origin effects influencing Cast and B6 alleles.

TABLE 1

| Type | Gene | Preferentially Expressed Allele | One-tailed t-test H3K9ac (enriched allele) | One-tailed t-test H3K9me3 (enriched allele) | TSS location | SNP Site | Base Call | SNP position | Forward Primer | Reverse Primer | Sequence Primer |
|---|---|---|---|---|---|---|---|---|---|---|---|
| Canonical | Plagl1 | Paternal (canonical) | 0.19 (n = 3) | <0.0001 (n = 8) (Maternal) | 12810638 | chr10: 12810302 | T/C | promoter | GTGGGGATGGAGGAATCA (SEQ ID NO: 1) | Bio-GTATGCGCAAAGCCAAGGT (SEQ ID NO: 2) | GGATGGAGGAATCAATA (SEQ ID NO: 3) |
| Canonical | Meg3 | Maternal (canonical) | 0.4821 (n = 4) | <0.0001 (n = 7) (Paternal) | 110779206 | chr12: 110805719 | G/A | body | GGCCTCCTTTCAGCTTTCTGC (SEQ ID NO: 4) | Bio-CGCCCCTACTGCGTCTAGTG (SEQ ID NO: 5) | GCAGGGCTCTTCTGA (SEQ ID NO: 6) |
| Canonical | Mega12 | Paternal (canonical) | 0.0796 (n = 4) | 0.0001 (n = 8) (Maternal) | 69521865 | chr7: 69522091 | G/C | promoter | Bio-CGGTGCCAGCCAGGTAGTCAG (SEQ ID NO: 7) | GAATAGGAAGCCGGTGCAG (SEQ ID NO: 8) | GCGTGTTCCGCGGTT (SEQ ID NO: 9) |
| Non-canonical | Nhlrc1 | Paternal | 0.3565 (n = 3) | 0.0177 (n = 6) (Maternal) | 47110219 | chr13: 47110572 | C/A | promoter | GGCTAGACAGGAACAAGACAT (SEQ ID NO: 10) | Bio-AGGAAAAACACAGCAGAGAGG (SEQ ID NO: 11) | TTCAAGGGGCAGATG (SEQ ID NO: 12) |
| Non-canonical | Slc25a29 | Paternal | N.D. | 0.35 (n = 6) | 110074086 | chr12: 110074378 | C/G | promoter | Bio-GCCCAGAACCTCCCAACC (SEQ ID NO: 13) | AGCAGGAGAGTCGCATCCA (SEQ ID NO: 14) | ATACCGTGAGGGGTC (SEQ ID NO: 15) |
| Non-canonical | Eif2c2 | Maternal | 0.4409 (n = 3) | <0.0001 (n = 7) (Paternal) | 73015377 | chr15: 72935534 | C/T | body | Bio-TACACGGATACACACACCTGC (SEQ ID NO: 16) | TCATGCTAGAGGACACAGTACCA (SEQ ID NO: 17) | GCAGTTACCTGGGAAGT (SEQ ID NO: 18) |
| Non-canonical | Trappc9 | Overall Maternal (allele) | 0.0454 (n = 6) (maternal) | 0.009 (n = 6) (Paternal) | 72891634 | chr15: 72891378 | A/G | promoter | Bio-GGCCAGGAACCCCAACGC (SEQ ID NO: 19) | CTCCAGGCCTCGGCTCCT (SEQ ID NO: 20) | CGCTGTGTAAGTGCCC (SEQ ID NO: 21) |
| Non-canonical | Cdh15 | Paternal (canonical) | 0.0002 (n = 5) | 0.3738 (n = 4) (Paternal) | 125372274 | chr8: 125372570 | T/A | promoter | TGGGCCGCACTCTCTGAAG (SEQ ID NO: 22) | Bio-GGAAGCCCCTAAACACAGGACA (SEQ ID NO: 23) | CGCACTCTCTGAAGCAT (SEQ ID NO: 24) |

TABLE 1-continued

| Type | Gene | Preferentially Expressed Allele | One-tailed t-test H3K9ac (enriched allele) | One-tailed t-test H3K9me3 (enriched allele) | TSS location | SNP Site | Base Call | SNP position | Forward Primer | Reverse Primer | Sequence Primer |
|---|---|---|---|---|---|---|---|---|---|---|---|
| Non-canonical | Tgfbli1 | Maternal | 0.1128 (n = 5) | 0.0245 (n = 7) (Paternal) | 135390475 | chr7: 135390920 | G/A | promoter | Bio-GTTTCG GAGATG AAAAGG ACCTAT (SEQ ID NO: 25) | GACTTT CTTGAC CTCTGC TCTACC (SEQ ID NO: 26) | CCTGGG AGCACT CAA (SEQ ID NO: 27) |
| Non-canonical | Bcl211 | Paternal | 0.12 (n = 3) | 0.0458 (n = 8) (Maternal) | 152656453 | chr2: 152656155 | T/C | promoter | Bio-AAGACA GCCTCG GATCTG TGA (SEQ ID NO: 28) | TGTTTG TGGGGG GTCTCC (SEQ ID NO: 29) | TACGCC TCTCGG AAA (SEQ ID NO: 30) |
| Biallelic Control | Sergef | Equal | 0.2895 (n = 3) | 0.3831 (n = 6) | 46639807 | chr7: 46639931 | A/G | promoter | Bio-GAGGGG CTAATG GGACTG GA (SEQ ID NO: 31) | GTTGAG TCCCGG CGCTCT (SEQ ID NO: 32) | GGGCAG GACCAT ACC (SEQ ID NO: 33) |

Pyrosequencing confirmed that Fuca2 exhibited a significant maternal bias in the ARN, but not the liver, in Cast×B6 and PWD/J×A1J hybrid offspring (FIG. 5G). A second representative example was also examined at the Inpp5f locus (FIG. 5H to FIG. 5N). Out of the 18 gene clusters that contained canonical and noncanonical imprinted genes, 15 clusters contained maternally biased noncanonical imprinted genes only, and three contained paternally biased genes only. The Peg3-Usp29 gene cluster had both maternally and paternally biased noncanonical imprinting effects depending on the tissue, and these effects were validated for Clcn4, which was maternally biased in brain and paternal in liver.

Figure 6A:
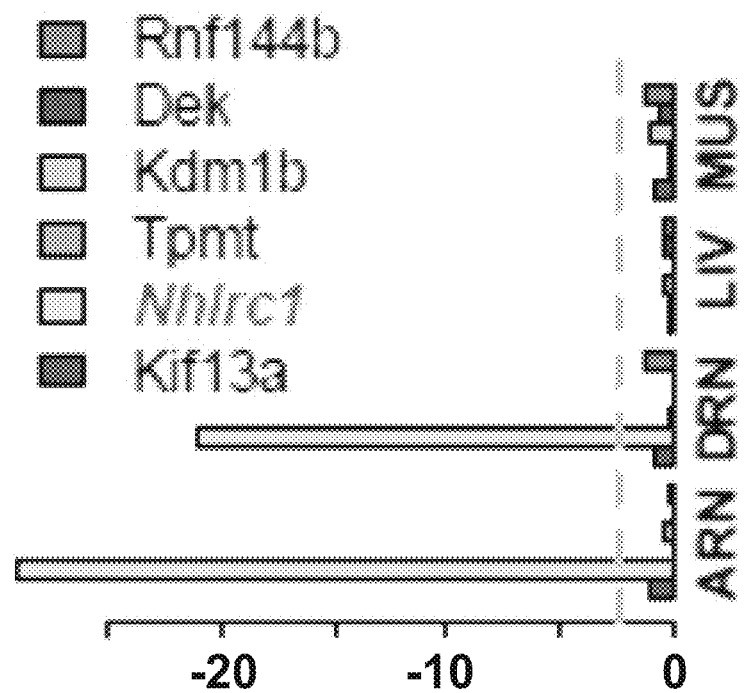
Figure 6B:
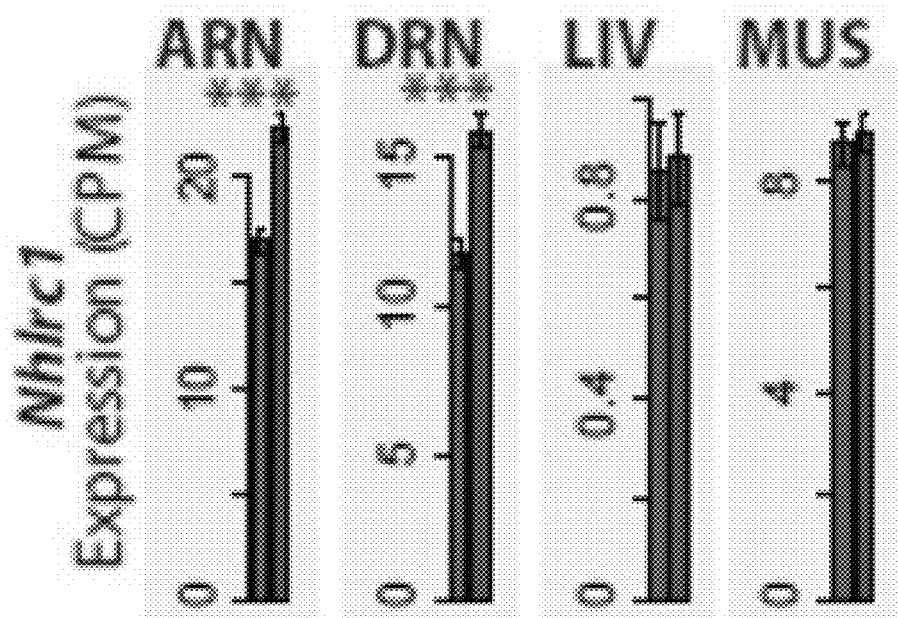
Figure 6C:
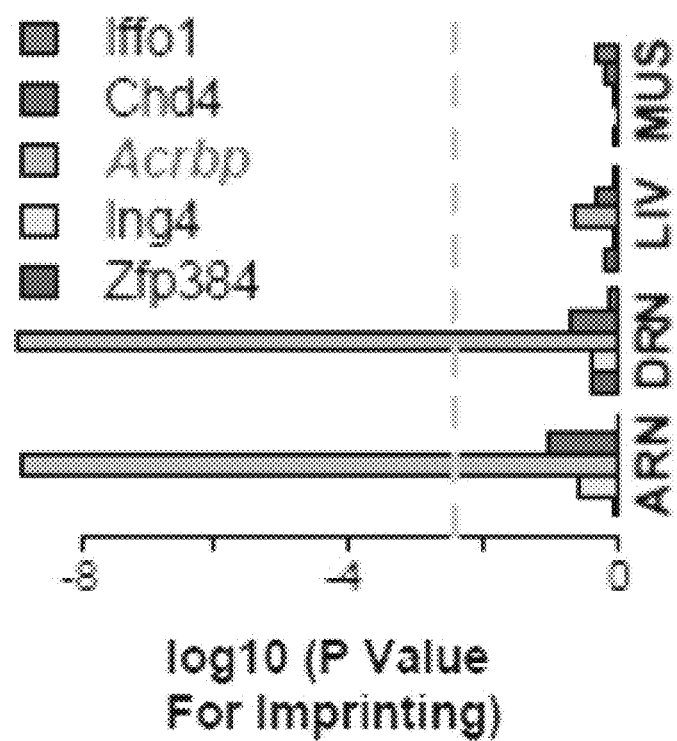
Figure 6D:
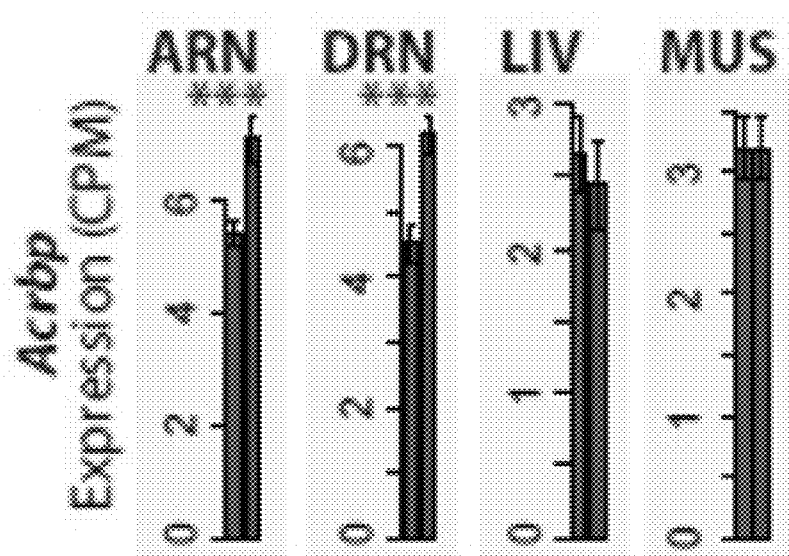
Figure 6E:
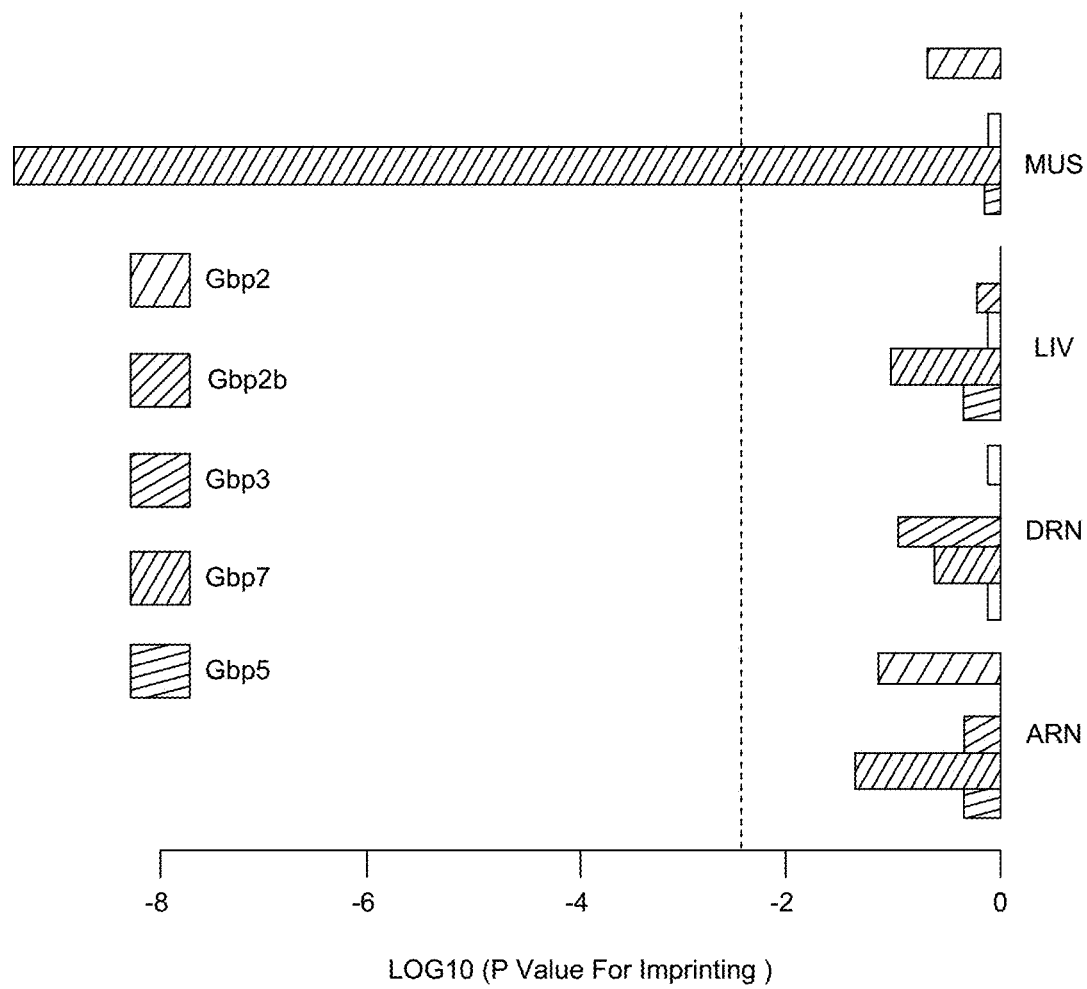
Figure 6F:
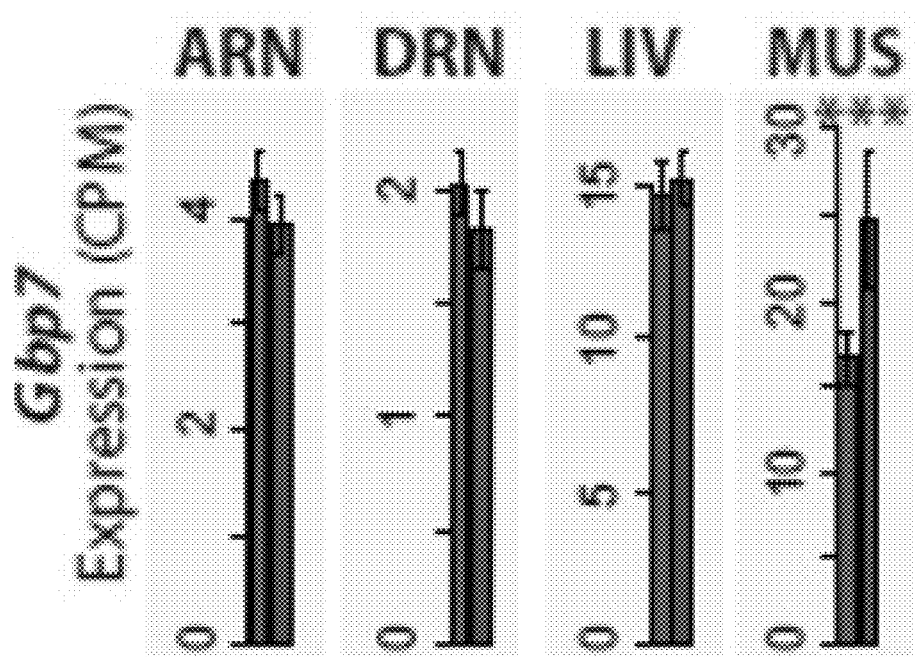
Figure 6G:
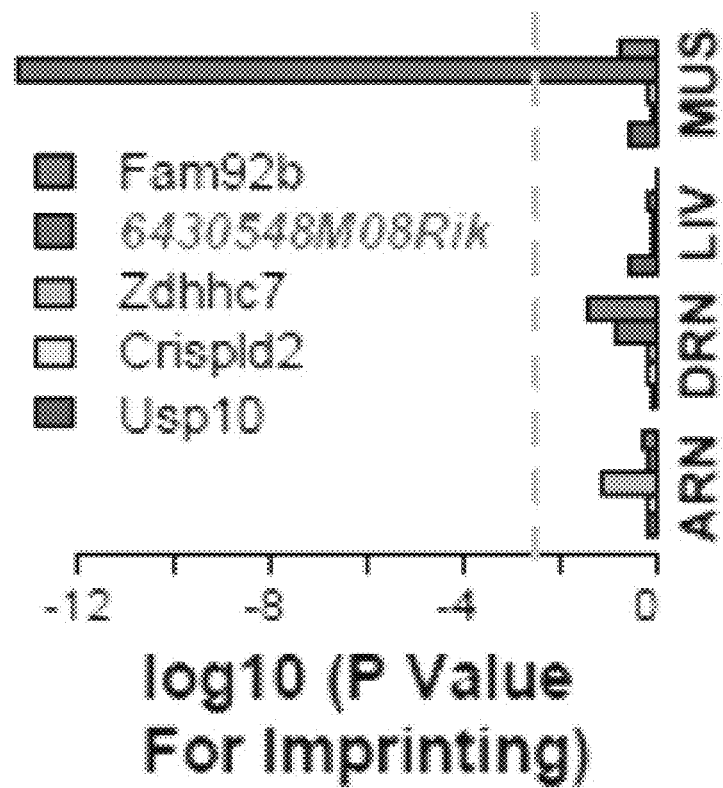
Figure 6H:
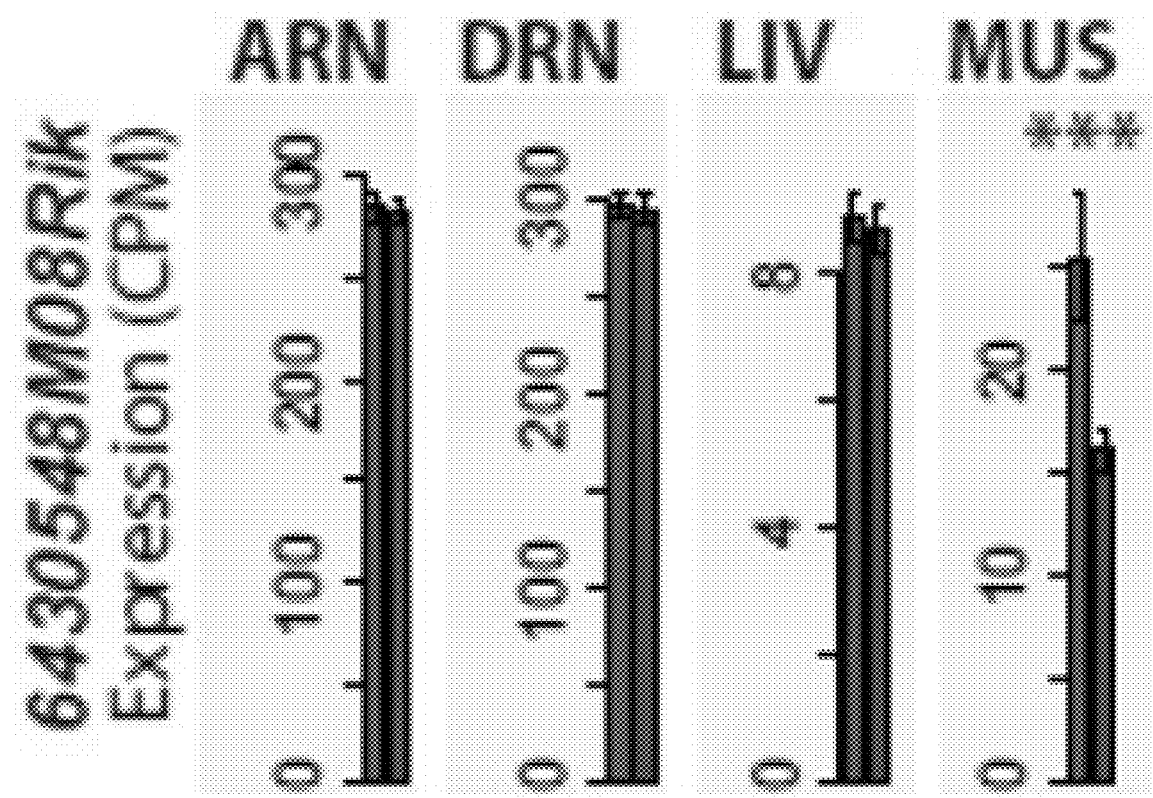

An additional 79 noncanonical imprinted genes were identified in regions of the genome that did not contain other imprinted genes (FIG. 4E). For example, Nhlrc1 was located on chromosome 13 near a differentially methylated region (Xie et al., Cell, 148: 816-831 (2012)). It was found that Nhlrc1 exhibited noncanonical imprinting involving a paternal bias in the ARN and DRN, but not the liver or muscle (FIG. 6A and FIG. 6B). The genes surrounding Nhlrc1 did not exhibit imprinting in any tissue (FIG. 6A). Similarly, Acrbp exhibits a paternal bias in the ARN and DRN, but not the liver or muscle (FIG. 6C and FIG. 6D); similar effects were also found in the muscle. For example, Gbp7 (FIG. 6E and FIG. 6F, chromosome 3) and 643054M08Rik (FIG. 6G and FIG. 6H, chromosome 8) exhibited a paternal and maternal bias, respectively, in muscle only. The neighboring genes did not exhibit imprinting in any of the tissues (FIG. 6E and FIG. 6G). Tissue-specific imprinting was confirmed for these examples and others by pyrosequencing in Cast× B6 and/or PWD/J×A/J hybrid mice. Therefore, noncanonical imprinting effects arose independently from canonical imprinting in a highly tissue-specific manner.

Example 5

This example demonstrates that noncanonical imprinting effects are reproducible in multiple genetic backgrounds.

Pyrosequencing validations were performed for 64 imprinted genes identified in the RNA-seq study, which included 62 noncanonical imprinted genes selected from a wide range of p value cutoffs in the data. These genes were assayed in one or more tissue types, and a total of 136 validation experiments were carried out involving four to eight biological replicates each. Imprinting was successfully validated for 89% (57/64) of the genes tested in at least one tissue type. Out of the 136 validation experiments performed, 106 were carried out for 57 genes using Cast×B6 hybrid mice (FIG. 7A). To ascertain whether noncanonical imprinting effects were conserved across genetic backgrounds, 30 further validation experiments were performed for 23 genes with PWD/J×A/J hybrid mice (FIG. 7A).

In the validation studies using Cast×B6 hybrid mice, 17 out of 106 pyrosequencing results disagreed with the RNA-seq results. Eight of these cases involve false-negatives in which the imprinting effect was not statistically significant by RNA-seq but was significant by pyrosequencing. Only nine cases involved potential false-positives in which imprinting was detected by RNA-seq but was not statistically significant by pyrosequencing. Finally, out of the 30 validation experiments performed in PWD/J×A/J mice, 87% (26/30 genes) agreed with the RNA-seq data from Cast×B6 hybrid mice. In total, the imprinting status was confirmed for 46/50 genes tested in the ARN, 14/14 genes in the DRN, 21/25 genes in muscle, and 20/21 genes in the liver. Tissue-specific imprinting was validated for 15 noncanonical imprinted genes that exhibited imprinting in the ARN, but not the liver, as well as seven genes that exhibited imprinting in the muscle only. Thus, the RNA-seq results are highly reproducible across different genetic backgrounds, and confirmed the tissue-specific nature of noncanonical imprinting.

It was unknown whether noncanonical imprinting effects existed in wild-derived, outbred populations. To address this issue, Idaho wild-derived mice were obtained that had been maintained in captivity as an outbred colony (Miller et al., Exp. Biol. Med. (Maywood), 227: 500-508 (2002)). Three separate parent-offspring trios were generated and RNA was harvested from the hypothalamus of each parent and one daughter for each trio, and analyzed by RNA-seq. A total of 189 genes were found to have distinguishing SNPs in all three trios and could therefore be assessed for reproducible allele-specific expression effects (FIG. 7B). Out of these 189 genes, seven were identified as noncanonical imprinted genes in the ARN of F1 hybrid mice: Asb4, Trappc9, Herc3, Ltv1, Phactr2, Cob1, and Igf2r. In the wild-derived daughters, a similar noncanonical maternal bias was found for all of these genes except Igf2r, which did not exhibit imprinting. For example, in daughter 1, Asb4, Ltv1, and Phactr2 were almost exclusively expressed from the maternal allele, and a maternal bias was present in daughters 2 and 3 (FIG. 7E and FIG. 7F). Finally, in the hybrid mice, a bias to express alleles on the Xm was also observed (FIG. 3), and to evaluate this phenomenon in the wild-derived mice, the percentage of overall expression that arises from the Xm versus the Xp in each daughter was determined. In all three wild-derived daughters, an Xm bias was found (FIG. 10H), and the bias persisted if the quality score cutoff for the SNP calls was relaxed to increase the total number of SNP sites examined, or if the stringency was increased by only analyzing sites that were homozygous between the parents. Overall, these results reveal that noncanonical imprinting effects are present in natural, outbred populations.

Example 6

This example demonstrates that tissue and gene-specific imprinting effects arise on the X chromosome.

In females, imprinting effects can arise on the X chromosome. As noted in the previous examples, at a 1% FDR imprinting effects were detected for 198 X-linked genes, and 86% of these genes (170 genes) were detected in the ARN, compared to only 20% in the DRN, 6% in the muscle, and 1.5% in the liver (FIG. 1C and FIG. 1F). Scatterplots of the mean allele bias versus the p value for imprinting for X-linked genes revealed that most X-linked genes exhibited a mean maternal bias in each of the tissues; however, the robustness of the bias appeared highly gene and tissue specific (FIG. 8A). Gene level imprinting effects are known to occur on the X chromosome; for example, Xlr3b, Xlr4b, and Xlr4c are only expressed from the Xm in some tissues (Davies et al., Nat. Genet., 37: 625-629 (2005); Raefski et al., Nat. Genet., 37: 620-624 (2005)). It was found that Xlr3a, Xlr3c, and Xlr3e exhibited the strongest maternal effects in all tissues (FIG. 8A), though the statistical scores were low due to the low expression level of these genes. Further, preferential expression of the paternal Xist allele was found in all four tissues (FIG. 8A), which was consistent with a bias to silence the Xp and express the Xm.

The scatterplots also indicated X-linked genes that exhibit maternal allele expression biases in each tissue, as well as genes that did not (FIG. 8A). For example, Hmgb3 exhibits a very modest maternal bias in the ARN and DRN, and no effect in the liver and muscle (FIG. 8A). In contrast, Il13ra1 exhibits a relatively robust maternal bias in the ARN and DRN compared to Hmgb3 (FIG. 8A). Additionally, G530011O06Rik exhibited a paternal bias in the ARN and DRN, but not in the liver or muscle. Pyrosequencing confirmed the gene and tissue-specific noncanonical imprinting effects for these genes (FIG. 8B and FIG. 8C). Pyrosequencing in Cast×B6 hybrid mice further validated brain-specific imprinting effects for the X-linked genes Maoa, Bcor, C77370, and Gspt2. Bcor and Maoa were also validated in PWD×A/J hybrid offspring, which revealed that these effects were present in different genetic backgrounds.

Twelve genes are known to escape X-inactivation in the mouse (Yang et al., Genome Res., 20: 614-622 (2010)), and it was found that these genes also appeared to exhibit tissue-specific imprinting effects (FIG. 9A). For example, Kdm6a exhibited a modest maternal bias in the ARN, but no effect in the DRN, liver, or muscle. Pyrosequencing confirmed the maternal bias in the ARN and the absence of this bias in the DRN in Cast×B6 hybrids (FIG. 9B). In PWD×A/J hybrids, a significant maternal bias for Kdm6a was found in both brain regions (FIG. 9C). Thus, genes that are known to escape X-inactivation can exhibit a maternal allele bias, though it is unclear whether the observed effects are related to gene-specific imprinting or changes to X-inactivation escape.

These results detail maternal allele biases for many X-linked genes in females (FIG. 3). The total number of maternally versus paternally biased autosomal genes in each tissue were also tallied (FIG. 9D). Interestingly, 107 more PEGs than MEGs were uncovered on chromosome 1 in the DRN, which was a statistically significant overall paternal bias (FIG. 9D, p=0.002, Fisher's exact test). These results suggested biased maternal and paternal influences over X-linked and autosomal gene expression, respectively.

Example 7

This example demonstrates that noncanonical imprinting is associated with allele-specific histone modifications.

To ascertain whether noncanonical imprinting effects detected at the transcriptome level were associated with allele-specific chromatin modifications, chromatin was isolated from the hypothalamus of Fli and Flr Cast×B6 hybrid offspring and chromatin immunoprecipitation (ChIP) was performed using the Imprint Chromatin Immunoprecipitation kit according to the manufacturer's instructions (CHP1-24RXN, Sigma-Aldrich) and the following antibodies: mouse anti-H3K9ac (ab4441, Abcam) and rabbit anti-H3K9me3 (ab8898, Abcam). Results were normalized to input controls.

This experiment targeted the transcriptionally permissive and repressive histone modifications H3K9ac and H3K9me3, respectively (Dindot et al., Genome Res., 19: 1374-1383 (2009); Singh et al., Nucleic Acids Res., 38: 7974-7990 (2010)), and focused on promoter regions by identifying SNPs within ±300 bp from the transcriptional start site for four canonical imprinted genes, six noncanonical imprinted genes, and one non-imprinted control gene (Table 1).

For the canonical imprinted genes, Plagl1 (FIG. 10A), Magel2, and Meg3 (Table 1), pyrosequencing revealed a significant enrichment for H3K9me3 on the silenced allele, but no enrichment for H3K9ac on the expressed allele (FIG. 10A; Table 1). In contrast, for Cdh15, a significant enrichment for H3K9ac was found on the expressed allele but H3K9me3 enrichment on the silent allele was not detected (FIG. 10B). As a negative control, Sergef was analyzed, which expressed the maternal and paternal alleles equally, and no allelic differences in H3K9me3 or H3K9ac enrichment were observed for this gene (FIG. 10C).

Next, six noncanonical imprinted genes were analyzed, including Nhlrc1 (PEG), Tgfbli1 (MEG, maternally expressed gene), Slc25a29 (PEG), Eif2c2 (MEG), Trappc9 (MEG), and Bcl2l1 (PEG). A significant enrichment for H3K9me3 was found on the repressed allele for five out of six genes (Table 1). For example, Nhlrc1 and Tgfbli1 exhibited preferential expression of the paternal and maternal alleles, respectively (FIG. 10D and FIG. 10E). A significant enrichment for H3K9me3 was found on the maternal allele for Nhlrc1 (FIG. 10D) and on the paternal allele for Tgfbli1 (FIG. 10E), consistent with the repression of these alleles. Similar effects were detected for Agog and Bcl2l1, but not for Slc25a29 (Table 1). For Trappc9, significant H3K9ac enrichment was found on the maternal allele and H3K9me3 on the paternal allele (Table 1). Therefore, like canonical imprinting, noncanonical imprinting effects are associated with allele-specific chromatin modifications.

Example 8

This example demonstrates that noncanonical imprinted genes exhibit allele-specific expression in subpopulations of neurons.

Several models were tested to gain insights into the mechanisms underlying noncanonical imprinting effects at the cellular level. First, maternal or paternal allele-specific expression biases could be due to distinct, but overlapping transcripts from maternal versus paternal alleles (FIG. 11A). An approach was devised (FIG. 12) to analyze imprinting at the transcript level, and it was determined that H13, Commd1, Trappc9, Herc3, Inpp5f, Blcap, Mest, Ube3a, and Gnas were the only genes with overlapping, allele-specific isoforms (BH adjusted p value <0.01). Therefore, most noncanonical imprinting effects were not due to this phenomenon.

Alternatively, noncanonical imprinting effects could be due to (1) an allele expression bias in each cell (FIG. 11B), (2) skewed random monoallelic expression effects (FIG. 11C), or (3) allele silencing in a subpopulation of cells (FIG. 11D). To test these possibilities, an approach was devised to resolve allele-specific expression at the cellular level using RNAscope in situ hybridization probes. RNAscope probes targeting specific introns were designed by Advanced Cell Diagnostics (Newark, Calif.), and staining was performed using ACD RNAscope kits according to the manufacturer's instructions on 14-mm tissue cryosections from female B6 mice. Probes used in this study are available for ordering from ACD.

Probes were designed against intronic regions to detect nascent RNA arising from each allele in the nucleus of cells in tissue cryosections of the ARN and DRN. This approach was first evaluated for the canonical MEG, Meg3. This analysis was performed in isogenic female B6 mice, and a single focal site of allele transcription was observed in over 80% of positive cells, consistent with canonical imprinting for this gene (FIG. 11E). It was further noted that small speckles outside of the primary nuclear site of allele expression demonstrated that this staining was due to some intron retention in the nascent RNA (FIG. 13A to FIG. 13E). To resolve this issue, methods were developed in which probes were designed to specifically target rapidly processed introns (FIG. 13A to FIG. 13E). With this approach, allelic expression at the cellular level can be resolved for any gene.

Allelic expression effects were analyzed for a nonimprinted, biallelic control gene, synapsin II (Syn2), which was ubiquitously expressed in neurons, and it was found that Syn2 exhibits biallelic expression in ~77% of neurons (FIG. 11F to FIG. 11H). In contrast, the X-linked gene Maoa exhibited biallelic expression in fewer than 8% of Maoa+ neurons, as expected due to the effects of random X-inactivation (FIG. 11F to FIG. 11H). It was suspected that the apparent monoallelic Syn2+ cells were artifacts from partial nuclei cut during cryosectioning. Indeed, confocal Z-stacks of 14-mm sections revealed that 30%-35% of DAPI+ nuclei are partial (FIG. 13F and FIG. 13G). Therefore, based on the Syn2 biallelic control, it was concluded that this method has a background effect in which ~23% of monoallelic cells are potentially false due to sectioning artifacts.

Figure 11I:
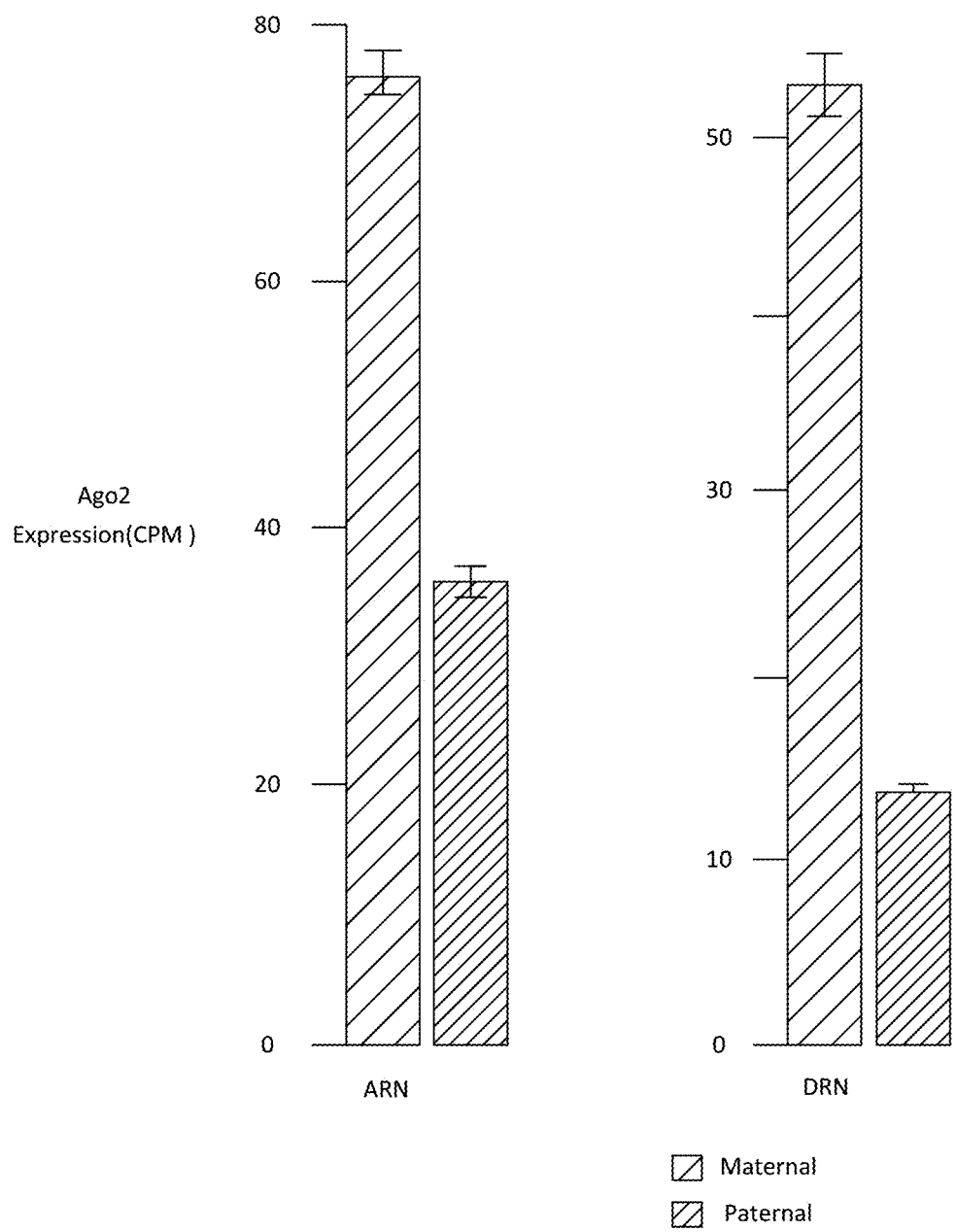
Figure 11J:
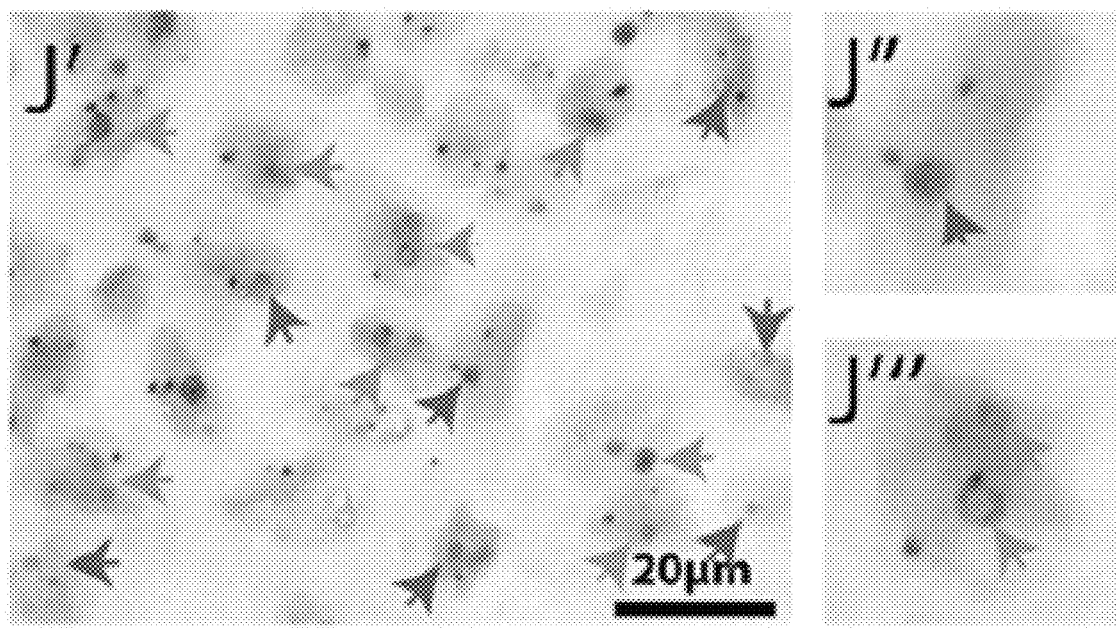
Figure 11K:
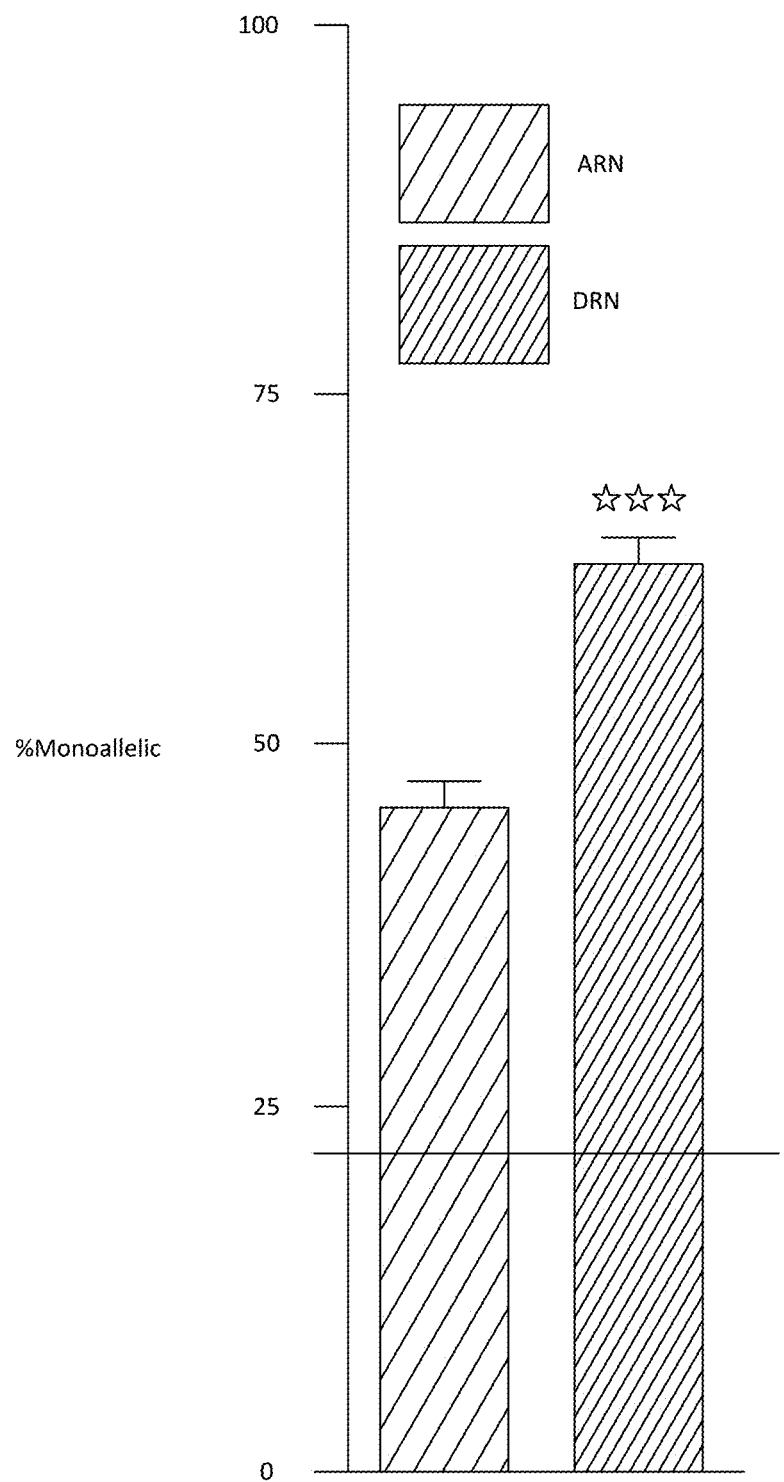
Figure 11L:
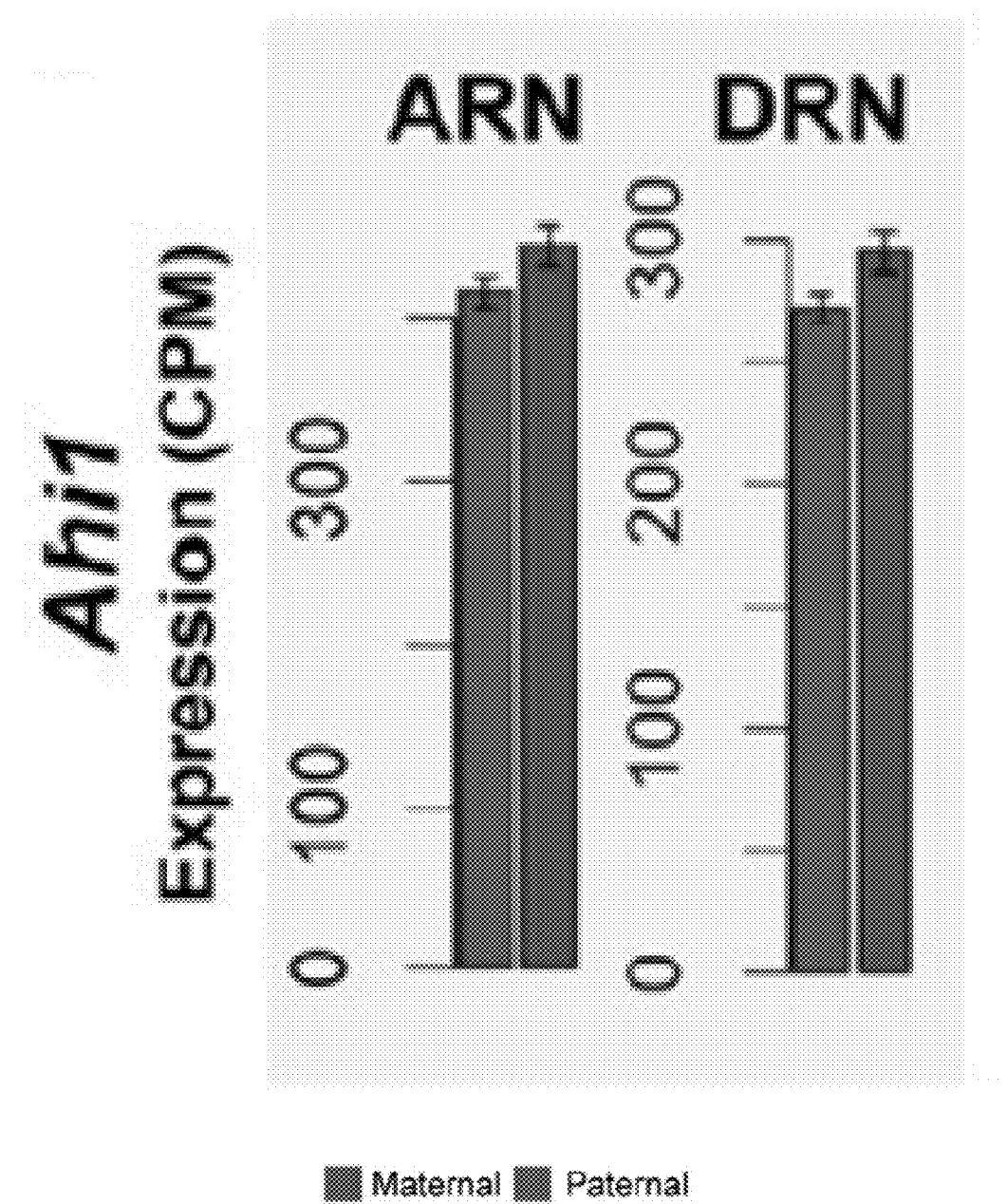
Figure 11M:
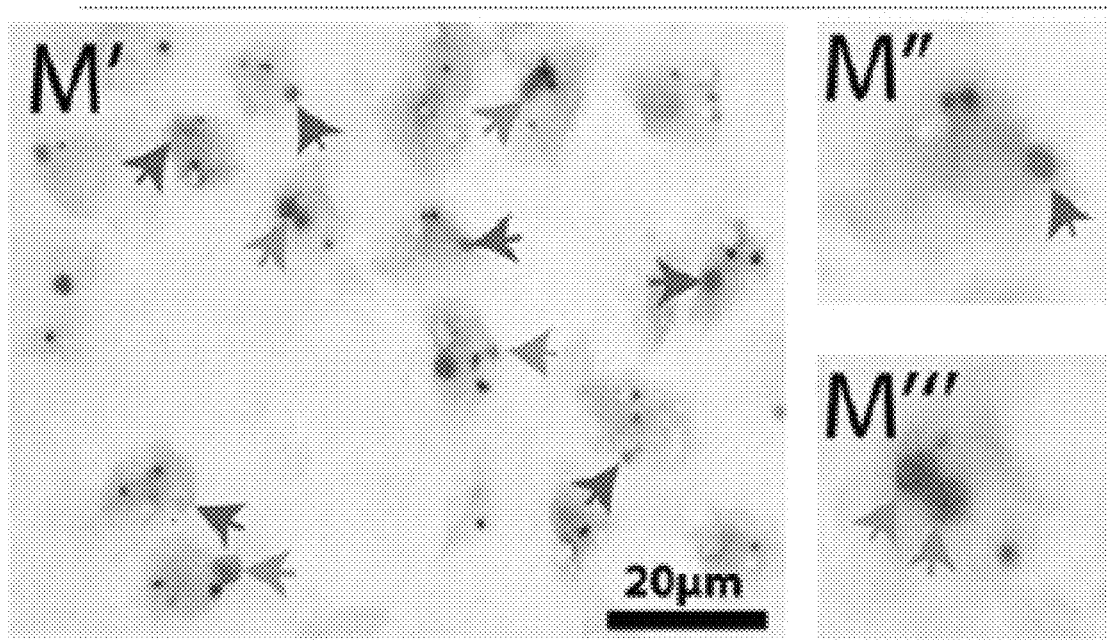
Figure 11N:
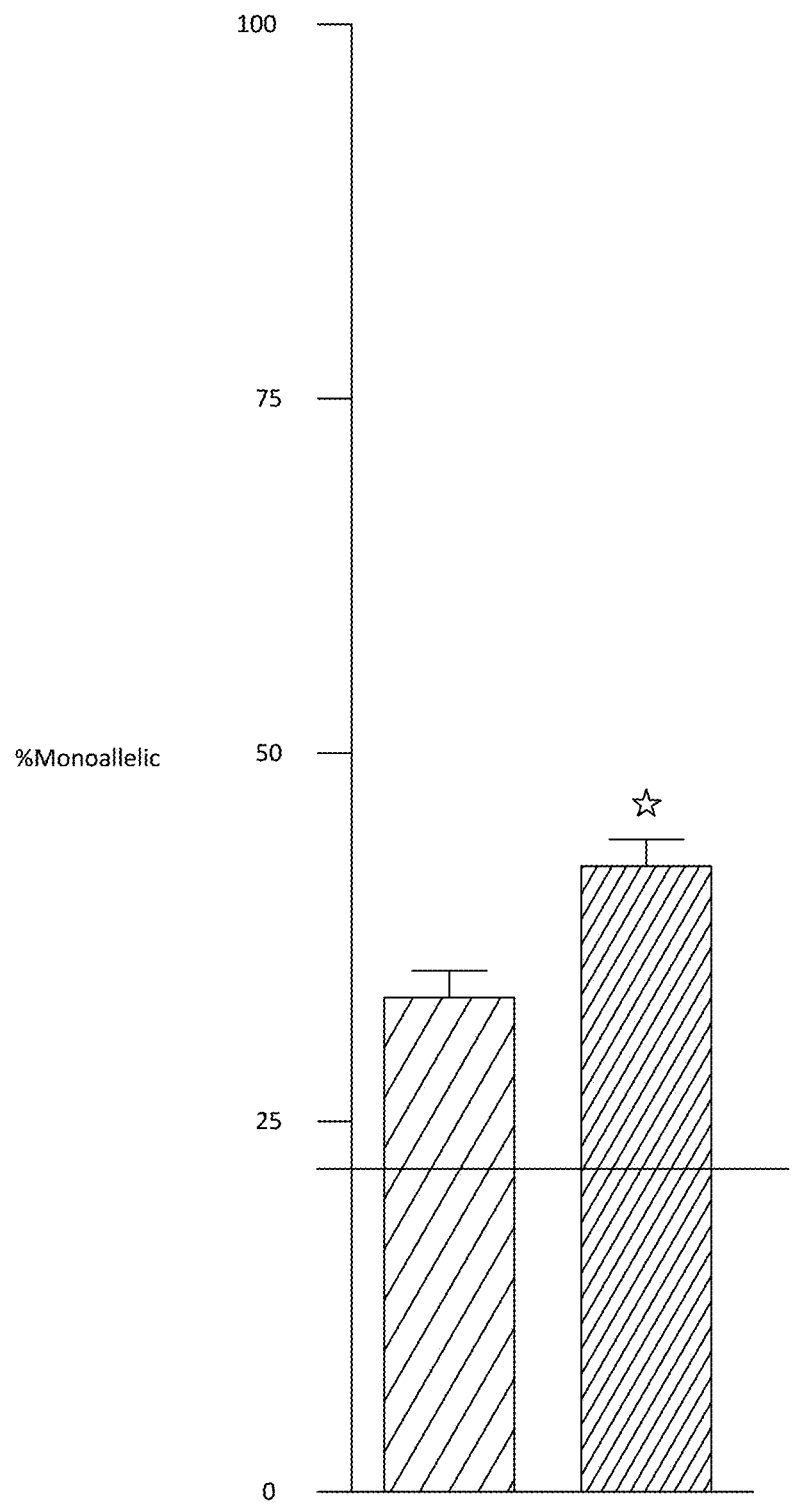
Figure 11O:
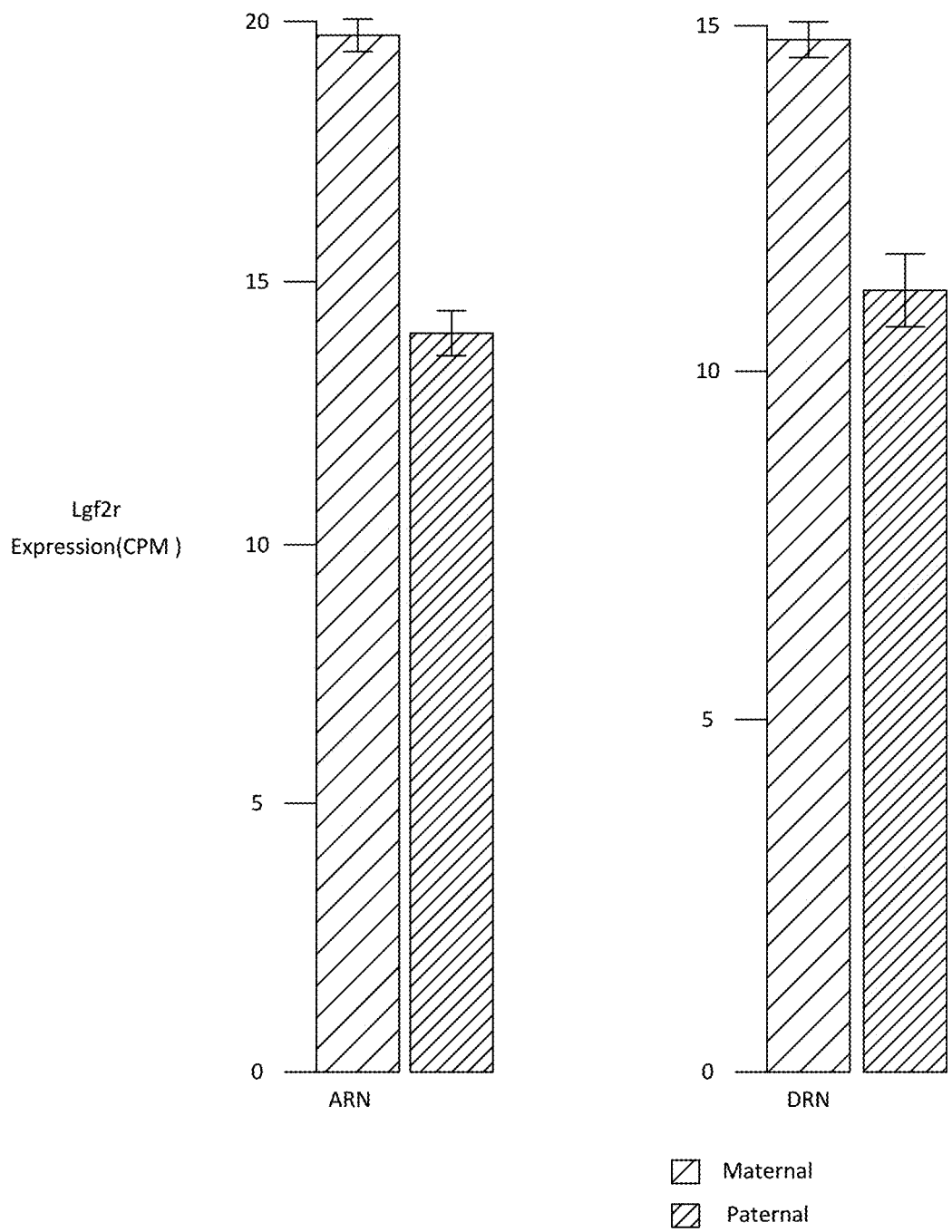
Figure 11P:
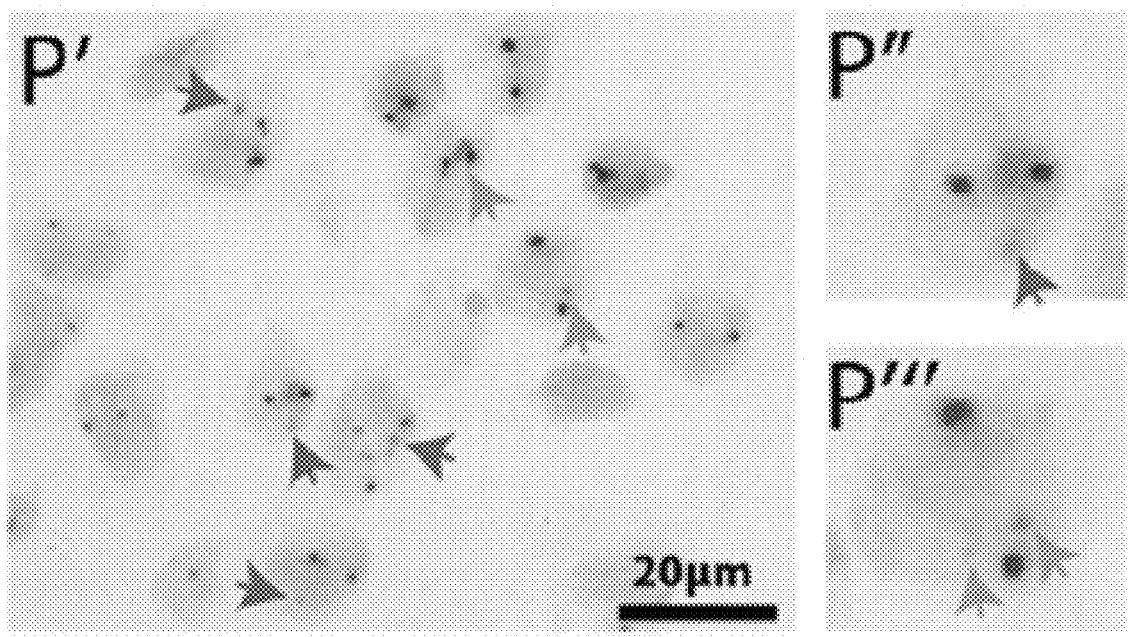
Figure 11Q:
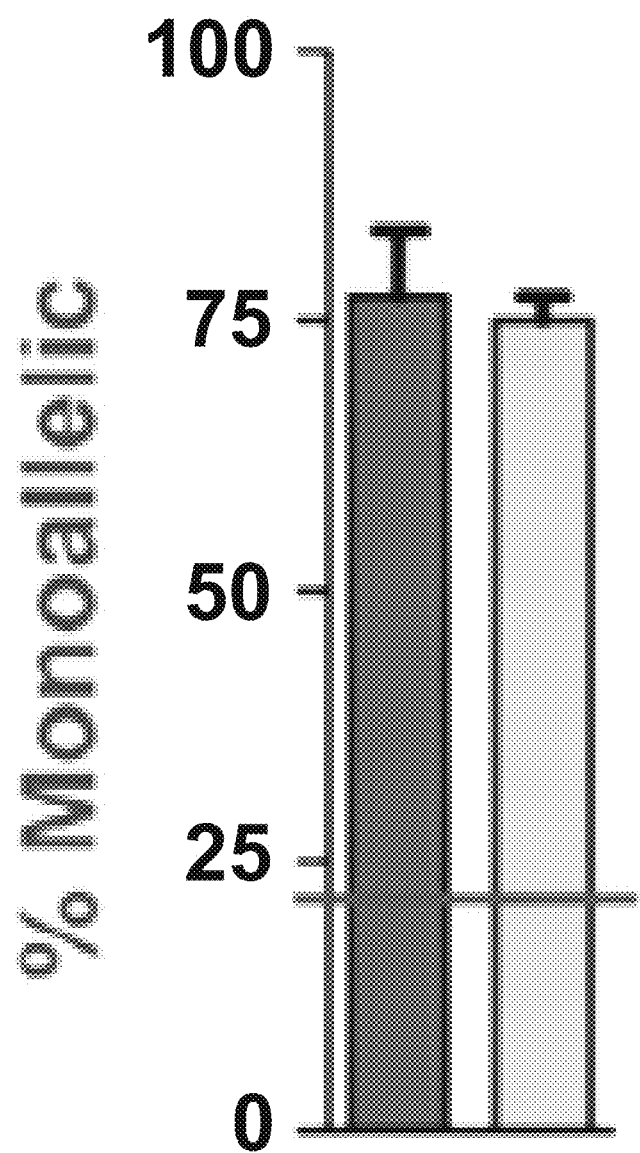

Next, this approach was used to analyze allelic expression effects for noncanonical imprinted genes and double labeling was performed with Syn2, as an internal biallelic control and neuron marker. The first gene analyzed was Ago2, which exhibited a 2-fold maternal allele bias in the ARN and 3-fold maternal bias in the DRN (FIG. 11I). A 46% and 63% of Ago2+ cells were found to be monoallelic in the ARN and DRN, respectively, which revealed significantly more monoallelic cells in the DRN, which had stronger imprinting (FIG. 11J and FIG. 11K). Ahi1 exhibited a paternal allele bias by RNAseq, and it was found that 34% and 40% of Ahi1+ cells were monoallelic in the ARN and DRN, respectively (FIG. 11L to FIG. 11N). Finally, Igf2r was found to be a noncanonical MEG in the brain and it was determined that it exhibits monoallelic expression in ~75% of positive cells in the ARN and DRN (FIG. 11O to FIG. 11Q). Importantly, the number of monoallelic cells detected for Ago2, Ahi1, and Igf2r was approximately 2-fold higher, or more, than the background (red line in FIG. 11H, FIG. 11K, and FIG. 11N), and monoallelic effects were clearly identified in neurons that were biallelic for Syn2 (FIG. 11G", FIG. 11J", and FIG. 11M"), indicating bona fide allele-specific expression effects. To further confirm these findings, a fluorescent staining and confocal imaging strategy was devised to detect whole nuclei, and it was determined that bona fide monoallelic and biallelic cellular subpopulations existed for cells with fully intact nuclei for both Ahi1 (FIG. 13H) and Ago2 (FIG. 13I). Based on these findings, it was concluded that autosomal noncanonical imprinted genes exhibit allele-specific expression effects in subpopulations of neurons in the brain.

Example 9

This example demonstrates that noncanonical imprinting effects influence the monoamine pathway and offspring phenotypes.

Gene ontology analysis and literature searches provided insights into the biological pathways that contain imprinted genes. In the ARN and DRN, several noncanonical imprinted genes were discovered with roles in monoamine signaling, including tyrosine hydroxylase (Th, MEG), Ddc (MEG), Maoa (X-linked MEG), Tgflbli (MEG), and Ahi1 (PEG), as well as known canonical imprinted genes that influence monoamine signaling, including RasGrf1 and the snoRNA, HBII-52 (FIG. 14A and FIG. 14B) (Doe et al., *Hum. Mol. Genet.,* 18: 2140-2148 (2009); Fernandez-Medarde et al., *Biochim. Biophys. Acta,* 1815: 170-188 (2011)). Pyrosequencing was used to evaluate the imprinting status of the noncanonical imprinted genes in major monoaminergic nuclei, as well as Dbh (dopamine beta-hydroxylase), which regulates norepinephrine (NE) synthesis, and Tph2 (tryptophan hydroxylase), which regulates serotonin synthesis. This analysis was performed in the ARN, DRN, ventral tegmental area (VTA), and the locus coeruleus (LC).

This study revealed that Dbh and Tph2 are not imprinted in the LC and DRN, respectively (FIG. 14C). However, Th exhibited a significant maternal allele bias (FIG. 14D, p<0.05, main effect of cross, two-way ANOVA). The bias appeared in the ARN, DRN, and LC, but not in the VTA, though this brain region difference did not result in a significant interaction effect between cross and brain region (FIG. 14D). On the other hand, Ddc exhibited a maternal bias that was significantly different between brain regions (FIG. 14E, p<0.0001, interaction between cross and brain region). Ddc imprinting was strongest in the ARN and the LC, weaker in the DRN, and was not significant in the VTA (FIG. 14E, Tukey HSD post hoc test). Tgfbli1 interacts with the dopamine transporter (DAT) (Carneiro et al., *J. Neurosci*, 22: 7045-7054 (2002), and exhibited a significant maternal bias in each of the brain regions (FIG. 14F). Ahi1 can influence serotonin signaling (Wang et al., *J. Biol. Chem.*, 287: 2237-2246 (2012)) and exhibited a significant paternal bias in each brain region (FIG. 14G). Next, RNAscope probes were used to analyze allelic expression at the cellular level for Ddc in B6 female mice. It was found that the number of $Ddc^+$ monoallelic cells in the ARN was significantly greater than in the VTA (FIG. 14H to FIG. 14J). Therefore, more monoallelic cells are detected in the brain region with stronger imprinting.

Finally, subpopulations of $Th^+$ neurons were found in the brain that exhibited allele-specific expression effects (FIG. 14K); it was then tested whether Th imprinting effects influenced the impact of inherited mutations on offspring behavior. Th mutant mice on a B6 background were obtained and reciprocal $Th^{-/+}$ (maternal deletion) and $Th^{+/-}$ (paternal deletion) heterozygous offspring were generated, as well as wild-type littermates. Th heterozygous mice are known to exhibit reduced catecholamine levels in the brain and significant behavioral changes (Kobayashi et al., *J. Neurosci*, 20: 2418-2426 (2000)), and catecholamines influence motivated behaviors.

Open-field testing was performed to compare $Th^{+/-}$ and $Th^{+/-}$ offspring. Open-field testing was analyzed by Ethovision software (Noldus Information Technology, Wageningen, The Netherlands). A significant effect was observed from the open-field testing for the parental origin of the mutation in males and females, such that offspring with a mutated maternal allele spent more time in the center of the arena compared to offspring with a mutated paternal allele (FIG. 14L). No difference was observed between the wild-type littermates (FIG. 14M), and the total distance traveled was not different for any genotype. Next, a sucrose intake test was performed. Sucrose intake was determined for each concentration from 2 days of testing during the light phase with alternate cage bottle positions on each day. In the sucrose intake test, a hedonic measure, offspring with a mutated maternal allele ($Th^{-/+}$) were found to consume significantly more sucrose solution compared to those with a mutated paternal allele ($Th^{+/-}$) (FIG. 14N). No difference was observed between the wild-type littermates (FIG. 14O). In summary, noncanonical imprinting influences genes in the monoamine pathway, in some cases the effects are brain region specific, and effects at a single locus can significantly, albeit modestly, influence the effect of inherited mutations on behavior.

Example 10

This example describes the calculation of intron retention score thresholds that allow for reliable detection of allelic expression by in situ hybridization.

RNASeq was performed on polyA purified RNA from adult female mouse dorsal raphe nucleus and on whole transcriptome using the Illumina TruSeq Ribo-Zero system on purified nuclear RNA from adult female mouse dorsal raphe nucleus. From these RNASeq datasets, the FPKM was calculated for every exon and intron for each gene expressed in the tissue and intron retention scores were computed for each intron. Sixteen different introns were then randomly selected with a range of different intron retention scores for fifteen different genes (FIG. 15A and FIG. 15B). In situ probes to each intron were designed and staining was performed on adult female mouse brain tissue sections of the dorsal raphe nucleus. For each of the genes and introns analyzed, the probes were classified according to the absence (FIG. 15A) or presence (FIG. 15B) of intron retention effects that obscured resolution of allelic expression in the nucleus. It was found that nine probes had acceptably low levels of intron retention such that allelic expression could be resolved at the cellular level in the brain (FIG. 15A). These probes included Ahi1 (Albenson Helper Protein 1):Intron 9, Syn2 (Synapsin 2):Intron 1, Maoa (Monoamine Oxidase A):Intron 1, Mtap1b (microtubule-associated protein IB):Intron 6, Igf2r (Insulin growth factor 2):Intron 1, Ddc (Dopa decarboxylase): Intron 19, Tspan (Teraspanins): Intron 4, Atp8a1(ATPase phospholipid transporting 8A1): Intron 21, and Agog (Argonauts 2): Intron 3. This analysis also revealed seven probes with high levels of intron retention, which partially or completely prevented resolution of allelic expression in the nucleus of the positive cells (FIG. 15B). These probes included Th (Tyrosine Hydroxylase): Intron 12, Sparcl1(Sparc like 1):Intron 7, Ank2(Ankyrin 2):Intron 7, Npy(Neuropeptide Y):Intron 2, Pld3(Phospholipase D 3):Intron 5, Ddc(Dopa decarboxylase):Intron 6, and Ghrh(Growth hormone releasing hormone):Intron 1. Therefore, by randomly analyzing 16 intronic probes, a spectrum of different intron retention effects were identified.

To define the intron retention score and expression level thresholds at which intron retention effects obscure allelic expression, the intron retention scores for each targeted intron were plotted against the expression level for each intron (FPKM) for the polyA purified RNASeq data (FIG. 15C) and the whole nuclear transcriptome RNASeq data (FIG. 15D). For the polyA purified RNASeq study, it was found that a reduced intron retention score clearly enriched for probes that accurately resolve allelic expression (FIG. 15C), while a higher intron retention score enriched for probes that detect intron retention effects by in situ hybridization (black text, FIG. 15C). Based on these results, it was estimated that an intron retention score less than or equal to 0.0005 is an effective threshold to reduce intron retention background labeling. For the whole nuclear transcriptome RNASeq study, the intron retention score was not found to separate the probes according to their staining characteristics as effectively (FIG. 15D). However, it was estimated that an intron retention score less than or equal to 0.018 is an effective threshold to reduce intron retention effects.

The results of this example demonstrate the determination of effective intron retention score thresholds from polyA purified RNA and whole nuclear transcriptome profiling that control the background labeling that may obscure resolution of allelic expression by in situ hybridization.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for isolating and identifying allele-specific expression of a gene in a single cell, which method comprises:
    (a) providing a cell comprising a gene of interest,
    (b) expressing the gene of interest in the cell,
    (c) isolating one or more nascent RNA molecules transcribed from the gene of interest,
    (d) sequencing the one or more nascent RNA molecules isolated in (c),
    (e) determining the fragments per kilobase per millions (FPKM) for each exon and each intron present in the one or more nascent RNA molecules,
    (f) calculating an intron retention score (IRS) for each intron of the one or more nascent RNA molecules as follows:

$$IRS = \frac{intron\ FPKM}{mean\ FPKM\ for\ two\ flanking\ exons},$$

wherein the mean FPKM for two flanking exons is the mean FPKM for each exon contiguous with the intron,
    (g) ranking each intron of the one or more nascent RNA molecules according to the intron retention score for each intron and identifying rapidly processed introns, wherein an intron retention score less than or equal to 0.018 identifies an intron as being rapidly processed, and an intron retention score greater than 0.018 identifies an intron as not being rapidly processed,
    (h) designing one or more nucleic acid probes that specifically bind to an intron identified by steps (a)-(g) as being rapidly processed, wherein the one or more probes comprise a detectable label,
    (i) conducting RNA in situ hybridization on the rapidly processed intron using the one or more probes, and
    (j) analyzing a signal produced by the detectable label, wherein the presence of one signal indicates that the gene of interest is expressed from one allele and the presence of two signals indicates that the gene of interest is expressed from two alleles.

2. The method of claim 1, wherein the one or more nascent RNA molecules is in the process of posttranscriptional processing and is messenger RNA (mRNA).

3. The method of claim 2, wherein the mRNA is polyadenylated mRNA.

4. The method of claim 1, further comprising comparing the signal produced by the detectable label to an internal control gene that exhibits biallelic expression.

* * * * *